US010851054B2

(12) United States Patent
Bougeret et al.

(10) Patent No.: US 10,851,054 B2
(45) Date of Patent: Dec. 1, 2020

(54) DERIVATIVES OF INDOLE FOR THE TREATMENT OF CANCER, VIRAL INFECTIONS AND LUNG DISEASES

(71) Applicants: BIOKINESIS, Paris (FR); CENTRE NATIONAL DE LA RECHERCHE SCIENTIFIQUE, Paris (FR)

(72) Inventors: Cecile Bougeret, Nevers (FR); Catherine Guillou, Gif-sur-Yvette (FR); Julien Rouleau, Gif-sur-Yvette (FR); Julie Rivollier, Villebon-sur-Yvette (FR); Denis Carniato, Marcoussis (FR)

(73) Assignees: BIOKINESIS, Paris (FR); CENTRE NATIONAL DE LA RECHERCHE SCIENTIFIQUE, Paris (FR)

(*) Notice: Subject to any disclaimer, the term of this patent is extended or adjusted under 35 U.S.C. 154(b) by 0 days.

(21) Appl. No.: 16/257,096

(22) Filed: Jan. 25, 2019

(65) Prior Publication Data
US 2019/0169124 A1 Jun. 6, 2019

Related U.S. Application Data

(62) Division of application No. 15/586,343, filed on May 4, 2017, now Pat. No. 10,189,782, which is a division of application No. 14/647,521, filed as application No. PCT/EP2013/075776 on Dec. 6, 2013, now Pat. No. 9,643,923.

(60) Provisional application No. 61/734,451, filed on Dec. 7, 2012.

(30) Foreign Application Priority Data

Dec. 7, 2012 (EP) ..................... 12306536
Mar. 1, 2013 (EP) ..................... 13157372

(51) Int. Cl.
C07D 209/04 (2006.01)
A61K 31/404 (2006.01)
C07D 209/18 (2006.01)
C07F 9/09 (2006.01)
C07F 9/40 (2006.01)
C07D 401/14 (2006.01)
C07D 405/14 (2006.01)
C07D 401/06 (2006.01)
C07F 9/572 (2006.01)
A61K 31/4439 (2006.01)
A61K 31/444 (2006.01)
A61K 31/496 (2006.01)
A61K 31/675 (2006.01)
A61K 31/683 (2006.01)
A61K 45/06 (2006.01)
A61K 31/685 (2006.01)
C07C 211/63 (2006.01)
C07D 209/26 (2006.01)
C07D 403/06 (2006.01)

(52) U.S. Cl.
CPC .......... C07D 209/18 (2013.01); A61K 31/404 (2013.01); A61K 31/444 (2013.01); A61K 31/4439 (2013.01); A61K 31/496 (2013.01); A61K 31/675 (2013.01); A61K 31/683 (2013.01); A61K 31/685 (2013.01); A61K 45/06 (2013.01); C07C 211/63 (2013.01); C07D 209/04 (2013.01); C07D 209/26 (2013.01); C07D 401/06 (2013.01); C07D 401/14 (2013.01); C07D 403/06 (2013.01); C07D 405/14 (2013.01); C07F 9/09 (2013.01); C07F 9/40 (2013.01); C07F 9/5728 (2013.01)

(58) Field of Classification Search
CPC ........................... C07D 209/04; A61K 31/404
See application file for complete search history.

(56) References Cited

U.S. PATENT DOCUMENTS 9,643,923 B2  5/2017  Bougeret et al.
10,189,782 B2  1/2019  Bougeret et al.

FOREIGN PATENT DOCUMENTS

WO  WO 01/98299      12/2001
WO  WO 2007/106236    9/2007
WO  WO 2010/150211   12/2010
WO  WO 2014/086964    6/2014
WO  WO 2018/077795    5/2018

OTHER PUBLICATIONS

Claims pending in U.S. Appl. No. 16/344,390, 2019, pp. 1-9.
Demirkiran, F. "Is endometriosis a preneoplastic condition?" Women's Health, 2015, pp. 701-703, vol. 11, No. 5.
Kvaskoff, M. et al. "Endometriosis: a high-risk population for major chronic diseases?" Human Reproduction Update, 2015, pp. 500-516, vol. 21, No. 4.
Written Opinion in International Application No. PCT/EP2017/076990, dated Dec. 4, 2017, pp. 1-7.
Claerhout, S. et al. "Gene Expression Signature Analysis Identifies Vorinostat as a Candidate Therapy for Gastric Cancer" PLoS ONE, Sep. 2011, pp. 1-10, vol. 6, Issue 9, e24662.
Duan, J. et al. "Positive expression of KIF20A indicates poor prognosis of glioma patients" OncoTargets and Therapy, 2016, pp. 6741-6749, vol. 9.
Gasnereau, I. et al. "KIF20A mRNA and Its Product MKlp2 Are Increased During Hepatocyte Proliferation and Hepatocarcinogenesis" The American Journal of Pathology, Jan. 2012, pp. 131-140, vol. 180, No. 1.
Ho, J.R. et al. "Deregulation of Rab and Rab Effector Genes in Bladder Cancer" PLoS ONE, Jun. 2012, pp. 1-16, vol. 7, Issue 6, e39469.

(Continued)

Primary Examiner — Samira J Jean-Louis
(74) Attorney, Agent, or Firm — Saliwanchik, Lloyd & Eisenschenk

(57) ABSTRACT

The present invention relates to a new class of indole derivatives, having a particular MKlp2 inhibition profile and useful as a therapeutic agent, in particular for the treatment of cancer, viral infections and lung diseases.

15 Claims, 2 Drawing Sheets

(56) References Cited

OTHER PUBLICATIONS

Figure 1:
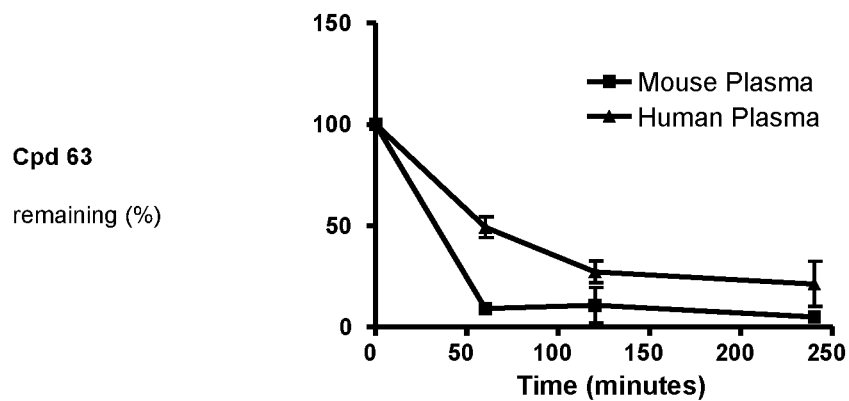

Imai, K. et al. "Identification of HLA-A2-restricted CTL epitopes of a novel tumour-associated antigen, KIF20A, overexpressed in pancreatic cancer" *British Journal of Cancer*, 2011, pp. 300-307, vol. 104, No. 2.
Khongkow, P. et al. "Paclitaxel targets FOXM1 to regulate KIF20A in mitotic catastrophe and breast cancer paclitaxel resistance" *Oncogene*, 2015, pp. 1-13.
Liu, S.-L. et al. "Overexpression of Kinesin Family Member 20A Correlates with Disease Progression and Poor Prognosis in Human Nasopharyngeal Cancer: A Retrospective Analysis of 105 Patients" *PLoS ONE*, 2017, pp. 1-18.
Saito, K. et al. "Functional analysis of KIF20A, a potential immunotherapeutic target for glioma" *J Neurooncol*, Mar. 2017, pp. 1-12, vol. 132, No. 1.
Shi, C. et al. "Aberrantly activated Gli2-KIF20A axis is crucial for growth of hepatocellular carcinoma and predicts poor prognosis" *Oncotarget*, Mar. 2016, pp. 1-14, vol. 7, No. 18.
Song, X. et al. "Distinct Diagnostic and Prognostic Values of Kinesin Family Member Genes Expression in Patients with Breast Cancer" *Medical Science Monitor*, 2018, pp. 9442-9464, vol. 24.
Stangel, D. et al. "Kif20a inhibition reduces migration and invasion of pancreatic cancer cells" *Journal of Surgical Research*, Jul. 2015, pp. 1-10, vol. 197, No. 1.
Taniuchi, K. et al. "Down-regulation of RAB6KIFL/KIF20A, a Kinesin Involved with Membrane Trafficking of Discs Large Homologue 5, Can Attenuate Growth of Pancreatic Cancer Cell" *Cancer Research*, 2005, pp. 105-112, vol. 65, No. 1.
Taniuchi, K. et al. "KIF20A-Mediated RNA Granule Transport System Promotes the Invasiveness of Pancreatic Cancer Cells" *Neoplasia*, Dec. 2014, pp. 1082-1093, vol. 16, No. 12.
Yamashita, J. et al. "Kinesin Family Member 20A is a Novel Melanoma-associated Antigen" *Acta Derm Venereol*, 2012, pp. 1-5, vol. 92, No. 6.
Yan, G.-R. et al. "Genistein-induced mitotic arrest of gastric cancer cells by downregulation KIF20A, a proteomics study" *Proteomics*, 2012, pp. 2391-2399, vol. 12.
Zhang, W. et al. "High Expression of KIF20A Is Associated with Poor Overall Survival and Tumor Progression in Early-Stage Cervical Squamous Cell Carcinoma" *PLoS ONE*, Dec. 2016, pp. 1-21, vol. 11, No. 12.
Groth-Pedersen, L. et al. "Identification of Cytoskeleton-Associated Proteins Essential for Lysosomal Stability and Survival of Human Cancer Cells" *PLoS ONE*, Oct. 11, 2012, pp. 1-11, vol. 7, No. 10, e45381.
Tcherniuk. S. et al. "Relocation of Aurora B and Survivin from Centromeres to the Central Spindle Impaired by a Kinesin-Specific MKLP-2 Inhibitor" *Angew. Chem. Int. Ed.*, 2010, pp. 8228-8231, vol. 49.
Dolusic, E. et al. "Tryptophan 2,3-Dioxygenase (TDO) Inhibitors. 3-(2-(Pyridyl)ethenyl)indoles as Potential Anticancer Immunomodulators" *Journal of Medicinal Chemistry*, 2011, pp. 5320-5334, vol. 54.
Tarleton, M. et al. "Cytotoxic 2-phenyacrylnitriles, the importance of the cyanide moiety and discovery of potent broad spectrum cytotoxic agents" *European Journal of Medicinal Chemistry*, 2012, pp. 65-73, vol. 57.
Ettmayer, P. et al. "Lessons Learned from Marketed and Investigational Prodrugs" *Journal of Medical Chemistry*, 2004, pp. 2393-2404, vol. 47, No. 10.
Jordan, V. C. "Tamoxifen: a most unlikely pioneering medicine" *Nature Reviews Drug Discovery*, Mar. 2003, pp. 205-213, vol. 2.
Stella, V. J. "Prodrugs as therapeutics" *Expert Opin. Ther. Patents*, 2004, pp. 277-280, vol. 47, No. 3.
Testa, B. "Prodrug research: futile or fertile?" *Biochemical Pharmacology*, 2004, pp. 2097-2106, vol. 68.
Wolf, M. E. et al. "Burger's medicinal chemistry and drug discovery" *Wiley Interscience*, 1996, pp. 949-982, 5$^{th}$ ed., editor: Balant, vol. 1.

DERIVATIVES OF INDOLE FOR THE TREATMENT OF CANCER, VIRAL INFECTIONS AND LUNG DISEASES

CROSS-REFERENCE TO RELATED APPLICATIONS

This application is a divisional of U.S. application Ser. No. 15/586,343, filed May 4, 2017, now U.S. Pat. No. 10,189,782, which is a divisional of U.S. application Ser. No. 14/647,521, filed May 27, 2015, now U.S. Pat. No. 9,643,923, which is the national stage of international application No. PCT/EP2013/075776, filed Dec. 6, 2013, which claims the benefit of U.S. Provisional Application Ser. No. 61/734,451, filed Dec. 7, 2012.

FIELD OF THE INVENTION

The present invention relates to derivatives of indoles and to their application as therapeutics, and in particular to treat the cancer.

BACKGROUND OF THE INVENTION

Cell division is a highly dynamic process, which depends on the proper interaction of mitotic spindle microtubules (MTs) with chromosomes during mitosis. Because of the dynamic nature of mitosis, proteins involved in the process are prime targets for the development of inhibitors that can be used as antimitotic agents with a potential chemotherapeutic value.

Currently, many anti-cancer drugs used in cancer chemotherapy are antimitotic agents, such as taxanes (Paclitaxel, Docetaxel) which target tubulin, the basic component for the polymerization of mitotic microtubules and/or vinca-alkaloids, such as vinorelbine or vinblastine.

Other anti-cancer drugs are alkylating agents, such as cis-platine, DNA intercaling agents, such as doxorubicin, Topoisomerase I or II inhibitors, such as respectively camptothecin and etoposide, and RNA/DNA antimetabolites, such as 5-fluorouracil.

In addition to inhibitors aiming at MT assembly/dynamics and inhibitors targeting mitotic kinases, a new class of targets has emerged, that of kinesin based motor proteins.

Kinesins are proteins which use the free energy of ATP hydrolysis to drive intracellular movement and influence cytoskeleton organization (R. D. Vale and R. J. Fletterick, Annu. Rev. Cell. Dev. Biol. 13, 745-777 (1997)). More than 90 members of this family are known. In particular, a RNAi screen in human cells has identified at least 12 different members of such kinesin superfamily as being actively involved in cell division.

Several members of the kinesin superfamily play thus key roles in mitosis and some of them, such as MKlp2 (also known as KIF20A/RAB6KIFL/Rabkinesin-6, protein number NP_005724), are essential for cytokinesis and more particularly for the implementation of the cleavage furrow and spindle midzone formation. Cytokinesis marks the final step of mitosis and the cell cycle, leading to the production of two daughter cells endowed with a complete set of chromosomes and cytoplasmic organelles.

Many steps of cytokinesis, from cleavage furrow and spindle midzone formation, to transport of proteins to the cell division plane as well as furrow ingression are thought to be dependent on the function of different members of the kinesin superfamily, including Mitotic-Kinesin-Like-Protein-1 (MKlp1) and -2 (MKlp2), M-Phase-Phosphoprotein-1 (MPP1), human KIF4A (and its very close, with 99% identity, homologue KIF4B, both kinesin-4 family) and KIF14. Another protein is Eg5 (also known as KSP) which drives the movement of microtubules in vitro.

Inhibitors of kinesins have already been reported (R. Sakowicz et al., Science 280, 292-295 (1998)) or disclosed, notably in U.S. Pat. Nos. 6,489,134 and 6,890,933 but such inhibitors do not show a potential efficacy against MKlp2.

MKlp2 has been shown to be essential for normal cleavage furrow ingression and cytokinesis. Depletion of MKlp2 by siRNA leads to binucleated cells (K Taniuchi et al.

Cancer Research 65, 105-112 (2005)). MKlp2 has also been identified as a cytoskeleton-associated proteins essential for lysosomal stability and survival of human cancer cells (L.

Groth-Pedersen et al. PLoS One. 7(10), e45381 (2012)). Accordingly, it can thus constitute new target for the development of novel therapeutic strategies against cancer or diseases linked to uncontrolled and/or abnormal cell growth.

Currently, there is a lack of potent inhibitors for this member of the kinesin family that could be used as an anti-cancer agent and for which the specificity of the anti-MKlp2 activity could be sufficient to prevent off target toxicity.

The use of kinesin inhibitors in HIV infection treatment has also been reported in patent application EP 2 455 456. In addition, mitotic kinesin inhibitors are also used for treating lung disease, particularly pulmonary arterial hypertension, such as described in patent application WO 2012/009097.

The inventors have demonstrated that some derivatives of indole are selective inhibitors for MKlp2 in the publication S. Tcherniuk et al. (Angew. Chem. Int. 49, 8228-8231 (2010)) and in the patent application WO 2010/150211. However, alternative or improved inhibitors are still very useful and necessary. A new generation of inhibitors of cytokinesis may in particular be used for the treatment of cancer.

SUMMARY OF THE INVENTION

The present invention relates to compounds of formula (I):

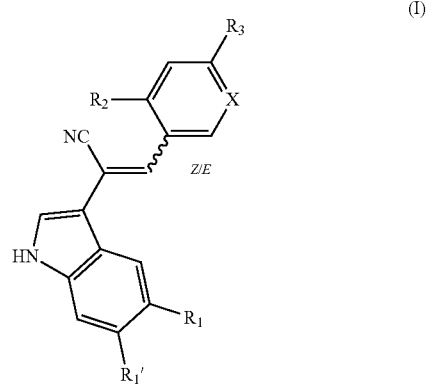

wherein:
X represents a nitrogen atom, a C—CN unit or a $N^+$—$O^-$ unit, preferably a nitrogen atom or a C—CN unit;
$R_1$ and $R_1'$ are such that one is H and the other represents a halogen or a ($C_1$-$C_6$)alkoxy group, optionally substituted by a carboxylic group or one —NR$_{11}$R$_{12}$ unit wherein R$_{11}$ and R$_{12}$ represent H or a (C$_1$-C$_6$)alkyl group or R$_{11}$ and R$_{12}$ taken together form a 3- to 7-membered ring optionally interrupted by one or several heteroatoms, preferably a (C$_1$-C$_3$)alkoxy group;

R$_2$ represents:
- a radical (C$_1$-C$_6$)alkoxy, (C$_3$-C$_6$)cycloalkoxy, aryloxy, heteroaryloxy, (C$_1$-C$_6$)alkyl-aryloxy, (C$_1$-C$_6$)alkyl-heteroaryloxy, said radicals being optionally substituted by at least one halogen, or a radical thio-(C$_1$-C$_6$)alkyl, thio-aryl, thio-heteroaryl, thio-(C$_1$-C$_6$)alkyl-aryl or thio-(C$_1$-C$_6$)-alkyl-heteroaryl, said radicals being optionally substituted by at least one halogen or by a (C$_1$-C$_6$)alkoxy group,
- a —NR$_4$R$_5$ unit, a O—(C$_1$-C$_6$)alkyl-NR$_4$R$_5$ unit or a S—(C$_1$-C$_6$)alkyl-NR$_4$R$_5$ unit wherein R$_4$ and R$_5$ represent H, a (C$_1$-C$_6$)alkyl group, or R$_4$ and R$_5$ taken together form a 3- to 7-membered ring, optionally interrupted by one or several heteroatoms, with the proviso that at least one among R$_4$ and R$_5$ is not H,
- a NHCOR$_6$ unit wherein R$_6$ represents (C$_1$-C$_6$)alkyl group,
- an aryl or heteroaryl group optionally substituted by at least one halogen, a trifluoromethyl group, or a (C$_1$-C$_3$)alkoxy group, a halogen, with the proviso that if R$_1$ or R$_1$' is a (C$_1$-C$_3$)alkoxy group, then R$_2$ is not a halogen; and R$_3$ represents a hydrogen, a (C$_1$-C$_3$)alkyl group, a (C$_1$-C$_3$)alkoxy group or a halogen, advantageously a fluorine;

and the prodrugs thereof, in which the nitrogen atom of the indole core is substituted by a group selected from the group consisting of a COR$_7$ and a CO$_2$R$_7$ group, wherein R$_7$ represents:
- a (C$_1$-C$_6$)alkyl group, optionally substituted by at least a hydroxy group, a (C$_1$-C$_6$)alkyloxy group, a (C$_1$-C$_6$)$_n$ polyalkyloxy group wherein n is 1<n<6, a phosphate or pyrophosphate group and salts or (C$_1$-C$_3$)alkyl ester thereof, a R$_8$ group, a —NHCO$_2$R$_8$ unit, a COR$_8$ group, or a CO$_2$R$_8$ group, wherein R$_8$ is:
- a (C$_1$-C$_6$)alkyl group,
- an aryl, a (C$_1$-C$_6$)alkylaryl, a heteroaryl,
- a —NR$_9$R$_{10}$ unit wherein R$_9$ and R$_{10}$ represent a hydrogen, a (C$_1$-C$_6$)alkyl group, or R$_9$ and R$_{10}$ taken together form a 3- to 7-membered ring, optionally interrupted by one or several heteroatoms, and optionally the ring being substituted by at least one (C$_1$-C$_6$)alkyl group;
- a NH—NR$_9$R$_{10}$ unit wherein R$_9$ and R$_{10}$ are such as defined above; or
- a saturated heterocycle or a heteroaryl;

or one of its pharmaceutically acceptable salts;
with the proviso that the compound is not (Z)-3-(4-ethoxy-pyridin-3-yl)-2-(5-methoxy-1H-indol-3-yl)-acrylonitrile.

In a particular embodiment, compounds having formula (I) as defined above are (Z)-isomers (formula Ia) or a prodrug thereof as defined above.

In another particular embodiment, compounds having formula (I) as defined above are (E)-isomers (formula Ib) or a prodrug thereof as defined above.

Particularly, the compound has formula (I), (Ia), or (Ib) as defined above with R$_1$' being H. More particularly, the compound has formula (I), (Ia), or (Ib) as defined above with R$_1$ being a halogen chosen among a bromine or a chlorine. Alternatively, R$_1$' is a halogen chosen among a bromine, chlorine, or a fluorine. In particular, R$_1$ is H and R$_1$' is a halogen chosen among a bromine, a chlorine, or a fluorine.

Preferably, the compound has formula (I), (Ia), or (Ib) as defined above with R$_2$ being:
- a radical (C$_1$-C$_6$)alkoxy, phenoxy, said radicals being optionally substituted by at least one halogen;
- a halogen;
- a R$_4$—N—R$_5$ unit or a S—(C$_1$-C$_6$)alkyl-NR$_4$R$_5$ unit, wherein R$_4$ and R$_5$ represent H, a (C$_1$-C$_6$)alkyl group with the proviso that at least one among R$_4$ and R$_5$ is not H,
- a NHCOR$_6$ unit wherein R$_6$ represents (C$_1$-C$_6$)alkyl group,
- a radical thio-(C$_1$-C$_6$)alkyl, thio-aryl, thio-heteroaryl, thio-(C$_1$-C$_6$)alkyl-aryl, said radicals being optionally substituted by at least one halogen or by a (C$_1$-C$_6$) alkoxy group;
- an aryl group optionally substituted by at least one halogen, or a trifluoromethyl group; or
- a heteroaryl group.

More preferably, the compound has formula (I), (Ia), or (Ib) as defined above with R$_2$ being:
- a radical (C$_1$-C$_6$)alkoxy selected from the group consisting of a methoxy group, an ethoxy group and an isopropoxy group, or a phenoxy group, optionally substituted by a fluorine, such as a trifluoromethyl;
- a halogen selected from the group consisting of a fluorine and a chlorine,
- a R$_4$—N—R$_5$ unit or a S—(C$_1$-C$_6$)alkyl-NR$_4$R$_5$ unit wherein R$_4$ and R$_5$ represent a methyl or an ethyl group:
- a NHCOR$_6$ unit wherein R$_6$ represents a tert-butyl group;
- a radical selected in the group consisting of a thio-methyl group, a thio-ethyl group, a thio-benzyl group, a thio-pyridinyl group and a thio-phenyl group, optionally substituted by at least one fluorine or a trifluoromethyl group;
- a phenyl group optionally substituted by at least one bromine or a trifluoromethyl group; or
- a heteroaryl group selected from the group consisting of a furan or a triazol.

In a very particular aspect, the compound is selected from the group consisting of:
(Z)-2-(5-chloro-1H-indol-3-yl)-3-(4-chloropyridin-3-yl)-acrylonitrile;
(Z)-2-(5-bromo-1H-indol-3-yl)-3-(4-chloropyridin-3-yl)-acrylonitrile;
(Z)-2-(5-bromo-1H-indol-3-yl)-3-(4-methoxypyridin-3-yl)-acrylonitrile;
(E)-2-(5-bromo-1H-indol-3-yl)-3-(4-methoxypyridin-3-yl)-acrylonitrile;
(Z)-2-(5-chloro-1H-indol-3-yl)-3-(4-(dimethylamino)pyridin-3-yl)-acrylonitrile;
(Z)-2-(5-chloro-1H-indol-3-yl)-3-(4-dimethylamino)pyridine-3-yl)-acrylonitrile, hydrochloride;
(Z)-2-(5-bromo-1H-indol-3-yl)-3-(4-(dimethylamino)pyridin-3-yl)-acrylonitrile;
(Z)-2-(5-chloro-1H-indol-3-yl)-3-(4-methoxypyridin-3-yl)-acrylonitrile;
(E)-2-(5-chloro-1H-indol-3-yl)-3-(4-methoxypyridin-3-yl)-acrylonitrile;
(Z)-2-(5-chloro-1H-indol-3-yl)-3-(4-phenoxypyridin-3-yl)-acrylonitrile;
(Z)-2-(5-bromo-1H-indol-3-yl)-3-(4-phenoxypyridin-3-yl)-acrylonitrile;
(Z)-2-(5-methoxy-1H-indol-3-yl)-3-(4-methoxypyridin-3-yl)-acrylonitrile;
(Z)-2-(5-bromo-1H-indol-3-yl)-3-(4-ethoxypyridin-3-yl)-acrylonitrile;

(Z)-2-(5-bromo-1H-indol-3-yl)-3-(4-isopropoxypyridin-3-yl)-acrylonitrile;
(Z)-2-(5-bromo-1H-indol-3-yl)-3-(4-(methylthio)pyridin-3-yl)-acrylonitrile;
(Z)-2-(5-bromo-1H-indol-3-yl)-3-(4-(ethylthio)pyridin-3-yl)-acrylonitrile;
(Z)-2-(5-bromo-1H-indol-3-yl)-3-(4-(3-bromophenyl)pyridin-3-yl)-acrylonitrile;
(Z)-3-(4-(3-bromophenyl)pyridin-3-yl)-2-(5-chloro-1H-indol-3-yl)-acrylonitrile;
(Z)-2-(5-bromo-1H-indol-3-yl)-3-(4-(phenylthio)pyridin-3-yl)-acrylonitrile;
(Z)-3-(4-(benzylthio)pyri din-3-yl)-2-(5-bromo-1H-indol-3-yl)-acrylonitrile;
(Z)-2-(5-bromo-1H-indol-3-yl)-3-(4-(3,4-dimethoxy)thio)pyridin-3-yl)-acrylonitrile;
(Z)-2-(5-bromo-1H-indol-3-yl)-3-(4-(4-fluorophenoxy)pyridin-3-yl)-acrylonitrile;
(Z)-2-(5-chloro-1H-indol-3-yl)-3-(4-(4-fluorophenoxy)pyridin-3-yl)-acrylonitrile;
(Z)-2-(5-bromo-1H-indol-3-yl)-3-(4-(diethyl amino)pyridin-3-yl)-acrylonitrile;
(Z)-2-(5-bromo-1H-indol-3-yl)-3-(4-(4-(trifluoromethyl)phenyl)pyridin-3-yl)-acrylonitrile;
(Z)-2-(5-chloro-1H-indol-3-yl)-3-(4-(4-(trifluoromethyl)phenyl)pyridin-3-yl)-acrylonitrile;
(Z)-2-(5-chloro-1H-indol-3-yl)-3-(4-((4-fluorophenyl)thio)pyridin-3-yl)-acrylonitrile;
(Z)-2-(5-bromo-1H-indol-3-yl)-3-(4-((4-fluorophenyl)thio)pyridin-3-yl)-acrylonitrile;
(Z)-2-(5-chloro-1H-indol-3-yl)-3-(4-(furan-3-yl)pyridin-3-yl)-acrylonitrile;
(Z)-2-(5-chloro-1H-indol-3-yl)-3-(4-(pyridine-2-ylthio)pyridin-3-yl)-acrylonitrile;
(Z)-2-(5-bromo-1H-indol-3-yl)-3-(4-(pyridine-2-ylthio)pyridin-3-yl)-acrylonitrile;
(Z)-3-(4-(1H-1,2,4-triazol-1-yl)pyridin-3-yl)-2-(5-bromo-1H-indol-3-yl)-acrylonitrile;
(Z)-3-(4-(1H-1,2,4-triazol-1-yl)pyridin-3-yl)-2-(5-chloro-1H-indol-3-yl)-acrylonitrile;
(Z)-2-(5-bromo-1H-indol-3-yl)-3-(4-(furan-3-yl)pyridin-3-yl)-acrylonitrile;
(E)-2-(5-bromo-1H-indol-3-yl)-3-(4-(furan-3-yl)pyridin-3-yl)-acrylonitrile;
(Z)-2-(5-chloro-1H-indol-3-yl)-3-(4-methoxypyridin-3-yl)-acrylonitrile;
(Z)-2-(5-bromo-1H-indol-3-yl)-3-(4-(2-(dimethylamino)ethylthio)pyridin-3-yl)-acrylonitrile;
(Z)-3-(2-(5-bromo-1H-indol-3-yl)-2-cyanovinyl)-4-(4-fluorophenoxy)benzonitrile;
(Z)-3-(2-(5-bromo-1H-indol-3-yl)-2-cyanovinyl)-4-methoxybenzonitrile;
(E)-3-(2-(5-bromo-1H-indol-3-yl)-2-cyanovinyl)-4-methoxybenzonitrile;
(Z)-3-(2-(5-bromo-1H-indol-3-yl)-2-cyanovinyl)-4-(dimethylamino)benzonitrile;
(Z)-3-(2-(5-chloro-1H-indol-3-yl)-2-cyanovinyl)-4-methoxybenzonitrile;
(Z)-3-(2-(5-chloro-1H-indol-3-yl)-2-cyanovinyl)-4-(dimethylamino)benzonitrile;
(Z)-3-(2-(5-chloro-1H-indol-3-yl)-2-cyanovinyl)-4-(ethylthio)benzonitrile;
(Z)-2-(6-bromo-1H-indol-3-yl)-3-(4-methoxypyridin-3-yl)acrylonitrile;
(Z)-2-(6-fluoro-1H-indol-3-yl)-3-(4-methoxypyridin-3-yl)acrylonitrile;
(Z)-2-(6-chloro-1H-indol-3-yl)-3-(4-methoxypyridin-3-yl)acrylonitrile;
(Z)-3-(2-(5-bromo-1H-indol-3-yl)-2-cyanovinyl)-4-(furan-3-yl)pyridine-1-oxide;
(Z)-3-(2-(5-chloro-1H-indol-3-yl)-2-cyanovinyl)-4-methoxypyridine-1-oxide;
(Z)-3-(2-(5-chloro-1H-indol-3-yl)-2-cyanovinyl)-4-(trifluoromethoxy)benzonitrile;
(Z)-3-(2-(5-bromo-1H-indol-3-yl)-2-cyanovinyl)-4-(trifluoromethoxy)benzonitrile;
(Z)-3-(2-cyano-2-(6-methoxy-1H-indol-3-yl)vinyl)-4-methoxybenzonitrile;
(Z)-2-(1-acetyl-5-bromo-1H-indol-3-yl)-3-(4-methoxypyridin-3-yl)acrylonitrile;
(Z)-3-(2-(1-acetyl-5-bromo-1H-indol-3-yl)-2-cyanovinyl)-4-methoxybenzonitrile;
(Z)-2-(5-bromo-1-pivaloyl-1H-indol-3-yl)-3-(4-methoxypyridin-3-yl)acrylonitrile;
(Z)-3-(2-(5-bromo-1-pivaloyl-1H-indol-3-yl)-2-cyanovinyl)-4-methoxybenzonitrile;
(Z)-methyl 3-(5-bromo-3-(1-cyano-2-(4-methoxypyridin-3-yl)vinyl)-1H-indol-1-yl)-3-oxopropanoate;
(Z)-2-(5-bromo-1-(2-(dimethylamino)acetyl)-1H-indol-3-yl)-3-(4-methoxypyridin-3-yl)acrylonitrile:
(Z)-2-(4-methylpiperazin-1-yl)ethyl 5-bromo-3-(1-cyano-2-(4-methoxypyridin-3-yl)vinyl)-1H-indole-1-carboxylate;
((Z)-3-(2-(5-bromo-1-(2-(dimethylamino)acetyl)-1H-indol-3-yl)-2-cyanovinyl)-4-methoxybenzonitrile;
(Z)-tert-butyl 5-bromo-3-(1-cyano-2-(5-cyano-2-methoxyphenyl)vinyl)-1H-indole-1-carboxylate;
(R,Z)-benzyl-4-(5-bromo-3-(1-cyano-2-(5-cyano-2-methoxyphenyl)vinyl)-1H-indol-1-yl)-2-(tert-butoxycarbonylamino)-4-oxobutanoate;
(R,Z)-tert-butyl-5-(5-bromo-3-(1-cyano-2-(5-cyano-2-methoxyphenyl)vinyl)-1H-indol-1-yl)-2-(tert-butoxycarbonylamino)-5-oxopentanoate;
(R,Z)-benzyl-2-amino-4-(5-bromo-3-(1-cyano-2-(5-cyano-2-methoxyphenyl)vinyl)-1H-indol-1-yl)-4-oxobutanoate;
(Z)-3-(2-(5-bromo-1-(2-(4-methylpiperazin-1-yl)acetyl)-1H-indol-3-yl)-2-cyanovinyl)-4-methoxybenzonitrile;
(Z)-3-(2-(5-bromo-1-(2-(4-methylpiperazin-1-yl)acetyl)-1H-indol-3-yl)-2-cyanovinyl)-4-methoxybenzonitrile hydrochloride;
(S,Z)-3-(2-(1-(3-aminobutanoyl)-5-bromo-1H-indol-3-yl)-2-cyanovinyl)-4-methoxybenzonitrile hydrochloride;
(Z)-3-(2-(1-(2-aminoacetyl)-5-bromo-1H-indol-3-yl)-2-cyanovinyl)-4-methoxybenzonitrile hydrochloride;
(Z)-3-(2-(5-bromo-1-(2-(piperazin-1-yl)acetyl)-1H-indol-3-yl)-2-cyanovinyl)-4-methoxybenzonitrile hydrochloride;
(Z)-3-(2-(5-bromo-1-(2-(2-(2-methoxyethoxy)ethoxy)acetyl)-1H-indol-3-yl)-2-cyanovinyl)-4-methoxybenzonitrile;
(S,Z)-3-(2-(1-(2-amino-3-hydroxypropanoyl)-5-bromo-1H-indol-3-yl)-2-cyanovinyl)-4-methoxybenzonitrile hydrochloride;
(Z)-3-(2-(5-bromo-1-(5-oxopyrrolidine-2-carbonyl)-1H-indol-3-yl)-2-cyanovinyl)-4-methoxybenzonitrile;
(R,Z)-3-(2-(5-bromo-1-(2,6-diaminohexanoyl)-1H-indol-3-yl)-2-cyanovinyl)-4-methoxybenzonitrile dihydrochloride;
(Z)-3-(5-bromo-3-(1-cyano-2-(5-cyano-2-methoxyphenyl)vinyl)-1H-indol-1-yl)-3-oxopropyl dihydrogen phosphate;
and their pharmaceutically acceptable salts.

More preferably, the compound is selected from the group consisting of:

(Z)-2-(5-chloro-1H-indol-3-yl)-3-(4-chloropyridin-3-yl)-acrylonitrile;
(Z)-2-(5-bromo-1H-indol-3-yl)-3-(4-chloropyridin-3-yl)-acrylonitrile;
(Z)-2-(5-bromo-1H-indol-3-yl)-3-(4-methoxypyridin-3-yl)-acrylonitrile;
(E)-2-(5-bromo-1H-indol-3-yl)-3-(4-methoxypyridin-3-yl)-acrylonitrile;
(Z)-2-(5-chloro-1H-indol-3-yl)-3-(4-(dimethylamino)pyridin-3-yl)-acrylonitrile;
(Z)-2-(5-chloro-1H-indol-3-yl)-3-(4-dimethylamino)pyridine-3-yl)-acrylonitrile, hydrochloride;
(Z)-2-(5-bromo-1H-indol-3-yl)-3-(4-(dimethylamino)pyridin-3-yl)-acrylonitrile;
(Z)-2-(5-chloro-1H-indol-3-yl)-3-(4-methoxypyridin-3-yl)-acrylonitrile;
(E)-2-(5-chloro-1H-indol-3-yl)-3-(4-methoxypyridin-3-yl)-acrylonitrile;
(Z)-2-(5-chloro-1H-indol-3-yl)-3-(4-phenoxypyridin-3-yl)-acrylonitrile;
(Z)-2-(5-bromo-1H-indol-3-yl)-3-(4-phenoxypyridin-3-yl)-acrylonitrile;
(Z)-2-(5-methoxy-1H-indol-3-yl)-3-(4-methoxypyridin-3-yl)-acrylonitrile;
(Z)-2-(5-bromo-1H-indol-3-yl)-3-(4-ethoxypyridin-3-yl)-acrylonitrile;
(Z)-2-(5-bromo-1H-indol-3-yl)-3-(4-isopropoxypyridin-3-yl)-acrylonitrile;
(Z)-2-(5-bromo-1H-indol-3-yl)-3-(4-(methylthio)pyridin-3-yl)-acrylonitrile;
(Z)-2-(5-bromo-1H-indol-3-yl)-3-(4-(ethylthio)pyridin-3-yl)-acrylonitrile;
(Z)-2-(5-bromo-1H-indol-3-yl)-3-(4-(3-bromophenyl)pyridin-3-yl)-acrylonitrile;
(Z)-3-(4-(3-bromophenyl)pyridin-3-yl)-2-(5-chloro-1H-indol-3-yl)-acrylonitrile;
(Z)-2-(5-bromo-1H-indol-3-yl)-3-(4-(phenylthio)pyridin-3-yl)-acrylonitrile;
(Z)-3-(4-(benzylthio)pyridin-3-yl)-2-(5-bromo-1H-indol-3-yl)-acrylonitrile;
(Z)-2-(5-bromo-1H-indol-3-yl)-3-(4-(3,4-dimethoxy)thio)pyridin-3-yl)-acrylonitrile;
(Z)-2-(5-bromo-1H-indol-3-yl)-3-(4-(4-fluorophenoxy)pyridin-3-yl)-acrylonitrile;
(Z)-2-(5-chloro-1H-indol-3-yl)-3-(4-(4-fluorophenoxy)pyridin-3-yl)-acrylonitrile;
(Z)-2-(5-bromo-1H-indol-3-yl)-3-(4-(diethylamino)pyridin-3-yl)-acrylonitrile;
(Z)-2-(5-bromo-1H-indol-3-yl)-3-(4-(4-(trifluoromethyl)phenyl)pyridin-3-yl)-acrylonitrile;
(Z)-2-(5-chloro-1H-indol-3-yl)-3-(4-(4-(trifluoromethyl)phenyl)pyridin-3-yl)-acrylonitrile;
(Z)-2-(5-chloro-1H-indol-3-yl)-3-(4-((4-fluorophenyl)thio)pyridin-3-yl)-acrylonitrile;
(Z)-2-(5-bromo-1H-indol-3-yl)-3-(4-((4-fluorophenyl)thio)pyridin-3-yl)-acrylonitrile;
(Z)-2-(5-chloro-1H-indol-3-yl)-3-(4-(furan-3-yl)pyridin-3-yl)-acrylonitrile;
(Z)-2-(5-chloro-1H-indol-3-yl)-3-(4-(pyridine-2-ylthio)pyridin-3-yl)-acrylonitrile;
(Z)-2-(5-bromo-1H-indol-3-yl)-3-(4-(pyridine-2-ylthio)pyridin-3-yl)-acrylonitrile;
(Z)-3-(4-(1H-1,2,4-triazol-1-yl)pyridin-3-yl)-2-(5-bromo-1H-indol-3-yl)-acrylonitrile;
(Z)-3-(4-(1H-1,2,4-triazol-1-yl)pyridin-3-yl)-2-(5-chloro-1H-indol-3-yl)-acrylonitrile;
(Z)-2-(5-bromo-1H-indol-3-yl)-3-(4-(furan-3-yl)pyridin-3-yl)-acrylonitrile;
(E)-2-(5-bromo-1H-indol-3-yl)-3-(4-(furan-3-yl)pyridin-3-yl)-acrylonitrile;
(Z)-2-(5-chloro-1H-indol-3-yl)-3-(4-methoxypyridin-3-yl)-acrylonitrile;
(Z)-2-(5-bromo-1H-indol-3-yl)-3-(4-(2-(dimethylamino)ethylthio)pyridin-3-yl)-acrylonitrile;
(Z)-3-(2-(5-bromo-1H-indol-3-yl)-2-cyanovinyl)-4-(4-fluorophenoxy)benzonitrile;
(Z)-3-(2-(5-bromo-1H-indol-3-yl)-2-cyanovinyl)-4-methoxybenzonitrile;
(E)-3-(2-(5-bromo-1H-indol-3-yl)-2-cyanovinyl)-4-methoxybenzonitrile;
(Z)-3-(2-(5-bromo-1H-indol-3-yl)-2-cyanovinyl)-4-(dimethylamino)benzonitrile;
(Z)-3-(2-(5-chloro-1H-indol-3-yl)-2-cyanovinyl)-4-methoxybenzonitrile;
(Z)-3-(2-(5-chloro-1H-indol-3-yl)-2-cyanovinyl)-4-(dimethylamino)benzonitrile;
(Z)-3-(2-(5-chloro-1H-indol-3-yl)-2-cyanovinyl)-4-(ethylthio)benzonitrile;
(Z)-2-(6-bromo-1H-indol-3-yl)-3-(4-methoxypyridin-3-yl)acrylonitrile;
(Z)-2-(6-fluoro-1H-indol-3-yl)-3-(4-methoxypyridin-3-yl)acrylonitrile;
(Z)-2-(6-chloro-1H-indol-3-yl)-3-(4-methoxypyridin-3-yl)acrylonitrile;
(Z)-3-(2-(5-bromo-1H-indol-3-yl)-2-cyanovinyl)-4-(furan-3-yl)pyridine-1-oxide;
(Z)-3-(2-(5-chloro-1H-indol-3-yl)-2-cyanovinyl)-4-methoxypyridine-1-oxide;
(Z)-3-(2-(5-chloro-1H-indol-3-yl)-2-cyanovinyl)-4-(trifluoromethoxy)benzonitrile;
(Z)-3-(2-(5-bromo-1H-indol-3-yl)-2-cyanovinyl)-4-(trifluoromethoxy)benzonitrile;
(Z)-3-(2-cyano-2-(6-methoxy-1H-indol-3-yl)vinyl)-4-methoxybenzonitrile;
and their pharmaceutically acceptable salts.

Even more preferably, the compound is selected from the group consisting of:
(Z)-2-(5-chloro-1H-indol-3-yl)-3-(4-chloropyridin-3-yl)-acrylonitrile;
(Z)-2-(5-bromo-1H-indol-3-yl)-3-(4-chloropyridin-3-yl)-acrylonitrile;
(Z)-2-(5-bromo-1H-indol-3-yl)-3-(4-methoxypyridin-3-yl)-acrylonitrile;
(E)-2-(5-bromo-1H-indol-3-yl)-3-(4-methoxypyridin-3-yl)-acrylonitrile;
(Z)-2-(5-chloro-1H-indol-3-yl)-3-(4-methoxypyridin-3-yl)-acrylonitrile;
(E)-2-(5-chloro-1H-indol-3-yl)-3-(4-methoxypyridin-3-yl)-acrylonitrile;
(Z)-2-(5-methoxy-1H-indol-3-yl)-3-(4-methoxypyridin-3-yl)-acrylonitrile;
(Z)-2-(5-bromo-1H-indol-3-yl)-3-(4-ethoxypyridin-3-yl)-acrylonitrile;
(Z)-2-(5-bromo-1H-indol-3-yl)-3-(4-isopropoxypyridin-3-yl)-acrylonitrile;
(Z)-2-(5-bromo-1H-indol-3-yl)-3-(4-(methylthio)-pyridin-3-yl)-acrylonitrile;
(Z)-2-(5-bromo-1H-indol-3-yl)-3-(4-(phenylthio)pyridin-3-yl)-acrylonitrile;
(Z)-3-(4-(benzylthio)pyridin-3-yl)-2-(5-bromo-1H-indol-3-yl)-acrylonitrile;
(Z)-2-(5-bromo-1H-indol-3-yl)-3-(4-(4-fluorophenoxy)pyridin-3-yl)-acrylonitrile;

(Z)-2-(5-chloro-1H-indol-3-yl)-3-(4-(4-fluorophenoxy)
pyridin-3-yl)-acrylonitrile;
(Z)-2-(5-bromo-1H-indol-3-yl)-3-(4-(dimethylamino)pyridin-3-yl)-acrylonitrile;
(Z)-2-(5-bromo-1H-indol-3-yl)-3-(4-(diethylamino)pyridin-3-yl)-acrylonitrile;
(Z)-2-(5-bromo-1H-indol-3-yl)-3-(4-(4-(trifluoromethyl)
phenyl)pyridin-3-yl)-acrylonitrile;
(Z)-2-(5-chloro-1H-indol-3-yl)-3-(4-((4-fluorophenyl)thio)
pyridin-3-yl)-acrylonitrile;
(Z)-2-(5-bromo-1H-indol-3-yl)-3-(4-((4-fluorophenyl)thio)
pyridin-3-yl)-acrylonitrile;
(Z)-2-(5-chloro-1H-indol-3-yl)-3-(4-(furan-3-yl)pyridin-3-yl)-acrylonitrile;
(Z)-2-(5-chloro-1H-indol-3-yl)-3-(4-(pyridine-2-ylthio)
pyridin-3-yl)-acrylonitrile;
(Z)-3-(4-(1H-1,2,4-triazol-1-yl)pyridin-3-yl)-2-(5-bromo-1H-indol-3-yl)-acrylonitrile;
(Z)-3-(4-(1H-1,2,4-triazol-1-yl)pyridin-3-yl)-2-(5-chloro-1H-indol-3-yl)-acrylonitrile;
(Z)-2-(5-bromo-1H-indol-3-yl)-3-(4-(furan-3-yl)pyridin-3-yl)-acrylonitrile;
(E)-2-(5-bromo-1H-indol-3-yl)-3-(4-(furan-3-yl)pyridin-3-yl)-acrylonitrile;
(Z)-2-(5-chloro-1H-indol-3-yl)-3-(4-methoxypyridin-3-yl)-acrylonitrile;
(Z)-3-(2-(5-bromo-1H-indol-3-yl)-2-cyanovinyl)-4-methoxybenzonitrile;
(E)-3-(2-(5-bromo-1H-indol-3-yl)-2-cyanovinyl)-4-methoxybenzonitrile;
(Z)-3-(2-(5-bromo-1H-indol-3-yl)-2-cyanovinyl)-4-(dimethylamino)benzonitrile;
(Z)-2-(6-bromo-1H-indol-3-yl)-3-(4-methoxypyridin-3-yl)
acrylonitrile;
(Z)-2-(6-fluoro-1H-indol-3-yl)-3-(4-methoxypyridin-3-yl)
acrylonitrile;
(Z)-2-(6-chloro-1H-indol-3-yl)-3-(4-methoxypyridin-3-yl)
acrylonitrile;
(Z)-3-(2-(5-bromo-1H-indol-3-yl)-2-cyanovinyl)-4-(furan-3-yl)pyridine-1-oxide;
(Z)-3-(2-(5-chloro-1H-indol-3-yl)-2-cyanovinyl)-4-methoxypyridine-1-oxide;
(Z)-3-(2-(5-chloro-1H-indol-3-yl)-2-cyanovinyl)-4-(trifluoromethoxy)benzonitrile;
(Z)-3-(2-(5-bromo-1H-indol-3-yl)-2-cyanovinyl)-4-(trifluoromethoxy)benzonitrile;
and their pharmaceutically acceptable salts. The present invention also relates to a compound of the formula (I) as defined above or (Z)-3-(4-ethoxypyridin-3-yl)-2-(5-methoxy-1H-indol-3-yl)-acrylonitrile for use as a drug.

The present invention further relates to a pharmaceutical composition comprising as an active ingredient one compound of the formula (I) as defined above or (Z)-3-(4-ethoxypyridin-3-yl)-2-(5-methoxy-1H-indol-3-yl)-acrylonitrile.

Preferably, the pharmaceutical composition of the present invention is for use in the treatment of cancer.

Optionally, the pharmaceutical composition of the present invention further comprises an additional antitumoral drug, preferably selected from the group consisting of an inhibitor of topoisomerases I or II, a DNA alkylating agent, an anti-metabolic agent, a targeted agent such as a kinase inhibitor, and/or a therapeutical antibody designed to mediate cytotoxicity against the cancer cells or to modulate one of their key biological functions.

More preferably, the pharmaceutical composition of the present invention is for use for treating cancer in combination with radiotherapy, hyperthermia, surgery (e.g., tumor resection) and/or other antitumoral therapies or before, simultaneously or after surgery (e.g., tumor resection).

In addition, the present invention relates to a kit comprising (a) a compound of the present invention; and (b) an additional antitumoral drug as a combined preparation for simultaneous, separate or sequential use, in particular in the treatment of cancer.

Advantageously, the pharmaceutical composition of the present invention is for use in the treatment of viral infections, particularly, HIV infection, HTLV infection or HPV infection.

More advantageously, the pharmaceutical composition of the present invention is for use in the treatment of lung diseases, particularly the treatment of pulmonary hypertension.

More advantageously, the pharmaceutical composition of the present invention is for use in the treatment of pathologies associated with dysregulation of MKlp2 or for use in the treatment of pathologies in which the MKlp2 pathway is dysregulated.

The present invention also concerns the use of a compound of the formula (I) as defined above as a research pharmacological tool.

DETAILED DESCRIPTION OF THE INVENTION

The inventors identified a new class of derivatives of indoles of the formula (I):

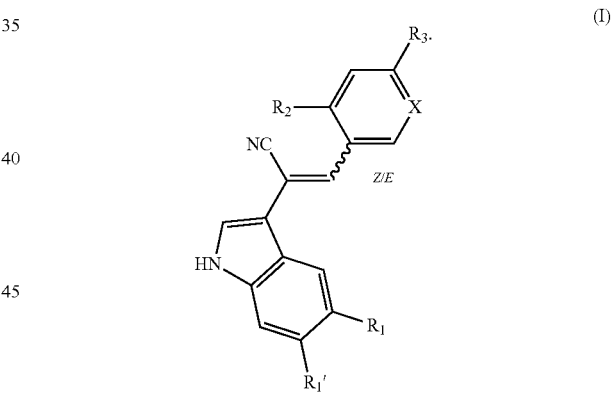

This new class of compounds presents a therapeutic interest, in particular as effective inhibitors of MKlp2, and consequently, can be used as a drug, for instance for treating cancer, viral infections, lung diseases or pathologies associated with dysregulation of MKlp2 or its pathway.

The inventors, surprisingly, discovered that compounds both substituted in $R_1$ and $R_2$ leads to greater MKlp2 inhibition compared to the compounds disclosed in patent application WO 2010/150211.

In particular, a better MKlp2 inhibition profile is surprisingly observed with compounds of the formula (I) of the present invention, wherein $R_1$ or $R_1'$ represents a $(C_1$-$C_3)$-alkoxy group or a halogen while $R_2$ substituent is present and distinct from a $C_1$-$C_3$ alkyl group.

Accordingly, the present invention relates to compound of formula (I):

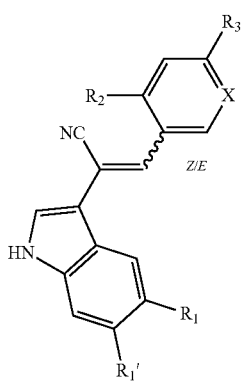

(I)

wherein:
- X represents a nitrogen atom, a C—CN unit or a $N^+$—$O^-$ unit, preferably a nitrogen atom or a C—CN unit;
- $R_1$ and $R_1'$ are such that one is H and the other represents a halogen or a ($C_1$-$C_6$)alkoxy group, optionally substituted by a carboxylic group or one —$NR_{11}R_{12}$ unit wherein $R_{11}$ and $R_{12}$ represent H or a ($C_1$-$C_6$)alkyl group or $R_{11}$ and $R_{12}$ taken together form a 3- to 7-membered ring optionally interrupted by one or several heteroatoms;
- $R_2$ represents:
  - a radical ($C_1$-$C_6$)alkoxy, ($C_3$-$C_6$)cycloalkoxy, aryloxy, heteroaryloxy, ($C_1$-$C_6$)alkyl-aryloxy, ($C_1$-$C_6$)alkyl-heteroaryloxy, said radicals being optionally substituted by at least one halogen,
  - a hydroxy,
  - a halogen,
  - a —$NR_4R_5$ unit, a O—($C_1$-$C_6$)alkyl-$NR_4R_5$ unit or a S—($C_1$-$C_6$)alkyl-$NR_4R_5$ unit wherein $R_4$ and $R_5$ represent H or a ($C_1$-$C_6$)alkyl group, or $R_4$ and $R_5$ taken together form a 3- to 7-membered ring, optionally interrupted by one or several heteroatoms, with the proviso that at least one among $R_4$ and $R_5$ is not H,
  - a $NHCOR_6$ unit wherein $R_6$ represents ($C_1$-$C_6$)alkyl group,
  - a radical thio-($C_1$-$C_6$)alkyl, thio-aryl, thio-heteroaryl, thio-($C_1$-$C_6$)alkyl-aryl or thio-($C_1$-$C_6$)-alkyl-heteroaryl, said radicals being optionally substituted by at least one halogen or by a ($C_1$-$C_6$)alkoxy group,
  - an aryl group optionally substituted by at least one halogen, a trifluoromethyl group, or a ($C_1$-$C_3$)alkoxy group, or
  - a heteroaryl group, eventually substituted by a halogen, a trifluoromethyl group or a ($C_1$-$C_3$)alkoxy group, with the proviso that if $R_1$ or $R_1'$ is a ($C_1$-$C_3$)alkoxy group, then $R_2$ is not a halogen; and
- $R_3$ represents a hydrogen, a ($C_1$-$C_3$)alkyl group, a ($C_1$-$C_3$)alkoxy group or a halogen, advantageously a fluorine;

or one of its pharmaceutically acceptable salts.

In a preferred embodiment, the compound of formula (I) is not (Z)-3-(4-ethoxypyridin-3-yl)-2-(5-methoxy-1H-indol-3-yl)-acrylonitrile. In an alternative embodiment, the compound of formula (I) is such that $R_2$ is not an ethoxy group.

In a particular embodiment, when $R_1$ or $R_1'$ is a ($C_1$-$C_6$) alkoxy group, optionally substituted by one $R_{11}$—N—$R_{12}$ unit as above defined or a carboxylic group, then $R_2$ is not a halogen the compound of formula (I).

In a preferred embodiment, $R_1$ and $R_1'$ are such that one represents a halogen or a ($C_1$-$C_3$)alkoxy group, optionally substituted by a carboxylic group or one $R_{11}$—N—$R_{12}$ unit as above defined. In a more preferred embodiment, $R_1$ and $R_1'$ are such that one represents a halogen or a ($C_1$-$C_3$)alkoxy group.

The present invention also relates to prodrugs of the compounds disclosed in the present application, preferably prodrugs in which the nitrogen atom of the indole core is substituted. According, the present invention relates to prodrugs in which the nitrogen atom of the indole core is substituted by a group selected from the group consisting of a $COR_7$ and a $CO_2R_7$ group, wherein $R_7$ represents:
- a ($C_1$-$C_6$)alkyl group, optionally substituted by at least a hydroxy group, a ($C_1$-$C_6$)alkyloxy group, a ($C_1$-$C_6$)$_n$ polyalkyloxy group wherein n is 1<n<6, a phosphate or pyrophosphate group and salts or ($C_1$-$C_3$)alkyl ester thereof, a $R_8$ group, a —$NHCO_2R_8$ unit, a $COR_8$ group, or a $CO_2R_8$ group, wherein $R_8$ is:
  - a ($C_1$-$C_6$)alkyl group,
  - an aryl, a ($C_1$-$C_6$)alkylaryl, or a heteroaryl,
  - a $NR_9R_{10}$ unit wherein $R_9$ and $R_{10}$ represent a hydrogen, a ($C_1$-$C_6$)alkyl group, or $R_9$ and $R_{10}$ taken together form a 3- to 7-membered ring, optionally interrupted by one or several heteroatoms, and optionally the ring being substituted by at least one ($C_1$-$C_6$)alkyl group;
- a NH—$NR_9R_{10}$ unit wherein $R_9$ and $R_{10}$ are such as defined above; or
- a saturated heterocycle or a heteroaryl.

In a particular embodiment, the present invention relates to compounds of formula (Ia):

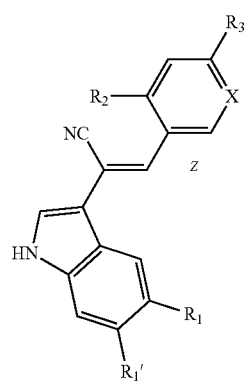

(Ia)

wherein X, $R_1$, $R_1'$, $R_2$, $R_3$, $R_4$, $R_5$ and $R_6$ are such as defined above. It also relates to prodrugs thereof as defined in the present document.

In another particular embodiment, the present invention relates to compounds of formula (Ib):

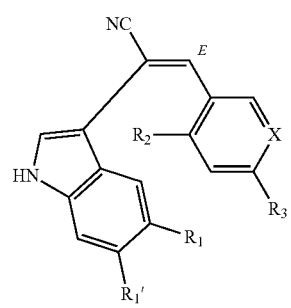

(Ib)

wherein X, $R_1$, $R_1'$, $R_2$, $R_3$, $R_4$, $R_5$ and $R_6$ are such as defined above. It also relates to prodrugs thereof as defined in the present document.

In another particular embodiment, the present invention relates to compounds of formula (II):

(II)

wherein X, $R_1$, $R_1'$, $R_2$, $R_3$, $R_4$, $R_5$ and $R_6$ are such as defined above, and $R_a$ is a group selected from the group consisting of a $COR_7$ and a $CO_2R_7$ group, wherein $R_7$ represents:
- a $(C_1-C_6)$alkyl group, optionally substituted by at least a hydroxy group, a $(C_1-C_6)$alkyloxy group, a $(C_1-C_6)_n$ polyalkyloxy group wherein n is 1<n<6, a phosphate or pyrophosphate group and salts or $(C_1-C_3)$alkyl ester thereof, a $R_8$ group, a —$NHCO_2R_8$ unit, a $COR_8$ group, or a $CO_2R_8$ group, wherein $R_8$ is:
  - a $(C_1-C_6)$alkyl group,
  - an aryl, a $(C_1-C_6)$alkylaryl, or a heteroaryl,
  - a $NR_9R_{10}$ unit wherein $R_9$ and $R_{10}$ represent a hydrogen, a $(C_1-C_6)$alkyl group, or $R_9$ and $R_1$ taken together form a 3- to 7-membered ring, optionally interrupted by one or several heteroatoms, and optionally the ring being substituted by at least one $(C_1-C_6)$alkyl group;
  - a NH—$NR_9R_{10}$ unit wherein $R_9$ and $R_{10}$ are such as defined above; or
  - a saturated heterocycle or a heteroaryl;
or one of its pharmaceutically acceptable salts.

According to the present invention, the terms below have the following meanings:

The terms mentioned herein with prefixes such as for example $C_1-C_3$ or $C_1-C_6$ can also be used with lower numbers of carbon atoms such as $C_1-C_2$ or $C_1-C_5$. If, for example, the term $C_1-C_3$ is used, it means that the corresponding hydrocarbon chain may comprise from 1 to 3 carbon atoms, especially 1, 2 or 3 carbon atoms. If, for example, the term $C_1-C_6$ is used, it means that the corresponding hydrocarbon chain may comprise from 1 to 6 carbon atoms, especially 1, 2, 3, 4, 5 or 6 carbon atoms.

The term "alkyl" refers to a saturated, linear or branched aliphatic group. The term "$(C_1-C_3)$alkyl" more specifically means methyl (also called "Me"), ethyl (also called "Et"), propyl, or isopropyl, the term "$(C_1-C_6)$alkyl" more specifically means methyl, ethyl, propyl, isopropyl, butyl, isobutyl, tert-butyl or propyl, pentyl or hexyl.

The term "halogen" corresponds to a fluorine, chlorine, bromine, or iodine atom, preferably a fluorine, chlorine or bromine, and more preferably a chlorine or a bromine.

The term "alkoxy" or "alkyloxy" corresponds to the alkyl group defined hereinabove bonded to the molecule by an —O— (ether) bond. $(C_1-C_3)$alkoxy includes methoxy, ethoxy, propyloxy, and isopropyloxy. $(C_1-C_6)$alkoxy includes methoxy, ethoxy, propyloxy, isopropyloxy, butyloxy, isobutyloxy, tert-butyloxy, pentyloxy and hexyloxy.

The term $(C_1-C_6)_n$polyalkyloxy corresponds to n $(C_1-C_6)$ alkyloxy bounded thereby forming a linear poly($C_1-C_6$) alkylene glycol chain, preferably a linear polyethylene glycol chain. Preferably, n is 1<n<6.

The term "thio" corresponds to the alkyl group defined hereinabove bounded to the molecule by a —S— (thioether) bound. Thio-$(C_1-C_6)$alkyl group includes thio-methyl, thio-ethyl, thio-propyl, thio-butyl, thio-pentyl and thio-hexyl.

The term "aryl" is mono- or bi-cyclic aromatic hydrocarbons having from 6 to 12 carbon atoms, optionally substituted. Aryl may be a phenyl (also called "Ph"), biphenyl or naphthyl. In a preferred embodiment, the aryl is a phenyl.

The term "heteroaryl" as used herein corresponds to an aromatic, mono- or poly-cyclic group comprising between 5 and 14 atoms and comprising at least one heteroatom such as nitrogen, oxygen or sulphur atom. Examples of such mono- and poly-cyclic heteroaryl group may be: pyridyl, dihydroypyridyl, thiazolyl, thiophenyl, furanyl, azocinyl, pyranyl, pyrrolyl, pyrazolyl, imidazolyl, triazolyl, tetrazolyl, benzofuranyl, thianaphthalenyl, indolyl, indolenyl, quinolinyl, isoquinolinyl, benzimidazolyl, pyrrolinyl, tetrahydroquinolinyl, tetrahydroisoquinolinyl, triazinyl, 6H-1,2,5-thiadiazinyl, 2H,6H-1,5,2-dithiazinyl, thianthrenyl, isobenzofuranyl, chromenyl, xanthenyl, phenoxanthinyl, 2H-pyrrolyl, isothiazolyl, isoxazolyl, pyrazinyl, pyridazinyl, indolizinyl, isoindolyl, 3H-indolyl, 1-Hindazolyl, purinyl, 4H-quinolizinyl, phtalazinyl, naphthyridinyl, quinoxalinyl, quinazolinyl, cinnolinyl, pteridinyl, 4aH-carbazolyl, carbazolyl, O-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, indolinyl, isoindolinyl, oxazolidinyl, benzotriazolyl, benzisoxazolyl, oxindolyl, benzoxazolinyl, benzothienyl, benzothiazolyl, isatinyl, dihydropyridyl, pyrimidinyl, pyrazinyl, s-triazinyl, oxazolyl, thiofuranyl. In a preferred embodiment, heteroaryl is an aromatic monocyclic comprising 5 or 6 atoms and comprising at least one heteroatom such as nitrogen, oxygen or sulphur atom. Preferably, heteroaryl is pyridyl, thiazolyl, furanyl, pyranyl, pyrrolyl, imidazolyl, tetrazolyl, benzofuranyl, pyrrolinyl, triazinyl, pyrazinyl, pyridazinyl, triazolyl or tetrazolyl. More preferably, heteroaryl is furanyl or triazolyl.

$(C_3-C_6)$cycloalkoxy includes cyclopropoxy, cyclobutoxy, cyclopentoxy and cyclohexoxy, $(C_3-C_6)$cycloalkyl includes cyclopropyl, cyclobutyl, cyclopentyl and cyclohexyl.

The term "saturated heterocycle" as used herein corresponds to a non-aromatic mono- or poly-cyclic group comprising between 5 and 14 atoms and comprising at least one heteroatom such as nitrogen, oxygen or sulphur atom. Examples of such heterocycle may be cyclohexanyl, tetrahydrofuranyl, pyrrolidinyl, piperidinyl, dioxanyl, morpholinyl, piperazinyl.

Particularly, the saturated heterocycle may be substituted, for instance by a ketone. More preferably, the saturated heterocycle is oxopyrrolidinyl.

The expression "substituted by at least" means that the radical is substituted by one or several groups of the list.

By "$R_x$—N—$R_y$" is intended to refer to a unit "—$NR_xR_y$".

The terms "carboxylic" "Boc" and "Cbz" respectively correspond to the following groups "—COOH", "—C(=O)—O—C(CH$_3$)$_3$" and "—C(=O)—O—CH$_2$.Phenyl".

The expression "with the proviso that if $R_1$ or $R_1'$ is a ($C_1$-$C_3$)alkoxy group, then $R_2$ is not a halogen" or "with the proviso that if $R_1$ or $R_1'$ is a ($C_1$-$C_6$)alkoxy group optionally substituted by one $R_{11}$—N—$R_{12}$ unit as above defined or a carboxylic group, then $R_2$ is not a halogen" means that, when $R_1$ or $R_1'$ is a ($C_1$-$C_3$)alkoxy group or when $R_1$ or $R_1'$ is a ($C_1$-$C_6$)alkoxy group, optionally substituted by one $R_{11}$—N—$R_{12}$ unit or a carboxylic group, as above defined, $R_2$ represents:

- a radical ($C_1$-$C_6$)alkoxy, ($C_3$-$C_6$)cycloalkoxy, aryloxy, heteroaryloxy, ($C_1$-$C_6$)alkyl-aryloxy, ($C_1$-$C_6$)alkyl-heteroaryloxy, said radicals being optionally substituted by at least one halogen,
- a $R_4$—N—$R_5$ unit, a O—($C_1$-$C_6$)alkyl-$NR_4R_5$ unit or a S—($C_1$-$C_6$)alkyl-$NR_4R_5$ unit wherein $R_4$ and $R_5$ represent H, or a ($C_1$-$C_6$)alkyl group, or $R_4$ and $R_5$ taken together form a 3- to 7-membered ring, optionally interrupted by one or several heteroatoms, with the proviso that at least one among $R_4$ and $R_5$ is not H,
- a $NHCOR_6$ unit wherein $R_6$ represents ($C_1$-$C_6$)alkyl group,
- a radical thio-($C_1$-$C_6$)alkyl, thio-aryl, thio-heteroaryl, thio-($C_1$-$C_6$)alkyl-aryl or thio-($C_1$-$C_6$)-alkyl-heteroaryl, said radicals being optionally substituted by at least one halogen or by a ($C_1$-$C_6$)alkoxy group,
- an aryl group optionally substituted by at least one halogen, a trifluoromethyl group, or a ($C_1$-$C_3$)alkoxy group, or
- a heteroaryl group, eventually substituted by a halogen, a trifluoromethyl group or a ($C_1$-$C_3$)alkoxy group.

The pharmaceutically acceptable salts include inorganic as well as organic acids salts. Representative examples of suitable inorganic acids include hydrochloric, hydrobromic, hydroiodic, phosphoric, and the like. Representative examples of suitable organic acids include formic, acetic, trichloroacetic, trifluoroacetic, propionic, benzoic, cinnamic, citric, fumaric, maleic, methanesulfonic and the like. Further examples of pharmaceutically acceptable inorganic or organic acid addition salts include the pharmaceutically acceptable salts listed in J. Pharm. Sci. 1977, 66, 2, and in Handbook of Pharmaceutical Salts: Properties, Selection, and Use edited by P. Heinrich Stahl and Camille G. Wermuth 2002. In a preferred embodiment, the salt is selected from the group consisting of maleate, chlorhydrate, bromhydrate, and methanesulfonate.

$R_1$ and $R_1'$ are such that one is H and the other represents a halogen or a ($C_1$-$C_6$)alkoxy group, optionally substituted by one $R_{11}$—N—$R_{12}$ unit as above defined, or a carboxylic group. Preferably, $R_1'$ or $R_1$ represents a halogen, typically, a bromine, a chlorine or a fluorine, advantageously a bromine or a chlorine, more specifically a bromine. Alternatively, $R_1'$ or $R_1$ represent a ($C_1$-$C_6$)alkoxy group optionally substituted by one $R_{11}$—N—$R_{12}$ unit as above defined or a carboxylic group, preferably a ($C_1$-$C_3$)alkoxy group optionally substituted by one $R_{11}$—N—$R_{12}$ unit as above defined or a carboxylic group, more preferably a ($C_1$-$C_3$)alkoxy group, advantageously a methoxy, an ethoxy or an isopropoxy, more advantageously a methoxy. $R_{11}$ and $R_{12}$ are such as defined above and preferably represent a ($C_1$-$C_3$) alkyl group, and more preferably, a methyl or an ethyl group.

In a preferred embodiment, $R_1'$ is H. In another preferred embodiment, $R_1'$ is a halogen chosen among a bromine, a chlorine, or a fluorine, and $R_1$ is H.

Particularly, $R_2$ represents:
- a radical ($C_1$-$C_6$)alkoxy or phenoxy, said radicals being optionally substituted by at least one halogen, preferably a bromine, a chlorine or a fluorine, more preferably a fluorine, such as a trifluoromethyl;
- a halogen, preferably a bromine, a chlorine, or a fluorine, more preferably a bromine or a chlorine;
- a $R_4$—N—$R_5$ unit or a S—($C_1$-$C_6$)alkyl-$NR_4R_5$ unit, wherein $R_4$ and $R_5$ represent H or a ($C_1$-$C_6$)alkyl group, with the proviso that at least one among $R_4$ and $R_5$ is not H,
- a $NHCOR_6$ unit wherein $R_6$ represents ($C_1$-$C_6$)alkyl group, advantageously a methyl, an ethyl or a tert-butyl;
- a radical thio-($C_1$-$C_6$)alkyl, thio-aryl, thio-heteroaryl, thio-($C_1$-$C_6$)alkyl-aryl, said radicals being optionally substituted by at least one halogen, a trifluoromethyl, or by a ($C_1$-$C_6$)alkoxy group;
- an aryl group optionally substituted by at least one halogen, or a trifluoromethyl group; or
- a heteroaryl group, advantageously a furan, a triazol, a pyridin, a thiazol, a pyran, a pyrrol, an imidazol, a tetrazol, a benzofuran, triazinyl, pyrazinyl, a pyridazin, or a tetrazol.

In a particular embodiment in which $R_2$ represents a radical ($C_1$-$C_6$)alkoxy, the radical ($C_1$-$C_6$)alkoxy is selected from the group consisting of a methoxy, propoxy, butoxy, pentoxy and hexoxy.

Preferably, $R_2$ represents:
- a radical ($C_1$-$C_6$)alkoxy selected from the group consisting of a methoxy group, an ethoxy group, and an isopropoxy group, preferably selected from the group consisting of a methoxy group, and an isopropoxy group, or a phenoxy group, optionally substituted by a fluorine, such as a trifluoromethyl;
- a halogen selected from the group consisting of a fluorine and a chlorine,
- a $R_4$—N—$R_5$ unit or a S—($C_1$-$C_6$)alkyl-$NR_4R_5$ unit wherein $R_4$ and $R_5$ represent a methyl or an ethyl group:
- a radical selected from the group consisting of a thio-methyl group, a thio-ethyl group, a thio-benzyl group, a thio-pyridinyl group and a thio-phenyl group, optionally substituted by at least one fluorine or a trifluoromethyl group;
- a phenyl group optionally substituted by at least one bromine or a trifluoromethyl group; or
- a heteroaryl group selected from the group consisting of a furan or a triazol.

Particularly, $R_3$ represents a hydrogen; a ($C_1$-$C_3$)alkyl group, preferably a methyl, an ethyl or an isopropyl; a ($C_1$-$C_3$)alkoxy group, preferably a methoxy, an ethoxy or an isopropoxy; or a halogene, advantageously a fluorine. Preferably, $R_3$ is H, methoxy or fluorine. More preferably, $R_3$ is H.

In a particular embodiment of the invention:
- $R_1'$ or $R_1$ represents a halogen, typically a bromine, a chlorine or a fluorine, advantageously a bromine or a chlorine, more specifically a bromine. In a particular embodiment, $R_1'$ is H. Alternatively $R_1'$ is a halogen chosen among a bromine, a chlorine, or a fluorine, and $R_1$ is H.
- $R_2$ represents:
  - a radical ($C_1$-$C_6$)alkoxy, preferably a methoxy, an ethoxy, or an isopropoxy, more preferably a methoxy, or isopropoxy group, and a phenoxy optionally substituted by a fluorine, such as a trifluoromethyl; or
  - a halogen, advantageously a fluorine and a chlorine, more advantageously a chlorine; or
  - a $R_4$—N—$R_5$ unit or a S—($C_1$-$C_6$)alkyl-$NR_4R_5$ unit wherein $R_4$ and $R_5$ represent a ($C_1$-$C_6$)alkyl group, preferably a methyl or an ethyl group; or a radical thio-$(C_1-C_6)$alkyl, preferably a thio-methyl or a thio-ethyl; a radical thio-aryl, preferably a thio-phenyl; a radical thio-heteroaryl, preferably, a thio-pyridinyl; or a radical thio-$(C_1-C_6)$alkyl-aryl, preferably a thio-benzyl; said radicals being optionally substituted by at least a halogen, preferably a fluorine, a trifluoromethyl, or by a $(C_1-C_6)$alkoxy group, preferably a methoxy, ethoxy, isopropoxy, more preferably a methoxy;

a phenyl group optionally substituted by at least one halogene, preferably a bromine, or a trifluoromethyl group; or a heteroaryl group, preferably a furan, a triazol, a pyridin, a thiazol, a pyran, a pyrrol, an imidazol, a benzofuran, a triazol, or a tetrazol, and more preferably a furan or a triazol; and optionally, $R_3$ represents a hydrogen or a $(C_1-C_3)$alkyl group, preferably a methyl, an ethyl or an isopropyl; a $(C_1-C_3)$ alkoxy group, preferably a methoxy, an ethoxy or an isopropoxy; or a halogen, advantageously a fluorine. Preferably, $R_3$ is H, methoxy or fluorine. More preferably, $R_3$ is H.

In another particular embodiment of the invention:

$R_1'$ or $R_1$ represents a $(C_1-C_6)$alkoxy group optionally substituted by one $R_{11}$—N—$R_{12}$ unit as above defined or a carboxylic group, preferably a $(C_1-C_3)$alkoxy group optionally substituted by one $R_{11}$—N—$R_{12}$ unit as above defined, preferably wherein $R_4$ and $R_5$ represent a $(C_1-C_3)$alkyl group and more preferably a methyl or an ethyl group, or carboxylic group, more preferably a $(C_1-C_3)$alkoxy group, still more preferably a methoxy. Advantageously, $R_1'$ is H. Alternatively $R_1'$ is a halogen chosen among a bromine, a chlorine, or a fluorine, and $R_1$ is H. Optionally, $R_1'$ is a methoxy and $R_1$ is H.

$R_2$ represents:

a radical $(C_1-C_6)$alkoxy, preferably a methoxy, an ethoxy or an isopropoxy, more preferably a methoxy or an ethoxy, still more preferably a methoxy; or a phenoxy group, optionally substituted by a fluorine, such as a trifluoromethyl; or a $R_4$—N—$R_5$ unit or a S—$(C_1-C_6)$alkyl-$NR_4R_5$ unit wherein $R_4$ and $R_5$ represent a $(C_1-C_6)$alkyl group, preferably a methyl or an ethyl group; or a radical thio-$(C_1-C_6)$alkyl, preferably a thio-methyl or a thio-ethyl; a radical thio-aryl, preferably a thio-phenyl; a radical thio-heteroaryl, preferably, a thio-pyridinyl; or a radical thio-$(C_1-C_6)$alkyl-aryl, preferably a thio-benzyl; said radicals being optionally substituted by at least a halogen, preferably a fluorine, a trifluoromethyl, or by a $(C_1-C_6)$alkoxy group, preferably a methoxy, ethoxy, isopropoxy, more preferably a methoxy;

a phenyl group optionally substituted by at least one halogene, preferably a bromine, or a trifluoromethyl group; or a heteroaryl group, preferably a furan, a triazol, a pyridin, a thiazol, a pyran, a pyrrol, an imidazol, a benzofuran, a pyridazin, or a tetrazol, and more preferably a furan or a triazol; and $R_3$ represents a hydrogen or a $(C_1-C_3)$alkyl group, preferably a methyl, an ethyl or an isopropyl; a $(C_1-C_3)$ alkoxy group, preferably a methoxy, an ethoxy or an isopropoxy; or a halogen, advantageously a fluorine. More preferably $R_3$ is H.

The present invention also relates to compounds of formula (II) as above defined.

In a particular embodiment of the invention, $R_a$ is a group selected from the group consisting of a $COR_7$ and a $CO_2R_7$ group and $R_7$ represents a $(C_1-C_6)$alkyl group, preferably a methyl group or a tert-butyl group.

In another particular embodiment, $R_a$ is a group selected from the group consisting of a $COR_7$ and a $CO_2R_7$ group and $R_7$ is a $(C_1-C_6)$alkyl group, preferably a methyl, ethyl, propyl group or tert-butyl group, optionally substituted by at least:

a hydroxy group, a $(C_1-C_6)_n$polyalkyloxy group with n=3, a $R_8$ group, a —$NHCO_2R_8$ unit, a $COR_8$ group, or a $CO_2R_8$ group wherein $R_8$ is such as defined above. Preferably, $R_8$ is:

a $(C_1-C_6)$alkyl group, preferably a methyl or a tert-butyl group, a $(C_1-C_6)$alkylaryl, preferably, a benzyl group, a $NR_9R_{10}$ unit wherein $R_9$ and $R_{10}$ preferably represent a hydrogen, a methyl group or $R_9$ and $R_{10}$ taken together form piperazinyl ring, optionally substituted by a methyl group, a phosphate or pyrophosphate group or a salt thereof, preferably a phosphate group.

In another particular embodiment, $R_7$ represents:

a NH—$NR_9R_{10}$ unit wherein $R_9$ and $R_{10}$ are hydrogen, or a saturated heterocycle, preferably oxopyrrolidinyl.

In a preferred embodiment, $R_a$ is a group selected from the group consisting of a $COR_7$ and a $CO_2R_7$ group and $R_7$ represents a methyl or a tert-butyl group, a $(C_1-C_3)$alkyl substituted by at least one group selected from the group consisting of a $CO_2CH_3$, $N(CH_3)_2$, piperazinyl-$CH_3$, NHBoc, Cbz, Boc, $NH_2$ and phosphate group.

Among the compounds according to the present invention, the following list of compounds may be cited:

(Z)-2-(5-chloro-1H-indol-3-yl)-3-(4-chloropyridin-3-yl)-acrylonitrile;

(Z)-2-(5-bromo-1H-indol-3-yl)-3-(4-chloropyridin-3-yl)-acrylonitrile;

(Z)-2-(5-bromo-1H-indol-3-yl)-3-(4-methoxypyridin-3-yl)-acrylonitrile;

(E)-2-(5-bromo-1H-indol-3-yl)-3-(4-methoxypyridin-3-yl)-acrylonitrile;

(Z)-2-(5-chloro-1H-indol-3-yl)-3-(4-(dimethylamino)pyridin-3-yl)-acrylonitrile;

(Z)-2-(5-chloro-1H-indol-3-yl)-3-(4-dimethylamino)pyridine-3-yl)-acrylonitrile, hydrochloride;

(Z)-2-(5-bromo-1H-indol-3-yl)-3-(4-(dimethylamino)pyridin-3-yl)-acrylonitrile;

(Z)-2-(5-chloro-1H-indol-3-yl)-3-(4-methoxypyridin-3-yl)-acrylonitrile;

(E)-2-(5-chloro-1H-indol-3-yl)-3-(4-methoxypyridin-3-yl)-acrylonitrile;

(Z)-2-(5-chloro-1H-indol-3-yl)-3-(4-phenoxypyridin-3-yl)-acrylonitrile;

(Z)-2-(5-bromo-1H-indol-3-yl)-3-(4-phenoxypyridin-3-yl)-acrylonitrile;

(Z)-2-(5-methoxy-1H-indol-3-yl)-3-(4-methoxypyridin-3-yl)-acrylonitrile;

(Z)-2-(5-bromo-1H-indol-3-yl)-3-(4-ethoxypyridin-3-yl)-acrylonitrile;

(Z)-2-(5-bromo-1H-indol-3-yl)-3-(4-isopropoxypyridin-3-yl)-acrylonitrile;

(Z)-2-(5-bromo-1H-indol-3-yl)-3-(4-methylthio)pyridin-3-yl)-acrylonitrile;

(Z)-2-(5-bromo-1H-indol-3-yl)-3-(4-ethylthio)pyridin-3-yl)-acrylonitrile;

(Z)-2-(5-bromo-1H-indol-3-yl)-3-(4-(3-bromophenyl)pyridin-3-yl)-acrylonitrile;
(Z)-3-(4-(3-bromophenyl)pyridin-3-yl)-2-(5-chloro-1H-indol-3-yl)-acrylonitrile;
(Z)-2-(5-bromo-1H-indol-3-yl)-3-(4-(phenylthio)pyridin-3-yl)-acrylonitrile;
(Z)-3-(4-(benzylthio)pyridin-3-yl)-2-(5-bromo-1H-indol-3-yl)-acrylonitrile;
(Z)-2-(5-bromo-1H-indol-3-yl)-3-(4-(3,4-dimethoxy)thio)pyridin-3-yl)-acrylonitrile;
(Z)-2-(5-bromo-1H-indol-3-yl)-3-(4-(4-fluorophenoxy)pyridin-3-yl)-acrylonitrile;
(Z)-2-(5-chloro-1H-indol-3-yl)-3-(4-(4-fluorophenoxy)pyridin-3-yl)-acrylonitrile;
(Z)-2-(5-bromo-1H-indol-3-yl)-3-(4-(diethylamino)pyridin-3-yl)-acrylonitrile;
(Z)-2-(5-bromo-1H-indol-3-yl)-3-(4-(4-(trifluoromethyl)phenyl)pyridin-3-yl)-acrylonitrile;
(Z)-2-(5-chloro-1H-indol-3-yl)-3-(4-(4-(trifluoromethyl)phenyl)pyridin-3-yl)-acrylonitrile;
(Z)-2-(5-chloro-1H-indol-3-yl)-3-(4-((4-fluorophenyl)thio)pyridin-3-yl)-acrylonitrile;
(Z)-2-(5-bromo-1H-indol-3-yl)-3-(4-((4-fluorophenyl)thio)pyridin-3-yl)-acrylonitrile;
(Z)-2-(5-chloro-1H-indol-3-yl)-3-(4-(furan-3-yl)pyridin-3-yl)-acrylonitrile;
(Z)-2-(5-chloro-1H-indol-3-yl)-3-(4-(pyridine-2-ylthio)pyridin-3-yl)-acrylonitrile;
(Z)-2-(5-bromo-1H-indol-3-yl)-3-(4-(pyridine-2-ylthio)pyridin-3-yl)-acrylonitrile;
(Z)-3-(4-(1H-1,2,4-triazol-1-yl)pyridin-3-yl)-2-(5-bromo-1H-indol-3-yl)-acrylonitrile;
(Z)-3-(4-(1H-1,2,4-triazol-1-yl)pyridin-3-yl)-2-(5-chloro-1H-indol-3-yl)-acrylonitrile;
(Z)-2-(5-bromo-1H-indol-3-yl)-3-(4-(furan-3-yl)pyridin-3-yl)-acrylonitrile;
(E)-2-(5-bromo-1H-indol-3-yl)-3-(4-(furan-3-yl)pyridin-3-yl)-acrylonitrile;
(Z)-2-(5-chloro-1H-indol-3-yl)-3-(4-methoxypyridin-3-yl)-acrylonitrile;
(Z)-2-(5-bromo-1H-indol-3-yl)-3-(4-(2-(dimethylamino)ethylthio)pyridin-3-yl)-acrylonitrile;
(Z)-3-(2-(5-bromo-1H-indol-3-yl)-2-cyanovinyl)-4-(4-fluorophenoxy)benzonitrile;
(Z)-3-(2-(5-bromo-1H-indol-3-yl)-2-cyanovinyl)-4-methoxybenzonitrile;
(E)-3-(2-(5-bromo-1H-indol-3-yl)-2-cyanovinyl)-4-methoxybenzonitrile;
(Z)-3-(2-(5-bromo-1H-indol-3-yl)-2-cyanovinyl)-4-(dimethylamino)benzonitrile;
(Z)-3-(2-(5-chloro-1H-indol-3-yl)-2-cyanovinyl)-4-methoxybenzonitrile;
(Z)-3-(2-(5-chloro-1H-indol-3-yl)-2-cyanovinyl)-4-(dimethylamino)benzonitrile;
(Z)-3-(2-(5-chloro-1H-indol-3-yl)-2-cyanovinyl)-4-(ethylthio)benzonitrile;
(Z)—N-(3-(2-(5-bromo-1H-indol-3-yl)-2-cyanovinyl)pyridin-4-yl)pivalamide;
(Z)—N-(3-(2-(5-chloro-1H-indol-3-yl)-2-cyanovinyl)pyridin-4-yl)pivalamide;
(Z)-2-(6-bromo-1H-indol-3-yl)-3-(4-methoxypyridin-3-yl)acrylonitrile;
(Z)-2-(6-fluoro-1H-indol-3-yl)-3-(4-methoxypyridin-3-yl)acrylonitrile;
(Z)-2-(6-chloro-1H-indol-3-yl)-3-(4-methoxypyridin-3-yl)acrylonitrile;
(Z)-3-(2-(5-bromo-1H-indol-3-yl)-2-cyanovinyl)-4-(furan-3-yl)pyridine-1-oxide;
(Z)-3-(2-(5-chloro-1H-indol-3-yl)-2-cyanovinyl)-4-methoxypyridine-1-oxide;
(Z)-2-(5-chloro-1H-indol-3-yl)-3-(4-hydroxypyridin-3-yl)acrylonitrile;
(Z)-3-(2-(5-bromo-1H-indol-3-yl)-2-cyanovinyl)-4-hydroxybenzonitrile;
(Z)-3-(2-(5-chloro-1H-indol-3-yl)-2-cyanovinyl)-4-(trifluoromethoxy)benzonitrile;
(Z)-3-(2-(5-bromo-1H-indol-3-yl)-2-cyanovinyl)-4-(trifluoromethoxy)benzonitrile;
(Z)-3-(2-cyano-2-(6-methoxy-1H-indol-3-yl)vinyl)-4-methoxybenzonitrile;
(Z)-2-(1-acetyl-5-bromo-1H-indol-3-yl)-3-(4-methoxypyridin-3-yl)acrylonitrile;
(Z)-3-(2-(1-acetyl-5-bromo-1H-indol-3-yl)-2-cyanovinyl)-4-methoxybenzonitrile;
(Z)-2-(5-bromo-1-pivaloyl-1H-indol-3-yl)-3-(4-methoxypyridin-3-yl)acrylonitrile;
(Z)-3-(2-(5-bromo-1-pivaloyl-1H-indol-3-yl)-2-cyanovinyl)-4-methoxybenzonitrile;
(Z)-methyl 3-(5-bromo-3-(1-cyano-2-(4-methoxypyridin-3-yl)vinyl)-1H-indol-1-yl)-3-oxopropanoate;
(Z)-2-(5-bromo-1-(2-(dimethylamino)acetyl)-1H-indol-3-yl)-3-(4-methoxypyridin-3-yl)acrylonitrile;
(Z)-2-(4-methylpiperazin-1-yl)ethyl 5-bromo-3-(1-cyano-2-(4-methoxypyridin-3-yl)vinyl)-1H-indole-1-carboxylate;
((Z)-3-(2-(5-bromo-1-(2-(dimethylamino)acetyl)-1H-indol-3-yl)-2-cyanovinyl)-4-methoxybenzonitrile;
(Z)-tert-butyl 5-bromo-3-(1-cyano-2-(5-cyano-2-methoxyphenyl)vinyl)-1H-indole-1-carboxylate;
(R,Z)-benzyl-4-(5-bromo-3-(1-cyano-2-(5-cyano-2-methoxyphenyl)vinyl)-1H-indol-1-yl)-2-(tert-butoxycarbonylamino)-4-oxobutanoate;
(R,Z)-tert-butyl-5-(5-bromo-3-(1-cyano-2-(5-cyano-2-methoxyphenyl)vinyl)-1H-indol-1-yl)-2-(tert-butoxycarbonylamino)-5-oxopentanoate;
(R,Z)-benzyl-2-amino-4-(5-bromo-3-(1-cyano-2-(5-cyano-2-methoxyphenyl)vinyl)-1H-indol-1-yl)-4-oxobutanoate;
(Z)-3-(2-(5-bromo-1-(2-(4-methylpiperazin-1-yl)acetyl)-1H-indol-3-yl)-2-cyanovinyl)-4-methoxybenzonitrile;
(Z)-3-(2-(5-bromo-1-(2-(4-methylpiperazin-1-yl)acetyl)-1H-indol-3-yl)-2-cyanovinyl)-4-methoxybenzonitrile hydrochloride;
(S,Z)-3-(2-(1-(3-aminobutanoyl)-5-bromo-1H-indol-3-yl)-2-cyanovinyl)-4-methoxybenzonitrile hydrochloride;
(Z)-3-(2-(1-(2-aminoacetyl)-5-bromo-1H-indol-3-yl)-2-cyanovinyl)-4-methoxybenzonitrile hydrochloride;
(Z)-3-(2-(5-bromo-1-(2-(piperazin-1-yl)acetyl)-1H-indol-3-yl)-2-cyanovinyl)-4-methoxybenzonitrile hydrochloride;
(Z)-3-(2-(5-bromo-1-(2-(2-(2-methoxyethoxy)ethoxy)acetyl)-1H-indol-3-yl)-2-cyanovinyl)-4-methoxybenzonitrile;
(S,Z)-3-(2-(1-(2-amino-3-hydroxypropanoyl)-5-bromo-1H-indol-3-yl)-2-cyanovinyl)-4-methoxybenzonitrile hydrochloride;
(Z)-3-(2-(5-bromo-1-(5-oxopyrrolidine-2-carbonyl)-1H-indol-3-yl)-2-cyanovinyl)-4-methoxybenzonitrile;
(R,Z)-3-(2-(5-bromo-1-(2,6-diaminohexanoyl)-1H-indol-3-yl)-2-cyanovinyl)-4-methoxybenzonitrile dihydrochloride;
(Z)-3-(5-bromo-3-(1-cyano-2-(5-cyano-2-methoxyphenyl)vinyl)-1H-indol-1-yl)-3-oxopropyl dihydrogen phosphate;
and their pharmaceutically acceptable salts.

Preferably, the following list of compounds may be cited:
(Z)-2-(5-chloro-1H-indol-3-yl)-3-(4-chloropyridin-3-yl)-acrylonitrile;
(Z)-2-(5-bromo-1H-indol-3-yl)-3-(4-chloropyridin-3-yl)-acrylonitrile;
(Z)-2-(5-bromo-1H-indol-3-yl)-3-(4-methoxypyridin-3-yl)-acrylonitrile;
(E)-2-(5-bromo-1H-indol-3-yl)-3-(4-methoxypyridin-3-yl)-acrylonitrile;
(Z)-2-(5-chloro-1H-indol-3-yl)-3-(4-(dimethylamino)pyridin-3-yl)-acrylonitrile;
(Z)-2-(5-chloro-1H-indol-3-yl)-3-(4-dimethylamino)pyridine-3-yl)-acrylonitrile, hydrochloride;
(Z)-2-(5-bromo-1H-indol-3-yl)-3-(4-(dimethylamino)pyridin-3-yl)-acrylonitrile;
(Z)-2-(5-chloro-1H-indol-3-yl)-3-(4-methoxypyridin-3-yl)-acrylonitrile;
(E)-2-(5-chloro-1H-indol-3-yl)-3-(4-methoxypyridin-3-yl)-acrylonitrile;
(Z)-2-(5-chloro-1H-indol-3-yl)-3-(4-phenoxypyridin-3-yl)-acrylonitrile;
(Z)-2-(5-bromo-1H-indol-3-yl)-3-(4-phenoxypyridin-3-yl)-acrylonitrile;
(Z)-2-(5-methoxy-1H-indol-3-yl)-3-(4-methoxypyridin-3-yl)-acrylonitrile;
(Z)-2-(5-bromo-1H-indol-3-yl)-3-(4-ethoxypyridin-3-yl)-acrylonitrile;
(Z)-2-(5-bromo-1H-indol-3-yl)-3-(4-isopropoxypyridin-3-yl)-acrylonitrile;
(Z)-2-(5-bromo-1H-indol-3-yl)-3-(4-methylthio)pyridin-3-yl)-acrylonitrile;
(Z)-2-(5-bromo-1H-indol-3-yl)-3-(4-ethylthio)pyridin-3-yl)-acrylonitrile;
(Z)-2-(5-bromo-1H-indol-3-yl)-3-(4-(3-bromophenyl)pyridin-3-yl)-acrylonitrile;
(Z)-3-(4-(3-bromophenyl)pyridin-3-yl)-2-(5-chloro-1H-indol-3-yl)-acrylonitrile;
(Z)-2-(5-bromo-1H-indol-3-yl)-3-(4-(phenylthio)pyridin-3-yl)-acrylonitrile;
(Z)-3-(4-(benzylthio)pyridin-3-yl)-2-(5-bromo-1H-indol-3-yl)-acrylonitrile;
(Z)-2-(5-bromo-1H-indol-3-yl)-3-(4-(3,4-dimethoxy)thio)pyridin-3-yl)-acrylonitrile;
(Z)-2-(5-bromo-1H-indol-3-yl)-3-(4-(4-fluorophenoxy)pyridin-3-yl)-acrylonitrile;
(Z)-2-(5-chloro-1H-indol-3-yl)-3-(4-(4-fluorophenoxy)pyridin-3-yl)-acrylonitrile;
(Z)-2-(5-bromo-1H-indol-3-yl)-3-(4-(diethylamino)pyridin-3-yl)-acrylonitrile;
(Z)-2-(5-bromo-1H-indol-3-yl)-3-(4-(4-(trifluoromethyl)phenyl)pyridin-3-yl)-acrylonitrile;
(Z)-2-(5-chloro-1H-indol-3-yl)-3-(4-(4-(trifluoromethyl)phenyl)pyridin-3-yl)-acrylonitrile;
(Z)-2-(5-chloro-1H-indol-3-yl)-3-(4-((4-fluorophenyl)thio)pyridin-3-yl)-acrylonitrile;
(Z)-2-(5-bromo-1H-indol-3-yl)-3-(4-((4-fluorophenyl)thio)pyridin-3-yl)-acrylonitrile;
(Z)-2-(5-chloro-1H-indol-3-yl)-3-(4-(furan-3-yl)pyridin-3-yl)-acrylonitrile;
(Z)-2-(5-chloro-1H-indol-3-yl)-3-(4-(pyridine-2-ylthio)pyridin-3-yl)-acrylonitrile;
(Z)-2-(5-bromo-1H-indol-3-yl)-3-(4-(pyridine-2-ylthio)pyridin-3-yl)-acrylonitrile;
(Z)-3-(4-(1H-1,2,4-triazol-1-yl)pyridin-3-yl)-2-(5-bromo-1H-indol-3-yl)-acrylonitrile;
(Z)-3-(4-(1H-1,2,4-triazol-1-yl)pyridin-3-yl)-2-(5-chloro-1H-indol-3-yl)-acrylonitrile;
(Z)-2-(5-bromo-1H-indol-3-yl)-3-(4-(furan-3-yl)pyridin-3-yl)-acrylonitrile;
(E)-2-(5-bromo-1H-indol-3-yl)-3-(4-(furan-3-yl)pyridin-3-yl)-acrylonitrile;
(Z)-2-(5-chloro-1H-indol-3-yl)-3-(4-methoxypyridin-3-yl)-acrylonitrile;
(Z)-2-(5-bromo-1H-indol-3-yl)-3-(4-(2-(dimethylamino)ethylthio)pyridin-3-yl)-acrylonitrile;
(Z)-3-(2-(5-bromo-1H-indol-3-yl)-2-cyanovinyl)-4-(4-fluorophenoxy)benzonitrile;
(Z)-3-(2-(5-bromo-1H-indol-3-yl)-2-cyanovinyl)-4-methoxybenzonitrile;
(E)-3-(2-(5-bromo-1H-indol-3-yl)-2-cyanovinyl)-4-methoxybenzonitrile;
(Z)-3-(2-(5-bromo-1H-indol-3-yl)-2-cyanovinyl)-4-(dimethylamino)benzonitrile;
(Z)-3-(2-(5-chloro-1H-indol-3-yl)-2-cyanovinyl)-4-methoxybenzonitrile;
(Z)-3-(2-(5-chloro-1H-indol-3-yl)-2-cyanovinyl)-4-(dimethylamino)benzonitrile;
(Z)—N-(3-(2-(5-chloro-1H-indol-3-yl)-2-cyanovinyl)-4-(ethylthio)benzonitrile;
(Z)—N-(3-(2-(5-bromo-1H-indol-3-yl)-2-cyanovinyl)pyridin-4-yl)pivalamide;
(Z)—N-(3-(2-(5-chloro-1H-indol-3-yl)-2-cyanovinyl)pyridin-4-yl)pivalamide;
(Z)-2-(6-bromo-1H-indol-3-yl)-3-(4-methoxypyridin-3-yl)acrylonitrile;
(Z)-2-(6-fluoro-1H-indol-3-yl)-3-(4-methoxypyridin-3-yl)acrylonitrile;
(Z)-2-(6-chloro-1H-indol-3-yl)-3-(4-methoxypyridin-3-yl)acrylonitrile;
(Z)-3-(2-(5-bromo-1H-indol-3-yl)-2-cyanovinyl)-4-(furan-3-yl)pyridine-1-oxide;
(Z)-3-(2-(5-chloro-1H-indol-3-yl)-2-cyanovinyl)-4-methoxypyridine-1-oxide;
(Z)-2-(5-chloro-1H-indol-3-yl)-3-(4-hydroxypyridin-3-yl)acrylonitrile;
(Z)-3-(2-(5-bromo-1H-indol-3-yl)-2-cyanovinyl)-4-hydroxybenzonitrile;
(Z)-3-(2-(5-chloro-1H-indol-3-yl)-2-cyanovinyl)-4-(trifluoromethoxy)benzonitrile;
(Z)-3-(2-(5-bromo-1H-indol-3-yl)-2-cyanovinyl)-4-(trifluoromethoxy)benzonitrile;
(Z)-3-(2-cyano-2-(6-methoxy-1H-indol-3-yl)vinyl)-4-methoxybenzonitrile;
and their pharmaceutically acceptable salts.

More preferably, the following list of compounds may be cited:
(Z)-2-(5-chloro-1H-indol-3-yl)-3-(4-chloropyridin-3-yl)-acrylonitrile;
(Z)-2-(5-bromo-1H-indol-3-yl)-3-(4-chloropyridin-3-yl)-acrylonitrile;
(Z)-2-(5-bromo-1H-indol-3-yl)-3-(4-methoxypyridin-3-yl)-acrylonitrile;
(E)-2-(5-bromo-1H-indol-3-yl)-3-(4-methoxypyridin-3-yl)-acrylonitrile;
(Z)-2-(5-chloro-1H-indol-3-yl)-3-(4-methoxypyridin-3-yl)-acrylonitrile;
(E)-2-(5-chloro-1H-indol-3-yl)-3-(4-methoxypyridin-3-yl)-acrylonitrile;
(Z)-2-(5-methoxy-1H-indol-3-yl)-3-(4-methoxypyridin-3-yl)-acrylonitrile;
(Z)-2-(5-bromo-1H-indol-3-yl)-3-(4-ethoxypyridin-3-yl)-acrylonitrile;
(Z)-2-(5-bromo-1H-indol-3-yl)-3-(4-isopropoxypyridin-3-yl)-acrylonitrile;

(Z)-2-(5-bromo-1H-indol-3-yl)-3-(4-(methylthio)pyridin-3-yl)-acrylonitrile;
(Z)-2-(5-bromo-1H-indol-3-yl)-3-(4-(phenylthio)pyridin-3-yl)-acrylonitrile;
(Z)-3-(4-(benzylthio)pyridin-3-yl)-2-(5-bromo-1H-indol-3-yl)-acrylonitrile;
(Z)-2-(5-bromo-1H-indol-3-yl)-3-(4-(4-fluorophenoxy)pyridin-3-yl)-acrylonitrile;
(Z)-2-(5-chloro-1H-indol-3-yl)-3-(4-(4-fluorophenoxy)pyridin-3-yl)-acrylonitrile;
(Z)-2-(5-bromo-1H-indol-3-yl)-3-(4-(dimethylamino)pyridin-3-yl)-acrylonitrile;
(Z)-2-(5-bromo-1H-indol-3-yl)-3-(4-(diethylamino)pyridin-3-yl)-acrylonitrile;
(Z)-2-(5-bromo-1H-indol-3-yl)-3-(4-(4-(trifluoromethyl)phenyl)pyridin-3-yl)-acrylonitrile;
(Z)-2-(5-chloro-1H-indol-3-yl)-3-(4-((4-fluorophenyl)thio)pyridin-3-yl)-acrylonitrile;
(Z)-2-(5-bromo-1H-indol-3-yl)-3-(4-((4-fluorophenyl)thio)pyridin-3-yl)-acrylonitrile;
(Z)-2-(5-chloro-1H-indol-3-yl)-3-(4-(furan-3-yl)pyridin-3-yl)-acrylonitrile;
(Z)-2-(5-chloro-1H-indol-3-yl)-3-(4-(pyridine-2-ylthio)pyridin-3-yl)-acrylonitrile;
(Z)-3-(4-(1H-1,2,4-triazol-1-yl)pyridin-3-yl)-2-(5-bromo-1H-indol-3-yl)-acrylonitrile;
(Z)-3-(4-(1H-1,2,4-triazol-1-yl)pyridin-3-yl)-2-(5-chloro-1H-indol-3-yl)-acrylonitrile;
(Z)-2-(5-bromo-1H-indol-3-yl)-3-(4-(furan-3-yl)pyridin-3-yl)-acrylonitrile;
(E)-2-(5-bromo-1H-indol-3-yl)-3-(4-(furan-3-yl)pyridin-3-yl)-acrylonitrile;
(Z)-2-(5-chloro-1H-indol-3-yl)-3-(4-methoxypyridin-3-yl)-acrylonitrile;
(Z)-3-(2-(5-bromo-1H-indol-3-yl)-2-cyanovinyl)-4-methoxybenzonitrile;
(E)-3-(2-(5-bromo-1H-indol-3-yl)-2-cyanovinyl)-4-methoxybenzonitrile;
(Z)-3-(2-(5-bromo-1H-indol-3-yl)-2-cyanovinyl)-4-(dimethylamino)benzonitrile;
(Z)-2-(6-bromo-1H-indol-3-yl)-3-(4-methoxypyridin-3-yl)acrylonitrile;
(Z)-2-(6-fluoro-1H-indol-3-yl)-3-(4-methoxypyridin-3-yl)acrylonitrile;
(Z)-2-(6-chloro-1H-indol-3-yl)-3-(4-methoxypyridin-3-yl)acrylonitrile;
(Z)-3-(2-(5-bromo-1H-indol-3-yl)-2-cyanovinyl)-4-(furan-3-yl)pyridine-1-oxide;
(Z)-3-(2-(5-chloro-1H-indol-3-yl)-2-cyanovinyl)-4-methoxypyridine-1-oxide;
(Z)-3-(2-(5-chloro-1H-indol-3-yl)-2-cyanovinyl)-4-(trifluoromethoxy)benzonitrile;
(Z)-3-(2-(5-bromo-1H-indol-3-yl)-2-cyanovinyl)-4-(trifluoromethoxy)benzonitrile;
and their pharmaceutically acceptable salts.

More preferably, the following list of compounds may be cited:
(Z)-2-(5-chloro-1H-indol-3-yl)-3-(4-chloropyridin-3-yl)-acrylonitrile;
(Z)-2-(5-bromo-1H-indol-3-yl)-3-(4-chloropyridin-3-yl)-acrylonitrile;
(Z)-2-(5-bromo-1H-indol-3-yl)-3-(4-methoxypyridin-3-yl)-acrylonitrile;
(E)-2-(5-bromo-1H-indol-3-yl)-3-(4-methoxypyridin-3-yl)-acrylonitrile;
(Z)-2-(5-chloro-1H-indol-3-yl)-3-(4-methoxypyridin-3-yl)-acrylonitrile;
(E)-2-(5-chloro-1H-indol-3-yl)-3-(4-methoxypyridin-3-yl)-acrylonitrile;
(Z)-2-(5-bromo-1H-indol-3-yl)-3-(4-(dimethylamino)pyridin-3-yl)-acrylonitrile;
(Z)-2-(5-methoxy-1H-indol-3-yl)-3-(4-methoxypyridin-3-yl)-acrylonitrile;
(Z)-2-(5-bromo-1H-indol-3-yl)-3-(4-(methylthio)pyridin-3-yl)-acrylonitrile;
(Z)-2-(5-bromo-1H-indol-3-yl)-3-(4-(diethylamino)pyridin-3-yl)-acrylonitrile;
(Z)-2-(5-chloro-1H-indol-3-yl)-3-(4-(furan-3-yl)pyridin-3-yl)-acrylonitrile;
(Z)-2-(5-bromo-1H-indol-3-yl)-3-(4-(furan-3-yl)pyridin-3-yl)-acrylonitrile;
(E)-2-(5-bromo-1H-indol-3-yl)-3-(4-(furan-3-yl)pyridin-3-yl)-acrylonitrile;
(Z)-3-(2-(5-bromo-1H-indol-3-yl)-2-cyanovinyl)-4-methoxybenzonitrile;
(E)-3-(2-(5-bromo-1H-indol-3-yl)-2-cyanovinyl)-4-methoxybenzonitrile;
(Z)-3-(2-(5-bromo-1H-indol-3-yl)-2-cyanovinyl)-4-(dimethylamino)benzonitrile;
(Z)-2-(6-bromo-1H-indol-3-yl)-3-(4-methoxypyridin-3-yl)acrylonitrile;
(Z)-2-(6-fluoro-1H-indol-3-yl)-3-(4-methoxypyridin-3-yl)acrylonitrile;
(Z)-2-(6-chloro-1H-indol-3-yl)-3-(4-methoxypyridin-3-yl)acrylonitrile;
(Z)-3-(2-(5-bromo-1H-indol-3-yl)-2-cyanovinyl)-4-(furan-3-yl)pyridine-1-oxide;
(Z)-3-(2-(5-chloro-1H-indol-3-yl)-2-cyanovinyl)-4-methoxypyridine-1-oxide;
(Z)-3-(2-(5-chloro-1H-indol-3-yl)-2-cyanovinyl)-4-(trifluoromethoxy)benzonitrile;
(Z)-3-(2-(5-bromo-1H-indol-3-yl)-2-cyanovinyl)-4-(trifluoromethoxy)benzonitrile;
and their pharmaceutically acceptable salts.

In another embodiment, compounds are chosen from the group consisting of:
(Z)-2-(1-acetyl-5-bromo-1H-indol-3-yl)-3-(4-methoxypyridin-3-yl)acrylonitrile;
(Z)-3-(2-(1-acetyl-5-bromo-1H-indol-3-yl)-2-cyanovinyl)-4-methoxybenzonitrile;
(Z)-2-(5-bromo-1-pivaloyl-1H-indol-3-yl)-3-(4-methoxypyridin-3-yl)acrylonitrile;
(Z)-3-(2-(5-bromo-1-pivaloyl-1H-indol-3-yl)-2-cyanovinyl)-4-methoxybenzonitrile;
(Z)-methyl 3-(5-bromo-3-(1-cyano-2-(4-methoxypyridin-3-yl)vinyl)-1H-indol-1-yl)-3-oxopropanoate;
(Z)-2-(5-bromo-1-(2-(dimethylamino)acetyl)-1H-indol-3-yl)-3-(4-methoxypyridin-3-yl)acrylonitrile;
(Z)-2-(4-methylpiperazin-1-yl)ethyl 5-bromo-3-(1-cyano-2-(4-methoxypyridin-3-yl)vinyl)-1H-indole-1-carboxylate;
((Z)-3-(2-(5-bromo-1-(2-(dimethylamino)acetyl)-1H-indol-3-yl)-2-cyanovinyl)-4-methoxybenzonitrile;
(Z)-tert-butyl 5-bromo-3-(1-cyano-2-(5-cyano-2-methoxyphenyl)vinyl)-1H-indole-1-carboxylate;
(R,Z)-benzyl-4-(5-bromo-3-(1-cyano-2-(5-cyano-2-methoxyphenyl)vinyl)-1H-indol-1-yl)-2-(tert-butoxycarbonylamino)-4-oxobutanoate;
(R,Z)-tert-butyl-5-(5-bromo-3-(1-cyano-2-(5-cyano-2-methoxyphenyl)vinyl)-1H-indol-1-yl)-2-(tert-butoxycarbonylamino)-5-oxopentanoate;
(R,Z)-benzyl-2-amino-4-(5-bromo-3-(1-cyano-2-(5-cyano-2-methoxyphenyl)vinyl)-1H-indol-1-yl)-4-oxobutanoate;
(Z)-3-(2-(5-bromo-1-(2-(4-methylpiperazin-1-yl)acetyl)-1H-indol-3-yl)-2-cyanovinyl)-4-methoxybenzonitrile;

(Z)-3-(2-(5-bromo-1-(2-(4-methylpiperazin-1-yl)acetyl)-1H-indol-3-yl)-2-cyanovinyl)-4-methoxybenzonitrile hydrochloride;

(S,Z)-3-(2-(1-(3-aminobutanoyl)-5-bromo-1H-indol-3-yl)-2-cyanovinyl)-4-methoxybenzonitrile hydrochloride;

(Z)-3-(2-(1-(2-aminoacetyl)-5-bromo-1H-indol-3-yl)-2-cyanovinyl)-4-methoxybenzonitrile hydrochloride;

(Z)-3-(2-(5-bromo-1-(2-(piperazin-1-yl)acetyl)-1H-indol-3-yl)-2-cyanovinyl)-4-methoxybenzonitrile hydrochloride;

(Z)-3-(2-(5-bromo-1-(2-(2-(2-methoxyethoxy)ethoxy)acetyl)-1H-indol-3-yl)-2-cyanovinyl)-4-methoxybenzonitrile;

(S,Z)-3-(2-(1-(2-amino-3-hydroxypropanoyl)-5-bromo-1H-indol-3-yl)-2-cyanovinyl)-4-methoxybenzonitrile hydrochloride;

(Z)-3-(2-(5-bromo-1-(5-oxopyrrolidine-2-carbonyl)-1H-indol-3-yl)-2-cyanovinyl)-4-methoxybenzonitrile;

(R,Z)-3-(2-(5-bromo-1-(2,6-diaminohexanoyl)-1H-indol-3-yl)-2-cyanovinyl)-4-methoxybenzonitrile dihydrochloride;

(Z)-3-(5-bromo-3-(1-cyano-2-(5-cyano-2-methoxyphenyl)vinyl)-1H-indol-1-yl)-3-oxopropyl dihydrogen phosphate;

and their pharmaceutically acceptable salts.

Preferably, compounds are chosen from the group consisting of:

(Z)-2-(1-acetyl-5-bromo-1H-indol-3-yl)-3-(4-methoxypyridin-3-yl)acrylonitrile;

(Z)-3-(2-(1-acetyl-5-bromo-1H-indol-3-yl)-2-cyanovinyl)-4-methoxybenzonitrile;

(Z)-2-(5-bromo-1-pivaloyl-1H-indol-3-yl)-3-(4-methoxypyridin-3-yl)acrylonitrile;

(Z)-3-(2-(5-bromo-1-pivaloyl-1H-indol-3-yl)-2-cyanovinyl)-4-methoxybenzonitrile;

(Z)-methyl 3-(5-bromo-3-(1-cyano-2-(4-methoxypyridin-3-yl)vinyl)-1H-indol-1-yl)-3-oxopropanoate;

(Z)-2-(5-bromo-1-(2-(dimethylamino)acetyl)-1H-indol-3-yl)-3-(4-methoxypyridin-3-yl)acrylonitrile;

(Z)-2-(4-methylpiperazin-1-yl)ethyl 5-bromo-3-(1-cyano-2-(4-methoxypyridin-3-yl)vinyl)-1H-indole-1-carboxylate;

((Z)-3-(2-(5-bromo-1-(2-(dimethylamino)acetyl)-1H-indol-3-yl)-2-cyanovinyl)-4-methoxybenzonitrile;

(Z)-tert-butyl 5-bromo-3-(1-cyano-2-(5-cyano-2-methoxyphenyl)vinyl)-1H-indole-1-carboxylate;

(R,Z)-benzyl-4-(5-bromo-3-(1-cyano-2-(5-cyano-2-methoxyphenyl)vinyl)-1H-indol-1-yl)-2-(tert-butoxycarbonylamino)-4-oxobutanoate;

(R,Z)-tert-butyl-5-(5-bromo-3-(1-cyano-2-(5-cyano-2-methoxyphenyl)vinyl)-1H-indol-1-yl)-2-(tert-butoxycarbonylamino)-5-oxopentanoate;

(R,Z)-benzyl-2-amino-4-(5-bromo-3-(1-cyano-2-(5-cyano-2-methoxyphenyl)vinyl)-1H-indol-1-yl)-4-oxobutanoate;

(R,Z)-3-(2-(5-bromo-1-(2,6-diaminohexanoyl)-1H-indol-3-yl)-2-cyanovinyl)-4-methoxybenzonitrile dihydrochloride;

(Z)-3-(5-bromo-3-(1-cyano-2-(5-cyano-2-methoxyphenyl)vinyl)-1H-indol-1-yl)-3-oxopropyl dihydrogen phosphate;

and their pharmaceutically acceptable salts.

The chemical structures of some compounds of formula (I) and (II) of the invention are illustrated in the following Tables I and II.

TABLE I

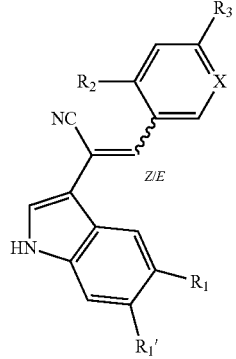

(I)

|  | X | R1 | R1' | R2 | R3 | Z/E |
|---|---|---|---|---|---|---|
| WO2010/150211 Example 1 | N | H | H | H | H | Z |
| WO2010/150211 Example 4 | N | —O—CH₃ | H | H | H | Z |
| WO2010/150211 Example 22 | N | —O—CH₂—CH₃ | H | H | H | Z |
| WO2010/150211 Example 23 | N | —O—CH—(CH₃)₂ | H | H | H | Z |
| WO2010/150211 Example 24 | N | —Cl | H | H | H | Z |
| WO2010/150211 Example 28 | N | —O—CH₃ | H | H | —F | Z |
| WO2010/150211 Example 31 | N | —O—CH₃ | H | —CH₃ | H | Z |
| WO2010/150211 Example 47 | N | —O—CH₃ | H | —Cl | H | Z |
| WO2010/150211 Example 37 | N | —Br | H | H | H | Z |

TABLE I-continued

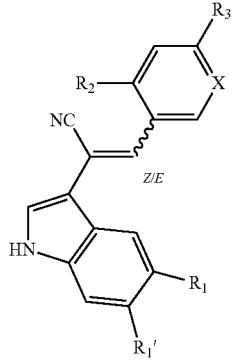

(I)

|  | X | R1 | R1' | R2 | R3 | Z/E |
|---|---|---|---|---|---|---|
| WO2010/150211 Example 26 | N | H | —O—CH₃ | H | H | Z |
| WO2010/150211 Example 52 | N | —O—CH₃ | H | H | —O—CH₃ | Z |
| WO2010/150211 Example 30 | C—CN | —O—CH₃ | H | H | H | Z |
| Example 2 | N | —O—CH₃ | H | —O—CH₂—CH₃ | H | Z |
| Example 3 | N | —Cl | H | —Cl | H | Z |
| Example 4 | N | —Br | H | —Cl | H | Z |
| Example 5 | N | —Br | H | —O—CH₃ | H | Z |
| Example 5b | N | —Br | H | —O—CH₃ | H | E |
| Example 6 | N | —Cl | H | —N—(CH₃)₂ | H | Z |
| Example 7 | N | —Cl | H | —N—(CH₃)₂ | H | Z |
| Example 8 | N | —Br | H | —N—(CH₃)₂ | H | Z |
| Example 9 | N | —Cl | H | —O—CH₃ | H | Z |
| Example 9b | N | —Cl | H | —O—CH₃ | H | E |
| Example 10 | N | —Cl | H | —O—C₆H₅ | H | Z |
| Example 11 | N | —Br | H | —O—C₆H₅ | H | Z |
| Example 12 | N | —O—CH₃ | H | —O—CH₃ | H | Z |
| Example 13 | N | —Br | H | —O—CH₂—CH₃ | H | Z |
| Example 14 | N | —Br | H | —O—CH—(CH₃)₂ | H | Z |
| Example 15 | N | —Br | H | —S—CH₃ | H | Z |
| Example 16 | N | —Br | H | —S—CH₂—CH₃ | H | Z |
| Example 17 | N | —Br | H | —(C₆H₄)—3-Br | H | Z |
| Example 18 | N | —Cl | H | —(C₆H₄)—3-Br | H | Z |
| Example 19 | N | —Br | H | —S—C₆H₅ | H | Z |
| Example 20 | N | —Br | H | —S—CH₂—C₆H₅ | H | Z |
| Example 21 | N | —Br | H | —S—C₆H₅-3,4-(—OCH₃)₂ | H | Z |
| Example 22 | N | —Br | H | —O—C₆H₅—4-F | H | Z |
| Example 23 | N | —Cl | H | —O—C₆H₅—4-F | H | Z |
| Example 24 | N | —Br | H | —N—(CH₂CH₃)₂ | H | Z |
| Example 25 | N | —Br | H | —C₆H₅—4-CF₃ | H | Z |
| Example 26 | N | —Cl | H | —C₆H₅—4-CF₃ | H | Z |
| Example 27 | N | —Cl | H | —S—C₆H₅—4-F | H | Z |
| Example 28 | N | —Br | H | —S—C₆H₅—4-F | H | Z |
| Example 29 | N | —Cl | H | —C₄H₃O | H | Z |
| Example 30 | N | —Cl | H | —S—C₅H₄N | H | Z |
| Example 31 | N | —Br | H | —S—C₅H₄N | H | Z |
| Example 32 | N | —Br | H | —C₂H₂N₃ | H | Z |
| Example 33 | N | —Cl | H | —C₂H₂N₃ | H | Z |
| Example 34 | N | —Br | H | —C₄H₃O | H | Z |
| Example 34b | N | —Br | H | —C₄H₃O | H | E |
| Example 35 | N | —Cl | H | —O—CH₃ | H | Z |
| Example 36 | N | —Br | H | —S—(CH₂)₂—N—(CH₃)₂ | H | Z |
| Example 37 | C—CN | —Br | H | —O—C₆H₅—4-F | H | Z |
| Example 38 | C—CN | —Br | H | —O—CH₃ | H | Z |
| Example 38b | C—CN | —Br | H | —O—CH₃ | H | E |
| Example 39 | C—CN | —Br | H | —N—(CH₃)₂ | H | Z |
| Example 40 | C—CN | —Cl | H | —O—CH₃ | H | Z |
| Example 41 | C—CN | —Cl | H | —N—(CH₃)₂ | H | Z |
| Example 42 | C—CN | —Cl | H | —S—CH₂CH₃ | H | Z |
| Example 43 | N | Br | H | —NH—C(O)C(CH₃)₃ | H | Z |
| Example 44 | N | Cl | H | —NH—C(O)C(CH₃)₃ | H | Z |
| Example 45 | N | H | —Br | —O—CH₃ | H | Z |
| Example 46 | N | H | —F | —O—CH₃ | H | Z |
| Example 47 | N | H | —Cl | —O—CH₃ | H | Z |
| Example 48 | N⁺—O⁻ | —Br | H | —C₄H₃O | H | Z |
| Example 49 | N⁺—O⁻ | —Cl | H | —O—CH₃ | H | Z |
| Example 50 | N | Cl | H | —OH | H | Z |

TABLE I-continued

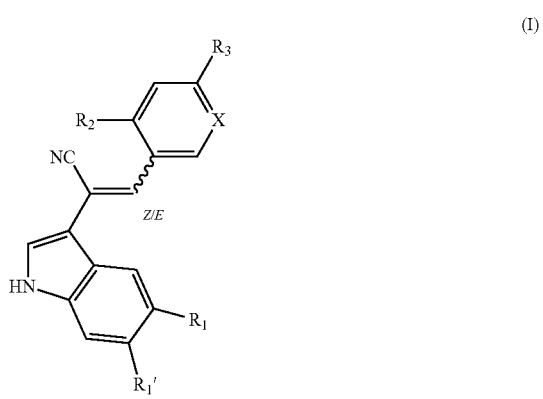

(I)

|  | X | R1 | R1' | R2 | R3 | Z/E |
|---|---|---|---|---|---|---|
| Example 51 | C—CN | Br | H | —OH | H | Z |
| Example 52 | C—CN | Cl | H | —OCF₃ | H | Z |
| Example 53 | C—CN | Br | H | —OCF₃ | H | Z |
| Example 54 | C—CN | H | —O—CH₃ | —O—CH₃ | H | Z |

TABLE II

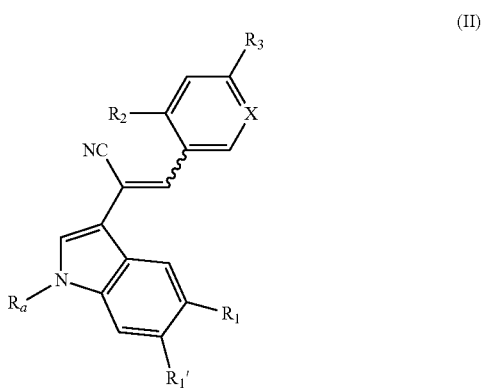

(II)

|  | X | R1 | R1' | R2 | R3 | Z/E | Ra |
|---|---|---|---|---|---|---|---|
| Example 55 | N | Br | H | OCH₃ | H | Z | COCH₃ |
| Example 56 | C—CN | Br | H | OCH₃ | H | Z | COCH₃ |
| Example 57 | N | Br | H | OCH₃ | H | Z | COC(CH₃)₃ |
| Example 58 | C—CN | Br | H | OCH₃ | H | Z | COC(CH₃)₃ |
| Example 59 | N | Br | H | OCH₃ | H | Z | COCH₂CO₂CH₃ |
| Example 60 | N | Br | H | OCH₃ | H | Z | CONHN(CH₃)₂ |
| Example 61 | N | Br | H | OCH₃ | H | Z | COCH₂N(CH₃)₂ |
| Example 62 | N | Br | H | OCH₃ | H | Z | CO₂(CH₂)₂-piperazinyl-CH₃ |
| Example 63 | C—CN | Br | H | OCH₃ | H | Z | COCH₂N(OH₃)₂ |
| Example 64 | C—CN | Br | H | OCH₃ | H | Z | CO₂C(CH₃)₃ |
| Example 65 | C—CN | Br | H | OCH₃ | H | Z | COCH₂—CH(NHBoc)Cbz |
| Example 66 | C—CN | Br | H | OCH₃ | H | Z | CO(CH₂)₂—CH(Boc)—NHBoc |
| Example 67 | C—CN | Br | H | OCH₃ | H | Z | COCH₂—CH(NH₂)—Cbz |
| Example 68 | C—CN | Br | H | OCH₃ | H | Z | CO—CH₂-piperazinyl-CH₃ |
| Example 69 | C—CN | Br | H | OCH₃ | H | Z | CO—CH₂-piperazinyl-CH₃•HCl |
| Example 70 | C—CN | Br | H | OCH₃ | H | Z | COCH₂—CH(CH₃)NH₂ |
| Example 71 | C—CN | Br | H | OCH₃ | H | Z | COCH₂NH₂ |
| Example 72 | C—CN | Br | H | OCH₃ | H | Z | CO—CH₂-piperazinyl |
| Example 73 | C—CN | Br | H | OCH₃ | H | Z | COCH₂O(CH₂)₂O(CH₂)₂OCH₃ |
| Example 74 | C—CN | Br | H | OCH₃ | H | Z | COCH(NH₂)CH₂OH |
| Example 75 | C—CN | Br | H | OCH₃ | H | Z | CO-oxopyrrolidine |
| Example 76 | C—CN | Br | H | OCH₃ | H | Z | COCH(NH₂)—(CH₂)₄NH₂ |
| Example 77 | C—CN | Br | H | OCH₃ | H | Z | COCH₂—PO(OCH₂CH₃)₂ |
| Example 78 | C—CN | Br | H | OCH₃ | H | Z | COCH₃—P₂O₇⁻•[t-BuN]₃⁺ |
| Example 79 | C—CN | Br | H | OCH₃ | H | Z | CO(CH₂)₂PO₄H₂ |

The present invention relates to:
- a pharmaceutical composition comprising any compound having the formula (I), (Ia), (Ib) or (II) as defined above or (Z)-3-(4-ethoxypyridin-3-yl)-2-(5-methoxy-1H-indol-3-yl)-acrylonitrile including any one of the disclosed embodiments; and/or
- a pharmaceutical composition comprising any compound having the formula (I), (Ia), (Ib) or (II) as defined above or (Z)-3-(4-ethoxypyridin-3-yl)-2-(5-methoxy-1H-indol-3-yl)-acrylonitrile including any one of the disclosed embodiments, and a pharmaceutically acceptable carrier; and/or
- a pharmaceutical composition comprising (a) any compound having the formula (I), (Ia), (Ib) or (II) as defined above or (Z)-3-(4-ethoxypyridin-3-yl)-2-(5-methoxy-1H-indol-3-yl)-acrylonitrile including any one of the disclosed embodiments, and (b) an additional active ingredient, preferably an additional antitumoral drug; and/or
- a pharmaceutical composition as defined above or any compound having the formula (I), (Ia), (Ib) or (II) as defined above or (Z)-3-(4-ethoxypyridin-3-yl)-2-(5-methoxy-1H-indol-3-yl)-acrylonitrile including any one of the disclosed embodiments for use as a drug; and/or
- a pharmaceutical composition as defined above or any compound having the formula (I), (Ia), (Ib) or (II) as defined above or (Z)-3-(4-ethoxypyridin-3-yl)-2-(5-methoxy-1H-indol-3-yl)-acrylonitrile including any one of the disclosed embodiments, for use in the treatment of cancer; and/or
- a pharmaceutical composition as defined above or any compound having the formula (I), (Ia), (Ib) or (II) as defined above or (Z)-3-(4-ethoxypyridin-3-yl)-2-(5-methoxy-1H-indol-3-yl)-acrylonitrile including any one of the disclosed embodiments, for use in the treatment of viral infections, particularly HIV infection, HTLV infection, or HPV infection; and/or
- a pharmaceutical composition as defined above or any compound having the formula (I), (Ia), (Ib) or (II) as defined above or (Z)-3-(4-ethoxypyridin-3-yl)-2-(5-methoxy-1H-indol-3-yl)-acrylonitrile including any one of the disclosed embodiments, for use for the treatment of lung disease, particularly the treatment of pulmonary arterial hypertension; and/or
- a pharmaceutical composition as defined above or any compound having the formula (I), (Ia), (Ib) or (II) as defined above or (Z)-3-(4-ethoxypyridin-3-yl)-2-(5-methoxy-1H-indol-3-yl)-acrylonitrile including any one of the disclosed embodiments, for use in the treatment of pathologies associated with dysregulation of MKlp2 or for use in the treatment of pathologies in which the MKlp2 pathway is dysregulated; and/or
- a product or kit containing (a) any compound of formula (I), (Ia), (Ib) or (II) as disclosed above or (Z)-3-(4-ethoxypyridin-3-yl)-2-(5-methoxy-1H-indol-3-yl)-acrylonitrile including any one of the disclosed embodiments and (b) an additional active ingredient, preferably an additional antitumoral drug, as a combined preparation for simultaneous, separate or sequential use, in particular in the treatment of cancer; and/or
- a combined preparation which comprises (a) any compound of formula (I), (Ia), (Ib) or (II) as disclosed above or (Z)-3-(4-ethoxypyridin-3-yl)-2-(5-methoxy-1H-indol-3-yl)-acrylonitrile including any one of the disclosed embodiments and (b) an additional active ingredient, preferably an additional antitumoral drug, for simultaneous, separate or sequential use, in particular in the treatment of cancer; and/or
- a pharmaceutical composition as defined above or any compound having the formula (I), (Ia), (Ib) or (II) as defined above or (Z)-3-(4-ethoxypyridin-3-yl)-2-(5-methoxy-1H-indol-3-yl)-acrylonitrile including any one of the disclosed embodiments, for the use in the treatment of cancer in combination with radiotherapy, surgery (e.g., tumor resection), hyperthermia and/or other antitumoral therapies or before, simultaneously or after surgery (e.g., tumor resection); and/or
- the use of a pharmaceutical composition as defined above or any compound having the formula (I), (Ia), (Ib) or (II) as defined above or (Z)-3-(4-ethoxypyridin-3-yl)-2-(5-methoxy-1H-indol-3-yl)-acrylonitrile including any one of the disclosed embodiments, for the manufacture of a medicament for the treatment of cancer, viral infections, lung diseases and/or pathologies associated with dysregulation of MKlp2 or its pathway, preferably cancer; and/or
- the use of a pharmaceutical composition as defined above or any compound having the formula (I), (Ia), (Ib) or (II) as defined above or (Z)-3-(4-ethoxypyridin-3-yl)-2-(5-methoxy-1H-indol-3-yl)-acrylonitrile including any one of the disclosed embodiments and (b) an additional active ingredient, preferably an additional antitumoral drug, for the manufacture of a medicament for the treatment of cancer; and/or
- a method for treating a cancer in a subject in need thereof, comprising administering an effective amount of a pharmaceutical composition as defined above or any compound having the formula (I), (Ia), (Ib) or (II) as defined above or (Z)-3-(4-ethoxypyridin-3-yl)-2-(5-methoxy-1H-indol-3-yl)-acrylonitrile including any one of the disclosed embodiments; and/or
- a method for treating a cancer in a subject in need thereof, comprising administering an effective amount of a pharmaceutical composition as defined above or any compound having the formula (I), (Ia), (Ib) or (II) as defined above or (Z)-3-(4-ethoxypyridin-3-yl)-2-(5-methoxy-1H-indol-3-yl)-acrylonitrile including any one of the disclosed embodiments and a pharmaceutically acceptable carrier; and/or
- a method for treating a cancer in a subject in need thereof, comprising administering an effective amount of a pharmaceutical composition as defined above or any compound having the formula (I), (Ia), (Ib) or (II) as defined above or (Z)-3-(4-ethoxypyridin-3-yl)-2-(5-methoxy-1H-indol-3-yl)-acrylonitrile including any one of the disclosed embodiments, and (b) an additional active ingredient, preferably an additional antitumoral drug; and/or
- a method for treating a cancer in a subject in need thereof, comprising administering an effective amount of a pharmaceutical composition as defined above or any compound having the formula (I), (Ia), (Ib) or (II) as defined above or (Z)-3-(4-ethoxypyridin-3-yl)-2-(5-methoxy-1H-indol-3-yl)-acrylonitrile including any one of the disclosed embodiments, and an effective amount of a pharmaceutical composition comprising an additional active ingredient, preferably an additional antitumoral drug; and/or
- a method for treating a cancer in a subject in need thereof, comprising administering an effective amount of a pharmaceutical composition as defined above or any compound having the formula (I), (Ia), (Ib) or (II) as defined above or (Z)-3-(4-ethoxypyridin-3-yl)-2-(5- methoxy-1H-indol-3-yl)-acrylonitrile including any one of the disclosed embodiments, in combination with radiotherapy, surgery (e.g., tumor resection), hyperthermia and/or other antitumoral therapies; and/or a method for treating a viral infection in a subject in need thereof, comprising administering an effective amount of a pharmaceutical composition as defined above or any compound having the formula (I), (Ia), (Ib) or (II) as defined above or (Z)-3-(4-ethoxypyridin-3-yl)-2-(5-methoxy-1H-indol-3-yl)-acrylonitrile including any one of the disclosed embodiments; and/or a method for treating a lung disease in a subject in need thereof, comprising administering an effective amount of a pharmaceutical composition as defined above or any compound having the formula (I), (Ia), (Ib) or (II) as defined above or (Z)-3-(4-ethoxypyridin-3-yl)-2-(5-methoxy-1H-indol-3-yl)-acrylonitrile including any one of the disclosed embodiments; and/or a method for treating a pathology associated with dysregulation of MKlp2 or its pathway in a subject in need thereof, comprising administering an effective amount of a pharmaceutical composition as defined above or any compound having the formula (I), (Ia), (Ib) or (II) as defined above or (Z)-3-(4-ethoxypyridin-3-yl)-2-(5-methoxy-1H-indol-3-yl)-acrylonitrile including any one of the disclosed embodiments; and/or the use of any compound having the formula (I), (Ia), (Ib) or (II) as defined above or (Z)-3-(4-ethoxypyridin-3-yl)-2-(5-methoxy-1H-indol-3-yl)-acrylonitrile including any one of the disclosed embodiments, as a pharmacological research tool.

The term "cancer", as used herein, refers to the presence of cells possessing characteristics typical of cancer-causing cells, such as uncontrolled proliferation, immortality, metastatic potential, rapid growth and proliferation rate, and certain characteristic morphological features. The cancer may be solid tumor or hematopoietic tumor. Examples of cancer include, for example, leukemia, lymphoma, blastoma, carcinoma and sarcoma. More particular examples of such cancers include chronic myeloid leukemia, acute lymphoblastic leukemia, Philadelphia chromosome positive acute lymphoblastic leukemia (Ph+ ALL), squamous cell carcinoma, lung cancer, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, osteosarcoma, pancreatic cancer, glioblastoma multiforme, cervical cancer, stomach cancer, bladder cancer, hepatoma, breast cancer, oesophagal cancer, colon carcinoma, and head and neck cancer, gastric cancer, germ cell tumor, pediatric sarcoma, sinonasal natural killer, multiple myeloma, acute myelogenous leukemia (AML), chronic lymphocytic leukemia, mastocytosis and any symptom associated with mastocytosis. Preferably, the cancer is a colon cancer, a pancreatic cancer, a breast cancer, a lung cancer and a bladder cancer. More preferably, the cancer is a colon cancer, a pancreatic cancer and a bladder cancer. Optionally, the cancer is associated with a dysregulation of MKlp2 or its pathway. In particular, the cancer is associated with an overexpression of MKlp2.

As used herein, the term "treatment", "treat" or "treating" refers to any act intended to ameliorate the health status of patients such as therapy, prevention, prophylaxis and retardation of the disease. In certain embodiments, such term refers to the amelioration or eradication of a disease or symptoms associated with a disease. In other embodiments, this term refers to minimizing the spread or worsening of the disease resulting from the administration of one or more therapeutic agents to a subject with such a disease.

By "effective amount" it is meant the quantity of the pharmaceutical composition of the invention which prevents, removes or reduces the deleterious effects of the treated disease in mammals, including humans. It is understood that the administered dose may be adapted by those skilled in the art according to the patient, the pathology, the mode of administration, etc. For instance, the compounds of the invention may be used at a dose of 0.01 to 500 mg/kg of body weight/day. In a particular embodiment, the pharmaceutical composition according to the invention comprises 0.01 to 500 mg/kg of the compound of the invention. It is understood that the administered dose may be adapted by those skilled in the art according to the patient, the pathology, the mode of administration, etc.

The administration route can be topical, transdermal, oral, rectal, sublingual, intranasal, intrathecal, intratumoral or parenteral (including subcutaneous, intramuscular, intravenous and/or intradermal). Preferably, the administration route is parental, oral or topical. The pharmaceutical composition is adapted for one or several of the above-mentioned routes. The pharmaceutical composition, kit, product or combined preparation is preferably administered by injection or by intravenous infusion or suitable sterile solutions, or in the form of liquid or solid doses via the alimentary canal.

The pharmaceutical composition can be formulated as solutions in pharmaceutically compatible solvents or as emulsions, suspensions or dispersions in suitable pharmaceutical solvents or vehicles, or as pills, tablets or capsules that contain solid vehicles in a way known in the art. Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. Formulations for rectal administration may be in the form of a suppository incorporating the active ingredient and carrier such as cocoa butter, or in the form of an enema. Formulations suitable for parenteral administration conveniently comprise a sterile oily or aqueous preparation of the active ingredient which is preferably isotonic with the blood of the recipient. Every such formulation can also contain other pharmaceutically compatible and nontoxic auxiliary agents, such as, e.g. stabilizers, antioxidants, binders, dyes, emulsifiers or flavouring substances. The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof. The pharmaceutical compositions are advantageously applied by injection or intravenous infusion of suitable sterile solutions or as oral dosage by the digestive tract. Methods for the safe and effective administration of most of these chemotherapeutic agents are known to those skilled in the art. In addition, their administration is described in the standard literature.

The additional antitumoral drug can be selected in the non-exhaustive list of antitumoral agents consisting of an inhibitor of topoisomerases I or II, an anti-mitotic agent, a DNA alkylating agent, an anti-metabolic agent, a targeted agent such as a kinase inhibitor, and/or a therapeutical antibody designed to mediate cytotoxicity against the cancer cells or to modulate one of their key biological functions.

Anti-mitotic agents include, but are not limited to, paclitaxel, docetaxel and analogs such as larotaxel (also called XRP9881; Sanofi-Aventis), XRP6258 (Sanofi-Aventis), BMS-184476 (Bristol-Meyer-Squibb), BMS-188797 (Bristol-Meyer-Squibb), BMS-275183 (Bristol-Meyer-Squibb), ortataxel (also called IDN 5109, BAY 59-8862 or SB-T-101131; Bristol-Meyer-Squibb), RPR 109881A (Bristol-Meyer-Squibb), RPR 116258 (Bristol-Meyer-Squibb), NBT-287 (TAPESTRY), PG-paclitaxel (also called CT-2103, PPX, paclitaxel poliglumex, paclitaxel polyglutamate or Xyotax™), ABRAXANE® (also called Nab-Paclitaxel; ABRAXIS BIOSCIENCE), Tesetaxel (also called DJ-927), IDN 5390 (INDENA), Taxoprexin (also called docosahexanoic acid-paclitaxel; PROTARGA), DHA-paclitaxel (also called Taxoprexin®), and MAC-321 (WYETH).

Inhibitors of topoisomerases I and/or II include, but are not limited to, etoposide, topotecan, camptothecin, irinotecan, amsacrine, intoplicin, anthracyclines such as doxorubicin, epirubicin, daunorubicin, idarubicin and mitoxantrone. Inhibitors of Topoisomerase I and II include, but are not limited to, intoplicin.

DNA alkylating agent includes, but are not limited to, cisplatin, carboplatin and oxaliplatin. In a preferred embodiment, the DNA alkylating agent is cisplatin.

Anti-metabolic agents block the enzymes responsible for nucleic acid synthesis or become incorporated into DNA, which produces an incorrect genetic code and leads to apoptosis. Non-exhaustive examples thereof include, without limitation, folic acid antagonists, pyrimidine analogs, purine analogs and adenosine deaminase inhibitors, and more particularly Methotrexate, Floxuridine, Cytarabine, 6-Mercaptopurine, 6-Thioguanine, Fludarabine phosphate, Pentostatine, 5-fluorouracil, gemcitabine and capecitabine.

The anti-tumoral agent can be alkylating agents including, without limitation, nitrogen mustards, ethylenimine derivatives, alkyl sulfonates, nitrosoureas, metal salts and triazenes. Non-exhaustive examples thereof include Uracil mustard, Chlormethine, Cyclophosphamide (CYTOXAN®), Ifosfamide, Melphalan, Chlorambucil, Pipobroman, Triethylenemelamine, Triethylenethiophosphoramine, Busulfan, Carmustine, Lomustine, cisplatin, carboplatin, oxaliplatin, thiotepa, Streptozocin, Dacarbazine, and Temozolomide.

The anti-tumoral agent can also be a targeted agent, in particular a kinase inhibitor. The kinase may be selected from the group consisting of intracellular tyrosine or serine/threonine kinases, receptors tyrosine or serine/theonine kinase. For instance, the agents may have ability to inhibit angiogenesis based on the inhibitory activities on VEGFR and PDGFR kinases. In particular, the targeted agent can be selected among the multiple kinase inhibitor drugs which are already approved: Gleevec, which inhibits Abl, and Iressa and Tarceva, which both inhibit EGFR, Sorafenib (Nexavar, BAY 43-9006) which inhibits Raf, Dasatinib (BMS-354825) and Nilotinib (AMN-107, Tasigna) which also inhibits Abl, Lapatinib which also inhibits EGFR, Temsirolimus (Torisel, CCI-779) which targets the mTOR pathway, Sunitinib (Stuten, SU11248) which inhibits several targets including VEGFR as well as specific antibodies inactivating kinase receptors: Herceptin and Avastin.

The term "therapy", as used herein, refers to any type of treatment of cancer (i.e., antitumoral therapy), including an adjuvant therapy and a neoadjuvant therapy. Therapy comprises radiotherapy and therapies, preferably systemic therapies such as hormone therapy, chemotherapy, immunotherapy and monoclonal antibody therapy.

The term "adjuvant therapy", as used herein, refers to any type of treatment of cancer given as additional treatment, usually after surgical resection of the primary tumor, in a patient affected with a cancer that is at risk of metastasizing and/or likely to recur. The aim of such an adjuvant treatment is to improve the prognosis. Adjuvant therapies comprise radiotherapy and therapy, preferably systemic therapy, such as hormone therapy, chemotherapy, immunotherapy and monoclonal antibody therapy.

The term "hormone therapy" or "hormonal therapy" refers to a cancer treatment having for purpose to block, add or remove hormones. For instance, in breast cancer, the female hormones estrogen and progesterone can promote the growth of some breast cancer cells. So in these patients, hormone therapy is given to block estrogen and a non-exhaustive list commonly used drugs includes: Tamoxifen, Toremifene, Anastrozole, Exemestane, Letrozole, Goserelin/Leuprolide, Megestrol acetate, and Fluoxymesterone.

As used herein, the term "chemotherapeutic treatment" or "chemotherapy" refers to a cancer therapeutic treatment using chemical or biological substances, in particular using one or several antineoplastic agents.

The term "radiotherapeutic treatment" or "radiotherapy" is a term commonly used in the art to refer to multiple types of radiation therapy including internal and external radiation therapies or radioimmunotherapy, and the use of various types of radiations including X-rays, gamma rays, alpha particles, beta particles, photons, electrons, neutrons, radioisotopes, and other forms of ionizing radiations.

The term "therapeutical antibody" refers to any antibody having an anti-tumoral effect. Preferably, the therapeutical antibody is a monoclonal antibody. Therapeutic antibodies are generally specific for surface antigens, e.g., membrane antigens. Most preferred therapeutic antibodies are specific for tumor antigens (e.g., molecules specifically expressed by tumor cells), such as CD20, CD52, ErbB2 (or HER2/Neu), CD33, CD22, CD25, MUC-1, CEA, KDR, αVβ3, and the like. The therapeutical antibody include, but is not limited to, antibodies such as trastuzumab (anti-HER2 antibody), rituximab (anti-CD20 antibody), alemtuzumab, gemtuzamab, cetuximab, pertuzumab, epratuzumab, basiliximab, daclizumab, labetuzumab, sevirumab, tuvurimab, palivizumab, infliximab, omalizumab, efalizumab, natalizumab, clenoliximab, and bevacizumab.

The general term "viral infection" defines a condition caused by viruses. The term "HIV infection" more significantly defines a condition caused by the Human Immunodeficiency Virus (HIV), the term "HPV infection" more significantly defines a condition caused by the Human PapillomaVirus (HPV), and the term "HTLV infection" more significantly defines a condition caused by the Human T-cell Lymphotropic Virus (HTLV).

The pulmonary arterial hypertension (PAH) is a syndrome characterized by a progressive increase in pulmonary vascular resistance leading to right ventricular overload and eventually cardiac failure.

Preferably, the pathologies associated with dysregulation of MKlp2 or its pathway are Alzheimer's disease or Creutzfeldt-Jakob's disease.

Finally, the present invention concerns the use of a compound of the formula (I) as defined above as a research pharmacological tool, in particular as MKlp2 inhibitor. It can be used as a laboratory tool or in a screening method.

FIGURES

FIG. 1: Stability of compound 63 in mouse and human plasma.

Figure 2:
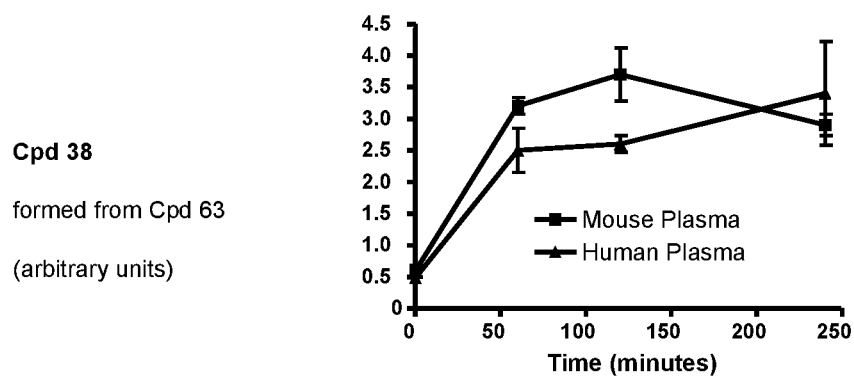

FIG. 2: Amount of formed compound 38 from compound 63 in mouse and human plasma.

Figure 3:
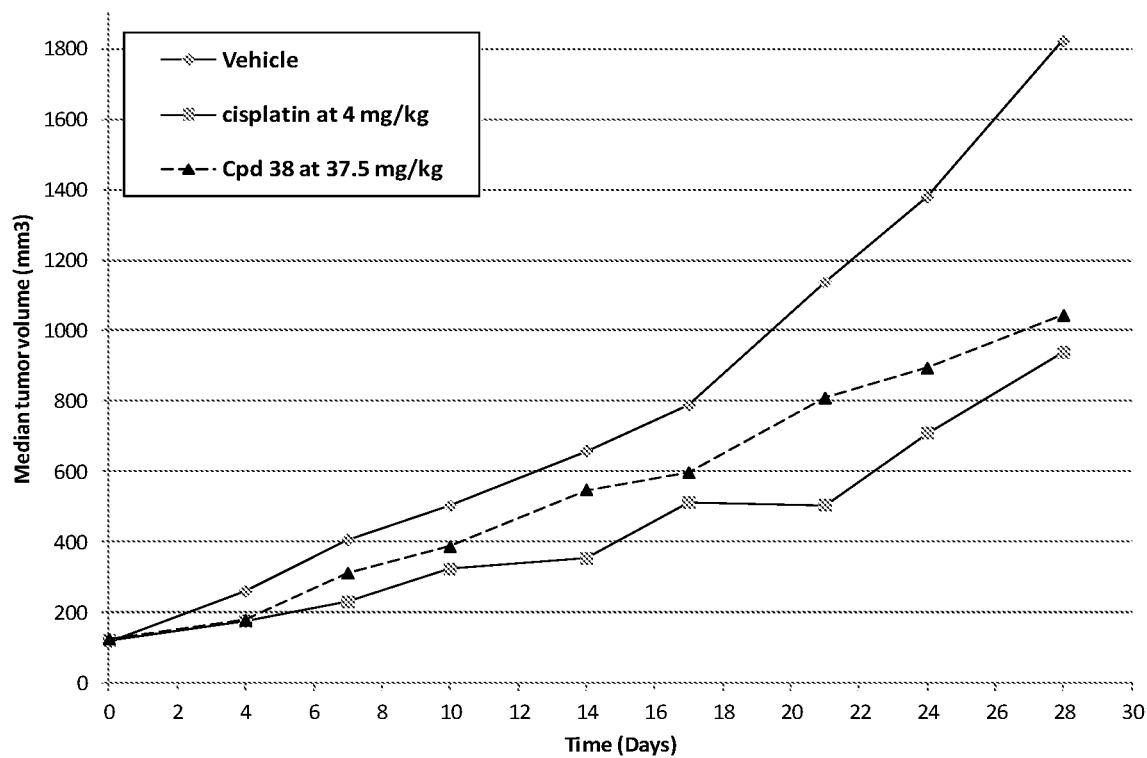

FIG. 3: Evaluation of anti-tumor activity of compound 38 in nude mice bearing subcutaneous human colon HCT-116 xenografts.

Figure 4:
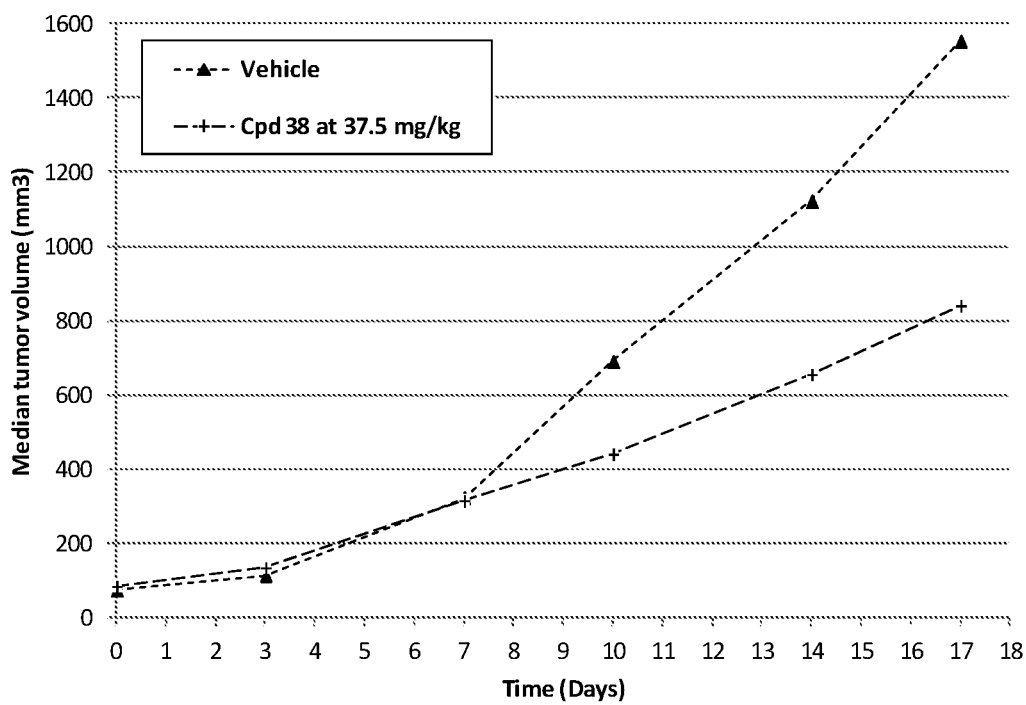

FIG. 4: Evaluation of anti-tumor activity of compound 38 in nude mice bearing subcutaneous non small cell lung carcinoma NCl-H460 xenografts.

EXAMPLES

The following examples illustrate in detail the preparation of compounds of formula (I) according to the invention. The structures of the products obtained have been confirmed by NMR spectra.

Starting compounds and reactants, unless otherwise indicated, are commercially available or described in literature, or can be prepared according to methods described in literature or known to one skilled in the art.

Example 1: Preparation of Starting Indoles and Aldehydes

A) Syntheses of Starting Indoles

Tert-butyl-5-bromo-3-(cyanomethyl)-1H-indole-1-carboxylate

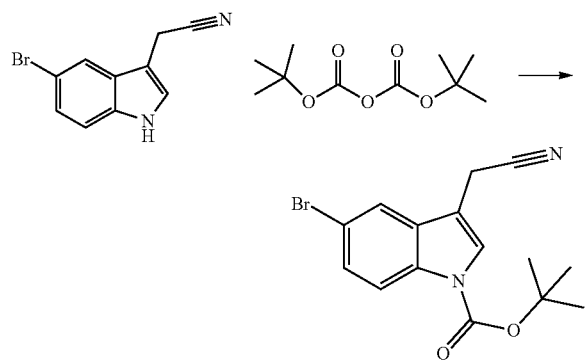

In a 250 mL pear flask, 2-(5-bromo-1H-indol-3-yl)acetonitrile (1.76 g, 7.49 mmol) was dissolved in 70 mL of acetonitrile to give a colorless solution. Di-tert-butyl-dicarbonate (1.922 mL, 8.98 mmol) and DMAP (0.091 g, 0.749 mmol) were added to the solution and the reaction mixture was stirred at RT for 1 h.

TLC: 100% Dichloromethane showed no more starting material.

Then the reaction mixture was poured into 50 mL of water, extracted with 2×50 mL of ethyl acetate and the combined organic layer was successively washed with 1×50 mL of Brine, dried over $Na_2SO_4$, filtered and concentrated in vacuo to give a yellow oil which crystallized upon standing to give a yellow solid, m=2.59 g (Yield: 99%).

APCI-MS: (M–H)=234

$^1$H NMR (300 MHz, DMSO-$d_6$) δ ppm: 8.00 (d, J=8.8 Hz, 1H), 7.91 (d, J=1.8 Hz, 1H), 7.73 (s, 1H), 7.53 (dd, J=8.8, 2.0 Hz, 1H), 4.12 (d, J=0.9 Hz, 2H), 1.61 (s, 9H).

Tert-butyl-5-chloro-3-(cyanomethyl)-1H-indole-1-carboxylate is obtained according to the same procedure as for Tert-butyl-5-bromo-3-(cyanomethyl)-1H-indole-1-carboxylate.

Tert-butyl 6-X-3-(cyanomethyl)-1H-indole-1-carboxylate

Synthesis of 2-(6-X-1H-indol-3-yl)acetonitrile (X=bromo, fluoro or chloro)

A mixture of 6-X-1-H-indole-3-carbaldehyde (1 eq), formamide (9 mL/mmol), MeOH (9 mL/mmol) and $NaBH_4$ (3 eq) were stirred 1 h at room temperature. KCN (10 eq) was then added and the resulting mixture was stirred 5 h at 60° C. The reaction was quenched with aqueous NaCl and extracted with $CHCl_3$, dried over $Na_2SO_4$, filtrated and concentrated. The residue was purified by silicagel chromatography ($CH_2Cl_2$/MeOH, 100:0 to 90:10) to give the title compound.

2-(6-bromo-1H-indol-3-yl)acetonitrile

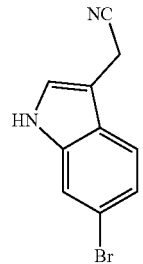

6-bromo-1H-indole-3-carbaldehyde (200.0 mg), formamide (8 mL), $NaBH_4$ (101.0 mg), MeOH (8 ml). KCN (580.0 mg). Aspect of the pure product: white solid. (Yield: 67%).

$^1$H NMR ($CDCl_3$, 300 MHz) δ ppm: 8.21 (s, 1H), 7.59 (s, 1H), 7.48 (d, 1H), 7.31 (d, 1H), 7.24 (s, 1H), 3.84 (s, 1H).

2-(6-fluoro-1H-indol-3-yl)acetonitrile

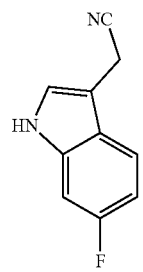 [SMILES: N#CCc1c[nH]c2cc(F)ccc12]

6-fluoro-1H-indole-3-carbaldehyde (200.0 mg), formamide (10 mL), $NaBH_4$ (138.0 mg), MeOH (10 ml). KCN (791.0 mg). Aspect of the pure product: white solid. (Yield: 75%).

$^1$H NMR ($CDCl_3$, 300 MHz) δ ppm: 8.48 (s, 1H), 7.53-7.50 (m, 1H), 7.14 (s, 1H), 7.09 (d, 1H), 7.0-6.96 (m, 1H), 3.80 (s, 2H).

2-(6-chloro-1H-indol-3-yl)acetonitrile

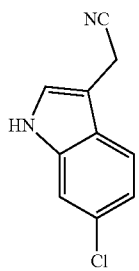 [SMILES: N#CCc1c[nH]c2cc(Cl)ccc12]

6-chloro-1H-indole-3-carbaldehyde (200.0 mg), formamide (10 mL), NaBH$_4$ (126.0 mg), MeOH (10 ml). KCN (722.0 mg). Aspect of the pure product: white solid. (Yield: 81%).
$^1$H NMR (CDCl$_3$, 300 MHz) δ ppm: 8.34 (s, 1H), 7.50 (d, 1H), 7.38 (s, 1H), 7.24-7.16 (m, 1H), 7.14 (d, 1H), 3.82 (s, 2H).

Synthesis of Tert-butyl 6-X-3-(cyanomethyl)-1H-indole-1-carboxylate

To a solution of 2-(6-X-1H-indol-3-yl)acetonitrile in CH$_2$Cl$_2$, was added Boc$_2$O (eq) and DMAP (eq). The resulting mixture was stirred 12 h at room temperature, then diluted with CH$_2$Cl$_2$, washed with water and concentrated to give the title compound.

Tert-butyl 6-bromo-3-(cyanomethyl)-1H-indole-1-carboxylate

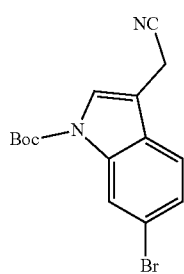 [SMILES: CC(C)(C)OC(=O)n1cc(CC#N)c2ccc(Br)cc21]

2-(6-bromo-1H-indol-3-yl)acetonitrile (138.0 mg), DMAP (3.0 mg), Boc$_2$O (152.0 mg). CH$_2$Cl$_2$ (2.8 mL). 12 h at room temperature. Aspect of the pure product: white solid. (Yield: 90%).
$^1$H NMR (CDCl$_3$, 300 MHz) δ ppm: 8.41 (s, 1H), 7.62 (s, 1H), 7.47-7.36 (m, 2H), 3.78 (s, 2H), 1.70 (s, 9H).

Tert-butyl 6-fluoro-3-(cyanomethyl)-1H-indole-1-carboxylate

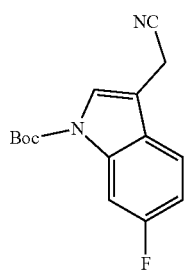 [SMILES: CC(C)(C)OC(=O)n1cc(CC#N)c2ccc(F)cc21]

2-(6-fluoro-1H-indol-3-yl)acetonitrile (160.0 mg), DMAP (4.3 mg), Boc$_2$O (238.0 mg). CH$_2$Cl$_2$ (4.4 mL). 12 h at room temperature. Aspect of the pure product: white solid. (Yield: 98%).
$^1$H NMR (CDCl$_3$, 300 MHz) δ ppm: 7.91 (d, 1H), 7.63 (s, 1H), 7.50-7.42 (m, 1H), 7.07 (td, 1H), 3.78 (s, 2H), 1.69 (s, 9H).

Tert-butyl 6-chloro-3-(cyanomethyl)-1H-indole-1-carboxylate

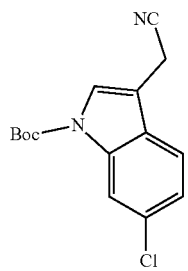 [SMILES: CC(C)(C)OC(=O)n1cc(CC#N)c2ccc(Cl)cc21]

2-(6-chloro-1H-indol-3-yl)acetonitrile (168.0 mg), DMAP (6.0 mg), Boc$_2$O (233.0 mg). CH$_2$Cl$_2$ (4.0 mL). Aspect of the pure product: white solid. (Yield: 86%).
$^1$H NMR (CDCl$_3$, 300 MHz) δ ppm: 8.25 (s, 1H), 7.64 (s, 1H), 7.45 (d, 1H), 7.29 (d, 1H), 3.77 (s, 2H), 1.70 (s, 9H).

B) Syntheses of Starting Aldehydes

3-formyl-4-methoxybenzonitrile

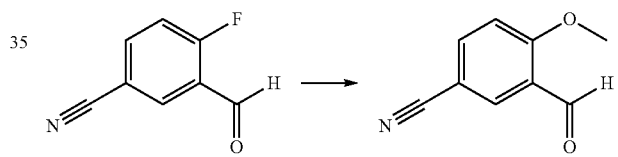

In a 10 mL reactor flask, 4-fluoro-3-formylbenzonitrile (900 mg, 6.04 mmol) was dissolved under argon in 2 mL of methanol. Sodium methoxide (1.232 mL, 6.64 mmol) was added and the reaction mixture was heated at reflux for 2 h.
TLC showed no more starting material.
The reaction mixture was poured into 10 mL of water. The resulting solid was filtered, washed with water, DIPE and dried in vacuo. The residue was purified by flash chromatography, eluted with a gradient from petroleum ether to MTBE give 587 mg of a grey solid (Yield: 59%).
LC-MS: 98%
$^1$H NMR (300 MHz, DMSO-d$_6$) δ ppm: 10.28 (s, 1H), 8.12 (dd, J=8.8, 2.2 Hz, 1H), 8.05 (d, J=2.1 Hz, 1H), 7.43 (d, J=8.8 Hz, 1H), 4.01 (s, 3H).

3-formyl-4-(1H-1,2,4-triazol-1-yl)benzonitrile

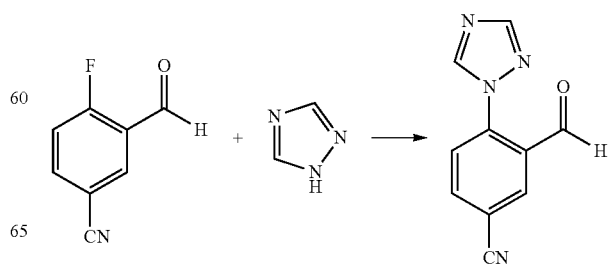

In sealed microwave reactors, 4-fluoro-3-formylbenzonitrile (850 mg, 5.7 mmol) was dissolved in acetonitrile (15 mL), 1H-1,2,4-triazol (590 mg, 8.55 mmol, 1.5 eq) and $K_2CO_3$ (1575 mg, 11.39 mmol, 2 eq) were added to give a colorless suspension. Then the reaction mixture was stirred and heated at 80° C. for 5 min.

The reaction mixture was poured into 20 mL of water, extracted with 2×20 mL of EtOAc. The combined organic layers were washed with 1×20 mL of water, 1×20 mL of brine, dried over $Na_2SO_4$, filtered and concentrated in vacuo to give an orange solid, m=983 mg.

The solid was triturated with dichloromethane and petroleum ether, filtered and dried in vacuo at 45° C. overnight to give 493 mg of a brown powder (Yield: 43%).

APCI-MS: $(M+H)^+$=199

$^1$H NMR (300 MHz, DMSO-$d_6$) δ ppm: 10.01 (s, 1H), 9.33 (s, 1H), 8.46-8.29 (m, 3H), 8.05 (d, J=9.0 Hz, 1H).

4-(1H-1,2,4-triazol-1-yl)nicotinaldehyde

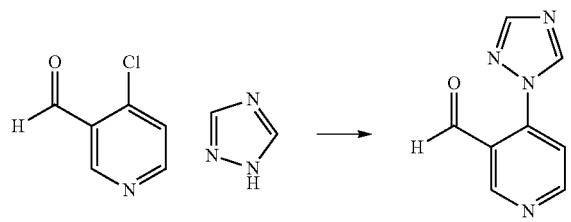

Aspect of the product: yellow solid (Yield: 49%) APCI-MS: $(M+H)+$=175

$^1$H NMR (300 MHz, DMSO-$d_6$) δ ppm: 10.20 (s, 1H), 9.39 (s, 1H), 8.99-8.91 (m, 2H), 8.39 (s, 1H), 7.90 (d, J=5.5 Hz, 1H).

3-formyl-4-(4-fluorophenylthio)benzonitrile

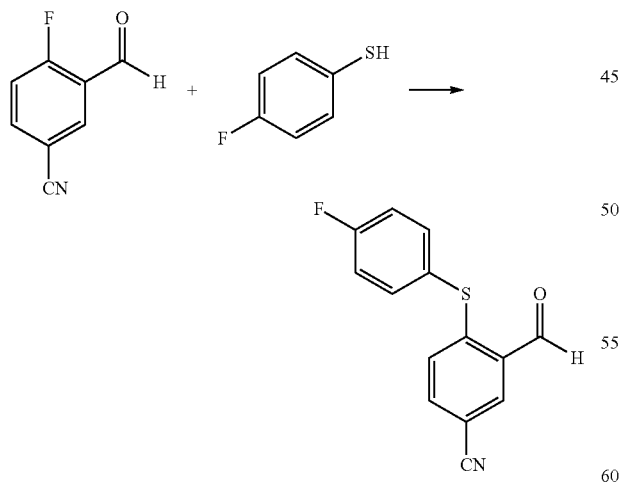

In a 50 mL round-bottomed flask, 4-fluoro-3-formylbenzonitrile (900 mg, 5.73 mmol) and potassium carbonate (872 mg, 6.31 mmol) were suspended in DMF (10 mL) to give a yellow suspension. Then 4-fluorobenzenethiol (0.654 mL, 6.02 mmol) was added and the reaction mixture heated at 70° C. for 18 h. The reaction mixture was poured into water. The solid was filtered, washed with water and with a few amount of DIPE then dried in vacuo to give 1.44 g of a pale yellow solid (Yield: 97%).

APCI-MS: $(M+H)^+$=257

$^1$H NMR (300 MHz, DMSO-$d_6$) δ ppm: 10.12 (s, 1H), 8.49 (d, J=1.9 Hz, 1H), 7.85 (dd, J=8.5, 2.0 Hz, 1H), 7.71-7.62 (m, 2H), 7.43 (ddd, J=10.9, 6.0, 2.6 Hz, 2H), 6.80 (d, J=8.5 Hz, 1H).

The following examples were prepared according to the previous method.

4-(ethylthio)-3-formylbenzonitrile

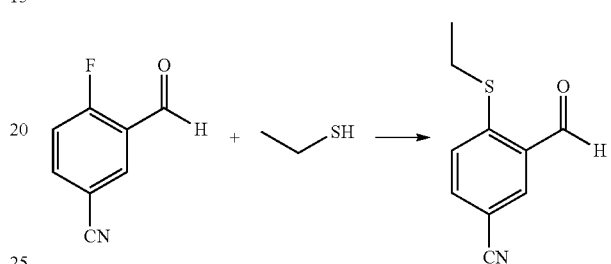

Aspect of the product: yellow solid (Yield: 83%)

$^1$H NMR (300 MHz, DMSO-$d_6$) δ ppm: 10.07 (s, 1H), 8.38 (d, J=1.9 Hz, 1H), 7.99 (dd, J=8.4, 1.9 Hz, 1H), 7.63 (d, J=8.5 Hz, 1H), 3.08 (q, J=7.4 Hz, 2H), 1.30 (t, J=7.3 Hz, 3H).

4-(dimethylamino)-3-formylbenzonitrile

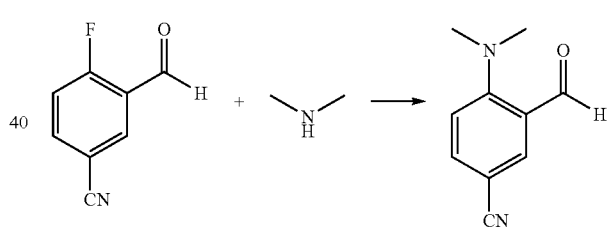

Aspect of the product: orange solid (Yield: 96%)

APCI-MS: $(M+H)^+$=175

$^1$H NMR (300 MHz, DMSO-$d_6$) δ ppm: 9.88 (s, 1H), 8.07 (d, J=2.2 Hz, 1H), 7.72 (dd, J=8.9, 2.2 Hz, 1H), 7.09 (d, J=8.9 Hz, 1H), 2.99 (s, 6H).

4-(diethylamino)-3-formylbenzonitrile

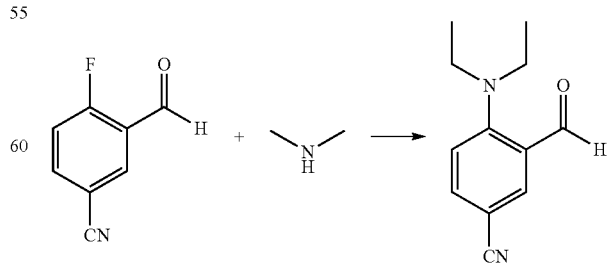

Aspect of the product: yellow solid (Yield: 83%)

APCI-MS: $(M+H)^+$=203

$^1$H NMR (300 MHz, DMSO-d$_6$) δ ppm: 9.91 (s, 1H), 8.00 (d, J=2.2 Hz, 1H), 7.78 (dd, J=8.9, 2.2 Hz, 1H), 7.21 (d, J=8.9 Hz, 1H), 3.44-3.35 (m, 4H), 1.11 (t, J=7.0 Hz, 6H).

4-dimethylamino-3-formyl-pyridine

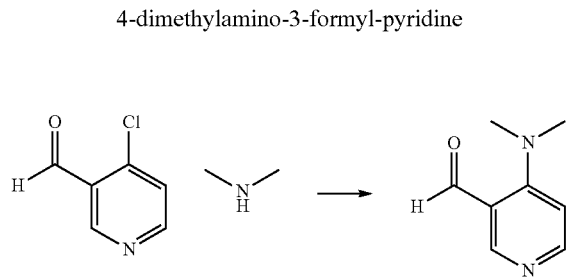

A mixture of 4-chloronicotinaldehyde (500 mg, 3.53 mmol), potassium carbonate (976 mg, 7.06 mmol) and dimethylamine in THF (2.65 mL, 5.30 mmol) was heated at 80° C. for 3 hours.

TLC (eluent EtOAc) showed no more starting material.

The reaction mixture was concentrated under pressure. Purification by flash chromatography on silica gel column (eluant: CH$_2$Cl$_2$/MeOH 90/10) yielded 0.48 g of a pale yellow solid (Yield: 90%).

APCI-MS: (M+H)$^+$=151

$^1$H NMR (300 MHz, DMSO-d$_6$) δ ppm: 9.93 (s, 1H), 8.60 (s, 1H), 8.23 (d, J=6.1 Hz, 1H), 6.87 (d, J=6.2 Hz, 1H), 2.99 (s, 6H).

4-fluorophenoxy-3-formylpyridine

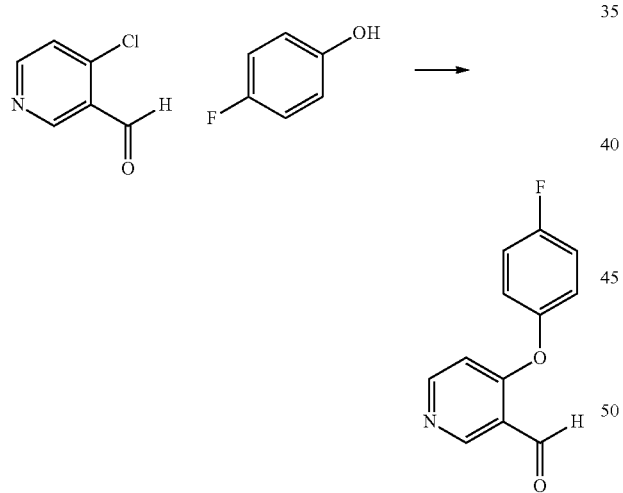

To a solution of 4-fluorophenol (455 mg, 4.06 mmol) in THF [5 mL] was added HNa (162 mg, 4.06 mmol). After stirring for 0.5 hour, 4-chloronicotinaldehyde (500 mg, 3.53 mmol) was added and the reaction mixture was heated at 65° C. for 3 hours.

Then the reaction mixture was diluted with water and brine, extracted with MTBE, dried over MgSO$_4$ and concentrated under reduced pressure to give 617 mg of an oily compound (Yield: 64%).

APCI-MS: (M+H)$^+$=218

The following example was prepared as the previous method.

4-fluorophenoxy-3-formylbenzonitrile

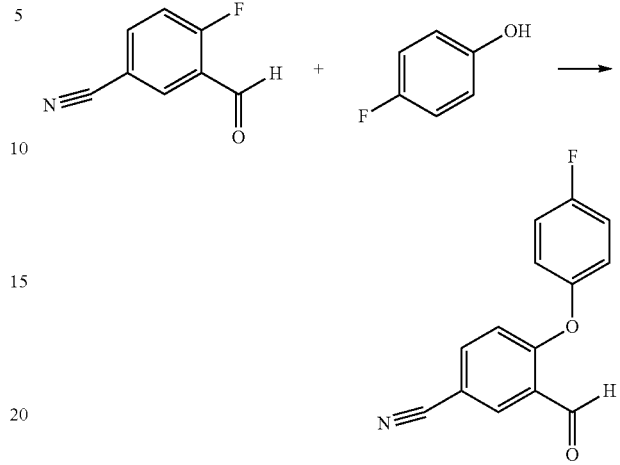

Aspect of the product: yellow solid (Yield: 64%)

APCI-MS: (M–H)=240

$^1$H NMR (300 MHz, DMSO-d$_6$) δ ppm: 10.41 (s, 1H), 8.23 (d, J=2.2 Hz, 1H), 8.03 (dd, J=8.8, 2.2 Hz, 1H), 7.40-7.30 (m, 4H), 6.95 (d, J=8.8 Hz, 1H).

4-fluorophenylthio-3-formylpyridine

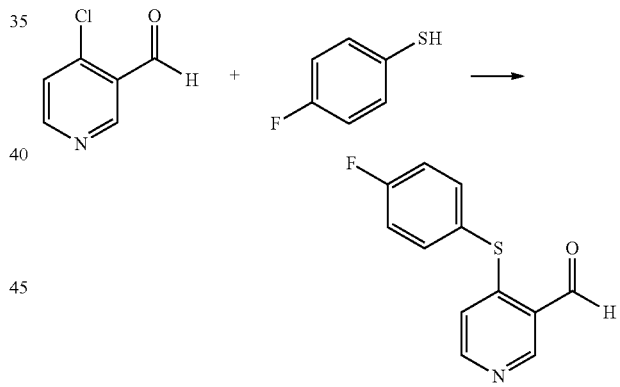

A mixture of 4-chloronicotinaldehyde (500 mg, 3.53 mmol), potassium carbonate (537 mg, 3.89 mmol) and 4-fluorobenzenethiol (0.403 mL, 3.71 mmol) in DMF (10 mL) was heated at 70° C. for 1 h.

The reaction mixture was quenched with water, extracted with 3×20 mL of AcOEt, the combined organic were washed with brine, dried over Na$_2$SO$_4$, filtered and concentrated under vacuum to give a brown oil. The oil was triturated with 5 mL of DIPE to give 0.46 g of a beige solid (Yield: 55%).

APCI-MS: (M+H)$^+$=234

$^1$H NMR (300 MHz, DMSO-d$_6$) δ ppm: 10.19 (s, 1H), 9.03 (s, 1H), 8.45 (d, J=5.6 Hz, 1H), 7.69 (dd, J=8.5, 5.5 Hz, 2H), 7.45 (t, J=8.7 Hz, 2H), 6.61 (d, J=5.6 Hz, 1H).

The following examples were prepared as the previous method.

4-(pyridin-2-ylthio)nicotinaldehyde

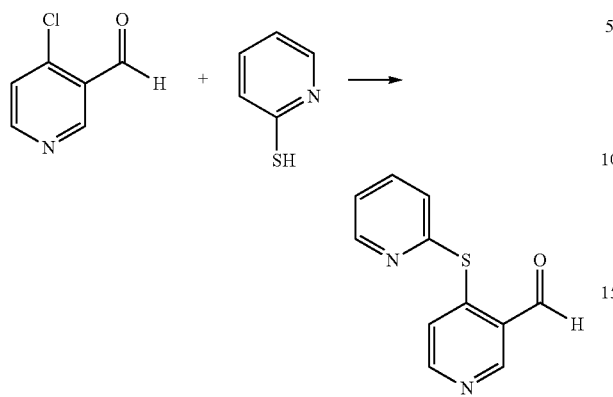

Aspect of the product: yellow solid (Yield: 61%)
APCI-MS: (M+H)$^+$=217
$^1$H NMR (300 MHz, DMSO-d$_6$) δ ppm: 10.18 (s, 1H), 9.04 (s, 1H), 8.68 (d, J=3.7 Hz, 1H), 8.51 (d, J=5.5 Hz, 1H), 7.95 (td, J=7.7, 1.9 Hz, 1H), 7.74 (d, J=7.8 Hz, 1H), 7.51 (dd, J=6.5, 4.8 Hz, 1H), 7.00 (d, J=5.5 Hz, 1H).

3-formyl-4-(4-trifluorophenyl)benzonitrile

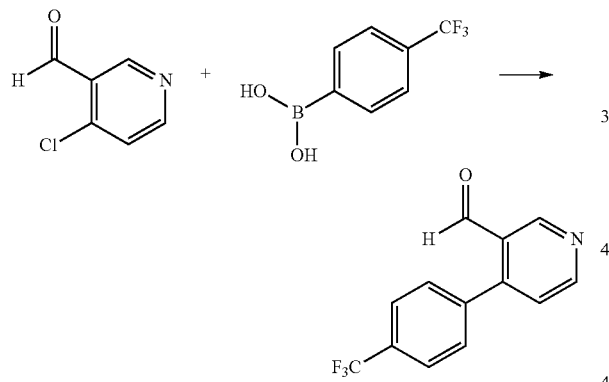

In a 50 mL pear flask, magnetic stirrer, 4-chloronicotinaldehyde (500 mg, 3.53 mmol), 4-trifluoromethyl)phenylboronic acid (671 mg, 3.53 mmol), triphenylphosphine (55.6 mg, 0.212 mmol), palladium(II) acetate (47.6 mg, 0.212 mmol) and potassium carbonate (976 mg, 7.06 mmol) were added successively followed by 1,2-dimethoxyethane (10 mL) and water (2.5 mL). The reaction mixture was stirred and heated at 85° C. for 18 hours (LC/MS showed no starting material).

20 mL of water and 20 mL of ethyl acetate were added. The mixture was filtered over Celite and the cake rinsed with 20 mL of ethyl acetate. Organic phases were washed twice with brine, dried over sodium sulfate, filtered and the solvent was removed to give 890 mg of an oil.

The crude oil was purified by flash chromatography on SiO$_2$, eluted with 100% dichloromethane then 95/5 dichloromethane/acetone to give 370 mg of a grey solid (Yield: 42%).

APCI-MS: (M+H)$^+$=252
$^1$H NMR (300 MHz, DMSO-d$_6$) δ ppm: 10.00 (s, 1H), 9.08 (s, 1H), 8.90 (d, J=5.1 Hz, 1H), 7.92 (d, J=8.1 Hz, 2H), 7.78 (d, J=8.0 Hz, 2H), 7.61 (dd, J=5.1, 0.6 Hz, 1H).

The following example was prepared as the previous method.

4-(furan-3-yl)nicotinaldehyde

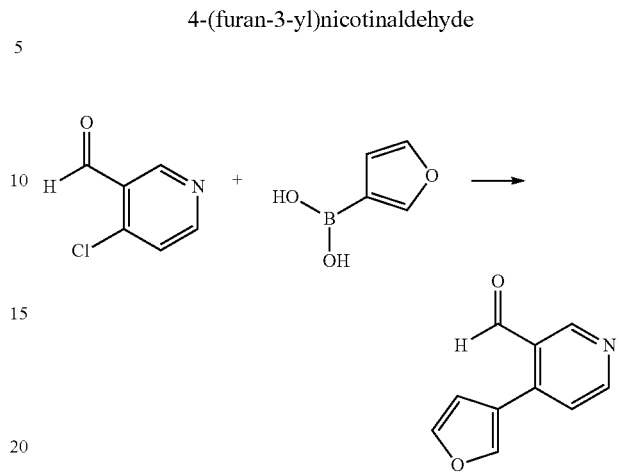

Aspect of the product: yellow solid (Yield: 64%)
LC-MS: (M+H)$^+$=174
$^1$H NMR (300 MHz, DMSO-d$_6$) δ ppm: 10.24 (s, 1H), 8.96 (s, 1H), 8.78 (s, 1H), 8.25 (s, 1H), 7.90 (s, 1H), 7.62 (s, 1H), 6.99 (s, 1H).

Preparation of Examples 2 to 53

Method A: Knoevenagel Condensation

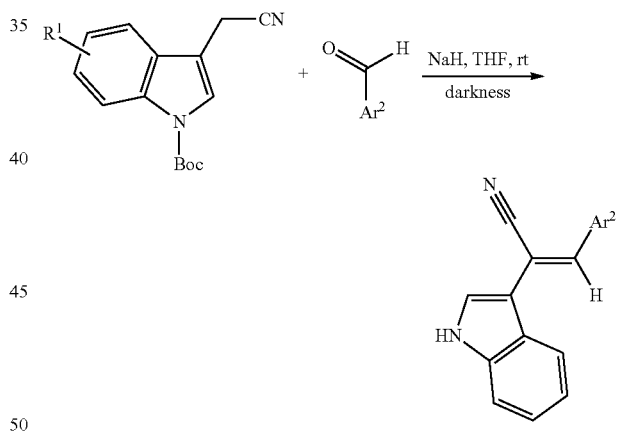

To a solution of cyanomethyl-indole-1-carboxylic acid tert-butyl ester (1 eq.) in THF was added sodium hydride (1.5 eq.) under an argon atmosphere. The reaction apparatus was protected from light and the mixture stirred at room temperature for 1 hour. Then the reaction mixture was cooled to 0° C. and the aldehyde (1.2 eq.) was added in portions.

The mixture was stirred at room temperature for 24 or 48 hours, then quenched with saturated ammonium chloride aqueous solution and extracted with AcOEt. The combined organic layers were dried over MgSO$_4$ and evaporated under vacuo. When the desired compound protected with a Boc group remained as a side product of the reaction, the reaction mixture was treated with a solution of HCl in dioxane or an aqueous solution of NaOH 1N to complete the Boc deprotection. Then the crude residue was triturated with a minimum of solvent (MeOH or CH$_2$Cl$_2$ or Et$_2$O), filterated, washed with Et$_2$O, and dried in vacuo for 12 hours (in dark) to afford the corresponding acrylonitrile.

Method B: SN$_{AR}$ reactions from (Z)-2-(5-methoxy-1H-indol-3-yl)-3-(4-chloro-3-yl)acrylonitrile or (Z)-2-(5-Bromo-1H-indol-3-yl)-3-(4-chloro-3-yl)acrylonitrile To a solution of 4-chloropyridine derivative (Z)-2-(5-methoxy-1H-indol-3-yl)-3-(4-chloro-3-yl)acrylonitrile or (Z)-2-(5-Bromo-1H-indol-3-yl)-3-(4-chloro-3-yl)acrylonitrile (1 eq.) in MeOH, EtOH or isopropanol was added KOH (2 to 5 eq.) under an argon atmosphere. The reaction apparatus was protected from light and the mixture was refluxed overnight. The mixture was diluted with AcOEt, washed with water then brine. The organic layer was dried over MgSO$_4$ and reduced in vacuo. The crude product was purified by trituration with AcOEt or by flash chromatography to afford the SN$_{AR}$ derivative.

Method C: SN$_{AR}$ reactions from (Z)-2-(5-methoxy-1H-indol-3-yl)-3-(4-chloro-3-yl)acrylonitrile or (Z)-2-(5-Bromo-1H-indol-3-yl)-3-(4-chloro-3-yl)acrylonitrile To a solution of 4-chloropyridine derivative-(Z)-2-(5-Bromo-1H-indol-3-yl)-3-(4-chloro-3-yl)acrylonitrile (1 eq.) in DMF was added NaSMe or NaSEt (2 eq.) under an argon atmosphere. The reaction apparatus was protected from light and the mixture was stirred overnight at room temperature. The mixture was diluted with AcOEt, washed with water then brine. The organic layer was dried over MgSO$_4$ and reduced in vacuo. The crude product was purified by trituration with AcOEt to afford the SN$_{AR}$ derivative.

Method D: SN$_{AR}$ reactions from (Z)-2-(5-methoxy-1H-indol-3-yl)-3-(4-chloro-3-yl)acrylonitrile or (Z)-2-(5-Bromo-1H-indol-3-yl)-3-(4-chloro-3-yl)acrylonitrile To a solution of 4-chloropyridine derivative (Z)-2-(5-methoxy-1H-indol-3-yl)-3-(4-chloro-3-yl)acrylonitrile or (1 eq.) in DMF were added arylthiol (1.1 eq.) and sodium or potassium carbonate (2 eq.) under an argon atmosphere. The reaction apparatus was protected from light and the mixture was stirred overnight at room temperature. The mixture was diluted with AcOEt, washed with water then brine. The organic layer was dried over MgSO$_4$ and reduced in vacuo. The crude product was purified by trituration with AcOEt to afford the SN$_{AR}$ derivative.

Method E: E Isomers

Z isomers were dissolved in ethanol and subjected to a 150 W halogen lamp with a continuous argon flux until there was no more starting material (TLC). The solution was then concentrated and the residue was purified by C18 chromatography to give the title compound.

Method F: Synthesis of (Z)-2-(6-X-1H-indol-3-yl)-3-(4-methoxypyridin-3-yl)acrylonitrile To a solution of tert-butyl 6-X-3-(cyanomethyl)-1H-indole-1-carboxylate (1 eq) in THF, was added NaH (eq). The resulting mixture was stirred 10 min at room temperature and 4-methoxynicotinaldehyde (1.3 eq) was added with one drop of DMF. The mixture was stirred at room temperature hidden from light. The reaction was quenched with aqueous NH$_4$Cl and extracted with AcOEt, dried over Na$_2$SO$_4$, filtrated and concentrated. The residue was dissolved with THF and NaOH 2.5 M was added. The system was stirred at room temperature hidden from light, diluted with AcOEt, dried over Na$_2$SO$_4$, filtrated and concentrated. The residue was taken off with a minimal amount of AcOEt and filtrated to give the title compound.

Method G: Synthesis of (Z)-3-(2-(5-X-1H-indol-3-yl)-2-cyanovinyl)-4-methoxypyridine 1-oxide To a solution of (Z)-2-(5-X-1H-indol-3-yl)-3-(4-methoxypyridin-3-yl)acrylonitrile in THF was added m-CPBA (1 eq), the resulting mixture was stirred 12 h at room temperature, hidden from light and a new portion of m-CPBA (0.5 eq) was added. After additional 4 h of stirring, the mixture was concentrated and the residue was triturated in AcOEt and filtrated to give the title compound.

Method H: Synthesis of (Z)-3-(2-(5-X-1H-indol-3-yl)-2-cyanovinyl)-4-(trifluoromethoxy) benzonitrile To a solution of tert-butyl 5-X-3-(cyanomethyl)-1H-indole-1-carboxylate (1 eq) in THF, was added NaH (3 eq). The resulting mixture was stirred 10 min at room temperature and 3-formyl-4-(trifluoromethoxy)benzonitrile (1 eq) was added with one drop of DMF. The mixture was stirred at room temperature hidden from light. The reaction was quenched with aqueous NH$_4$Cl and extracted with AcOEt, dried over Na$_2$SO$_4$, filtrated and concentrated. The residue was dissolved with THF and NaOH 2.5 M was added. The system was stirred at room temperature hidden from light, diluted with AcOEt, dried over Na$_2$SO$_4$, filtrated and concentrated. The residue was purified by silicagel chromatography (CH$_2$Cl$_2$/MeOH, 100:0 to 90:10) to give the title compound.

Example 2

(Z)-3-(4-ethoxypyridin-3-yl)-2-(5-methoxy-1H-indol-3-yl)acrylonitrile

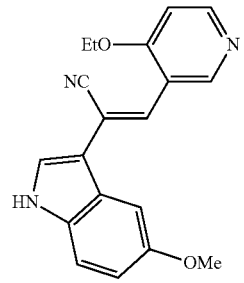 [SMILES: CCOc1ccncc1/C=C(\C#N)c1c[nH]c2ccc(OC)cc12]

Method B (Z)-2-(5-methoxy-1H-indol-3-yl)-3-(4-chloro-3-yl)acrylonitrile (50 mg), KOH (45 mg) and EtOH (1.5 mL). Trituration with AcOEt. Aspect of the pure product: yellow solid. (Yield: 67%).
ESI-MS: (M+H)$^+$=320

¹H NMR (Acetone-d₆, 300 MHz) δ ppm: 9.05 (s, 1H), 8.47 (d, J=5.8 Hz, 1H), 7.81 (s, 1H), 7.75 (s, 1H), 7.49 (d, J=2.3 Hz, 1H), 7.47 (d, J=9.0 Hz, 1H), 7.11 (d J=5.8 Hz, 1H), 6.93 (dd, J=9.0 Hz, J=2.3 Hz, 1H), 4.40 (q, J=7.0 Hz, 1H), 3.88 (s, 3H), 1.49 (t, J=7.0 Hz, 1H).

Example 3

(Z)-2-(5-chloro-1H-indol-3-yl)-3-(4-chloropyridin-3-yl)acrylonitrile

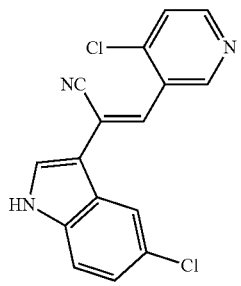 [SMILES: N#C/C(=C\c1cnccc1Cl)c1c[nH]c2ccc(Cl)cc12]

Method A tert-butyl 5-chloro-3-(cyanomethyl)-1H-indole-1-carboxylate (670 mg). Sodium hydride (138 mg). THF 17 mL. 4-chloronicotinaldehyde (457 mg). Trituration of the crude product with MeOH. Aspect of the pure product orange solid. (Yield: 38%) ESI-MS: (M+H)⁺=314

¹H NMR (DMSO-d₆, 300 MHz) δ ppm: 12.1 (s, 1H), 9.05 (s, 1H), 8.6 (d, 1H), 8.06 (d, 1H), 8.03 (d, 1H), 7.8 (s, 1H), 7.75 (d, 1H), 7.57 (dd, 1H), 7.3 (dd, 1H).

Example 4

(Z)-2-(5-bromo-1H-indol-3-yl)-3-(4-chloropyridin-3-yl)acrylonitrile

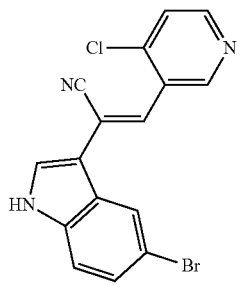 [SMILES: N#C/C(=C\c1cnccc1Cl)c1c[nH]c2ccc(Br)cc12]

Method A tert-butyl 5-bromo-3-(cyanomethyl)-1H-indole-1-carboxylate (600 mg). Sodium hydride (100 mg). THF 17 mL. 4-chloronicotinaldehyde (355 mg). Trituration of the crude product with dichloromethane and then washed with methanol and ether. Aspect of the pure product orange brown solid. (Yield: 50%).

ESI-MS: (M+H)⁺=358

¹H NMR (DMSO-d₆, 300 MHz) δ ppm: 12.1 (s, 1H), 9.03 (s, 1H), 8.62 (d, 1H), 8.2 (d, 1H), 8.0 (d, 1H), 7.8 (s, 1H), 7.76 (d, 1H), 7.55 (d, 1H), 7.4 (dd, 1H).

Example 5

(Z)-2-(5-bromo-1H-indol-3-yl)-3-(4-methoxypyridin-3-yl)acrylonitrile

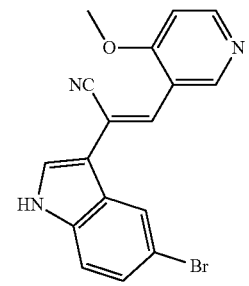 [SMILES: COc1ccncc1/C=C(\C#N)c1c[nH]c2ccc(Br)cc12]

Method B (Z)-2-(5-Bromo-1H-indol-3-yl)-3-(4-chloro-3-yl)acrylonitrile (80 mg), KOH (25 mg), MeOH (5 mL) and THF (2 mL). The mixture was refluxed for 24 hours. Purification by flash chromatography (CH₂Cl₂/MeOH 100/0 to 96/3). Aspect of the pure product: yellow solid. (Yield: 66%).

ESI-MS: (M+H)⁺=354

¹H NMR (DMSO-d₆, 300 MHz) δ ppm: 11.96 (s, 1H), 8.83 (s, 1H), 8.52 (d, J=8.8 Hz, 1H), 8.09 (d, J=1.9 Hz, 1H), 7.90 (d, J=2.6 Hz, 1H), 7.68 (s, 1H), 7.48 (d, J=8.7 Hz, 1H), 7.36 (dd, J=8.7 Hz, J=1.9 Hz, 1H), 7.20 (d, J=5.8 Hz, 1H), 3.95 (s, 3H).

Example 5b (E)-2-(5-bromo-1H-indol-3-yl)-3-(4-methoxypyridin-3-yl)acrylonitrile

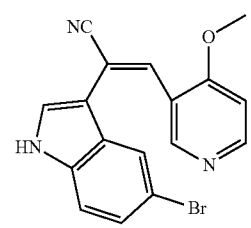 [SMILES: COc1ccncc1/C=C(/C#N)c1c[nH]c2ccc(Br)cc12]

Method E (Z)-2-(5-bromo-1H-indol-3-yl)-3-(2-methoxyphenyl)acrylonitrile (30 mg). EtOH (40 mL). Reaction time: 18 h. Aspect of the pure product: yellow solid. (Yield: 40%).

ESI-MS: (M+H)=354

¹H NMR (methanol-d4, 300 MHz) δ ppm: 8.31 (d, 1H), 8.00 (s, 1H), 7.55 (s, 1H), 7.42 (s, 1H), 7.35 (d, 1H), 7.26-7.14 (m, 2H), 6.96 (d, 1H), 4.00 (s, 3H).

Example 6

(Z)-2-(5-chloro-1H-indol-3-yl)-3-(4-(dimethyl-amino)pyridin-3-yl)acrylonitrile

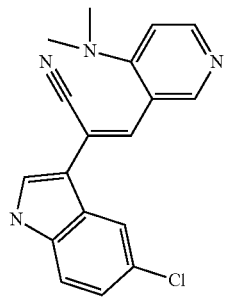

Method A tert-butyl 5-chloro-3-(cyanomethyl)-1H-indole-1-carboxylate (150 mg). Sodium hydride (28.9 mg). THF 2 mL. 4-dimethylaminonicotinaldehyde (93 mg). Trituration of the crude product with water and diisopropylether. Aspect of the product pale yellow solid (Yield: 82%).

APCI-MS: (M+H)$^+$=323

$^1$H NMR (300 MHz, DMSO-d$_6$) δ ppm: 11.92 (s, 1H), 8.52 (s, 1H), 8.26 (d, J=5.8 Hz, 1H), 7.98 (d, J=1.9 Hz, 1H), 7.90 (s, 1H), 7.59 (s, 1H), 7.51 (d, J=8.7 Hz, 1H), 7.23 (dd, J=8.7, 1.9 Hz, 1H), 6.93 (d, J=5.9 Hz, 1H), 1.16-1.10 (m, 0.33H), 1.07 (t, J=7.0 Hz, 5.6H).

Example 7

(Z)-2-(5-chloro-1H-indol-3-yl)-3-(4-(dimethyl-amino)pyridin-3-yl)acrylonitrile, hydrochloride

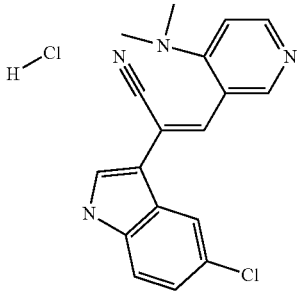 [SMILES: Cl ; CN(C)c1ccncc1/C=C(\C#N)c1c[nH]c2ccc(Cl)cc12]

In a 25 mL pear flask, (Z)-2-(5-chloro-1H-indol-3-yl)-3-(4-(dimethylamino)pyridin-3-yl)acrylonitrile (60 mg, 0.186 mmol) was dissolved in ethanol (1 mL) and dichloromethane (0.5 mL) to give a yellow solution followed by addition of HCl 37% in water (0.015 mL, 0.186 mmol).

The reaction mixture was concentrated under reduced pressure to give 67 mg of a yellow solid (Yield: 100%).

APCI-MS: (M+H)$^+$=323

$^1$H NMR (300 MHz, DMSO-d$_6$) δ ppm: 14.47-13.49 (m, 1H), 12.09 (s, 1H), 8.53 (s, 1H), 8.28 (d, J=7.3 Hz, 1H), 8.08 (s, 1H), 7.91 (s, 2H), 7.53 (d, J=8.7 Hz, 1H), 7.25 (d, J=10.6 Hz, 1H), 7.14 (d, J=7.3 Hz, 1H), 3.25 (s, 6H).

Example 8

(Z)-2-(5-bromo-1H-indol-3-yl)-3-(4-(dimethyl-amino)pyridin-3-yl)acrylonitrile

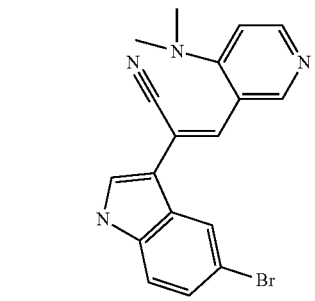 [SMILES: CN(C)c1ccncc1/C=C(\C#N)c1c[nH]c2ccc(Br)cc12]

Method A tert-butyl 5-bromo-3-(cyanomethyl)-1H-indole-1-carboxylate (150 mg). Sodium hydride (25 mg). THF 2 mL. 4-dimethylaminonicotinaldehyde (81 mg). Trituration of the crude product with water and ethanol. Aspect of the product pale yellow solid (Yield: 61%)

APCI-MS: (M+H)$^+$=367

$^1$H NMR (300 MHz, DMSO-d$_6$) δ ppm: 11.92 (s, 0.9H), 11.85-11.77 (m, 0.1H), 8.51 (s, 1H), 8.26 (d, J=5.9 Hz, 1H), 8.10 (s, 1H), 7.88 (d, J=2.8 Hz, 1H), 7.62 (s, 1H), 7.46 (d, J=8.7 Hz, 1H), 7.39-7.28 (m, 1H), 6.89 (d, J=5.9 Hz, 1H), 2.92 (s, 5.6H), 2.85 (s, 0.4H).

Example 9

(Z)-2-(5-chloro-1H-indol-3-yl)-3-(4-methoxypyri-din-3-yl)acrylonitrile

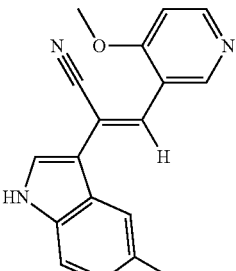

Method A tert-butyl 5-chloro-3-(cyanomethyl)-1H-indole-1-carboxylate (276 mg). THF 7 mL. Sodium hydride (57 mg), 4-methoxypyridine-3-carboxaldehyde (156 mg). Reaction time 24 hours. Trituration of the crude product with MeOH. Aspect of the pure product: orange solid. (Yield: 35%).

ESI-MS: (M+H)$^+$=310

$^1$H NMR (DMSO-d$_6$, 300 MHz) δ ppm: 11.97 (s, 1H), 8.82 (s, 1H), 8.51 (d, J=5.8 Hz, 1H), 7.94 (d, J=1.8 Hz, 1H), 7.91 (s, 1H), 7.68 (s, 1H), 7.52 (d, J=8.7 Hz, 1H), 7.24 (dd, J=8.7, 1.9 Hz, 1H), 7.19 (d, J=5.8 Hz, 1H), 3.94 (s, 3H).

Example 9b (E)-2-(5-chloro-1H-indol-3-yl)-3-(4-methoxypyridin-3-yl)acrylonitrile

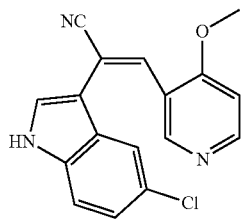 [SMILES: COc1ccncc1/C=C(/C#N)c1c[nH]c2ccc(Cl)cc12]

Method E (Z)-2-(5-chloro-1H-indol-3-yl)-3-(2-methoxyphenyl)acrylonitrile (20 mg). EtOH (35 mL). Reaction time: 8 h. Aspect of the pure product: yellow solid. (Yield: 30%).

ESI-MS: (M+H)$^+$=310

$^1$H NMR (methanol-d4, 300 MHz) δ ppm: 8.31 (d, 1H), 8.01 (s, 1H), 7.56 (s, 1H), 7.42 (s, 1H), 7.38 (d, 1H), 7.16 (d, 1H), 7.10 (d, 1H), 6.83 (d, 1H), 4.00 (s, 3H).

Example 10

(Z)-2-(5-chloro-1H-indol-3-yl)-3-(4-phenoxypyridin-3-yl)acrylonitrile

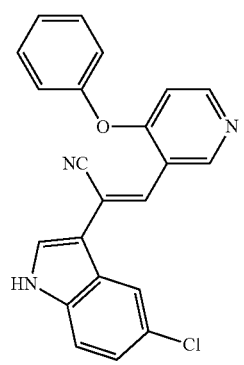 [SMILES: N#C/C(=C\c1cnccc1Oc1ccccc1)c1c[nH]c2ccc(Cl)cc12]

Method A tert-butyl 5-chloro-3-(cyanomethyl)-1H-indole-1-carboxylate (190 mg). THF 6 mL. Sodium hydride (40 mg), 4-phenoxypyridine-3-carboxaldehyde (160 mg). Reaction time 24 hours. The reaction mixture was not extracted. A precipitate was formed in the reaction mixture, filtered and washed with ether. Trituration of the precipitate with MeOH. Aspect of the pure product: yellow orange solid. (Yield: 73%).

ESI-MS: (M−H)=370

$^1$H NMR (DMSO-d$_6$, 300 MHz) δ ppm: 8.98 (s, 1H), 8.46 (d, J=5.7 Hz, 1H), 7.99 (s, 1H), 7.87 (s, 1H), 7.73 (s, 1H), 7.62 (d, 1H), 7.50 (m, 2H), 7.35-7.2 (m, 3H), 7.17 (dd, J=8.7, 1H), 6.75 (d, J=5.7 Hz, 1H).

Example 11

(Z)-2-(5-bromo-1H-indol-3-yl)-3-(4-phenoxypyridin-3-yl)acrylonitrile

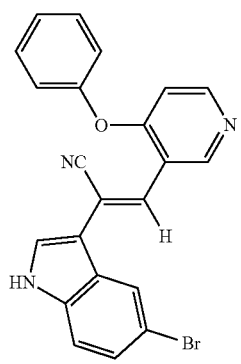 [SMILES: N#C/C(=C\c1cnccc1Oc1ccccc1)c1c[nH]c2ccc(Br)cc12]

Method A tert-butyl 5-bromo-3-(cyanomethyl)-1H-indole-1-carboxylate (224 mg). THF 4.9 mL. Sodium hydride (40 mg), 4-phenoxypyridine-3-carboxaldehyde (160 mg). Reaction time 24 hours. Trituration of the crude product with MeOH. Aspect of the pure product: yellow solid. (Yield: 18.7%).

ESI-MS: (M−H)=414

$^1$H NMR (DMSO-d$_6$, 300 MHz) δ ppm: 12.01 (s, 1H), 9.0 (s, 1H), 8.48 (d, J=5.7 Hz, 1H), 8.11 (d, J=1.7 Hz, 1H), 7.94 (s, 1H), 7.83 (s, 1H), 7.55-7.48 (m, 3H), 7.4-7.25 (m, 4H), 6.76 (d, J=5.7 Hz, 1H).

Example 12

(Z)-2-(5-methoxy-1H-indol-3-yl)-3-(4-methoxypyridin-3-yl)acrylonitrile

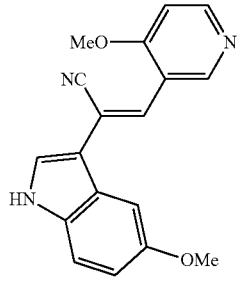

Method B (Z)-2-(5-methoxy-1H-indol-3-yl)-3-(4-chloro-3-yl)acrylonitrile (50 mg), KOH (45 mg) and MeOH (1.5 mL). Trituration with AcOEt. Aspect of the pure product: yellow solid. (Yield: 71%).

ESI-MS: (M+H)$^+$=306

$^1$H NMR (Acetone-d$_6$, 300 MHz) δ ppm: 9.02 (s, 1H), 8.50 (d, J=5.7 Hz, 1H), 7.77 (s, 1H), 7.75 (s, 1H), 7.50 (d, J=2.3 Hz, 1H), 7.46 (d, J=8.9 Hz, 1H), 7.14 (d, J=5.7 Hz, 1H), 6.93 (dd, J=8.9 Hz, J=2.3 Hz, 1H), 4.03 (s, 3H), 3.87 (s, 3H).

Example 13

(Z)-2-(5-bromo-1H-indol-3-yl)-3-(4-ethoxypyridin-3-yl)acrylonitrile

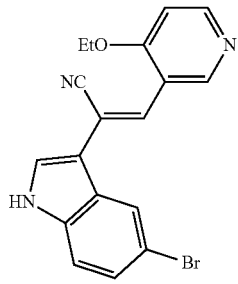 [SMILES: CCOc1ccncc1/C=C(\C#N)c1c[nH]c2ccc(Br)cc12]

Method B (Z)-2-(5-Bromo-1H-indol-3-yl)-3-(4-chloro-3-yl)acrylonitrile (40 mg), KOH (31 mg), EtOH (5 mL). Trituration with AcOEt. Aspect of the pure product: yellow solid. (Yield: 76%).

ESI-MS: (M+H)$^+$=368

$^1$H NMR (acetone-d$_6$, 300 MHz) δ ppm: 9.06 (s, 1H), 8.49 (d, J=5.5 Hz, 1H), 8.20 (s, 1H), 7.85 (s, 1H), 7.55 (d, J=8.5 Hz, 1H), 7.40 (d, J=8.2 Hz, 1H), 7.12 (d, J=5.8 Hz, 1H), 4.31 (q, J=7.0 Hz, 2H), 1.54 (t, J=7.0 Hz, 3H).

Example 14

(Z)-2-(5-bromo-1H-indol-3-yl)-3-(4-isopropoxypyridin-3-yl)acrylonitrile

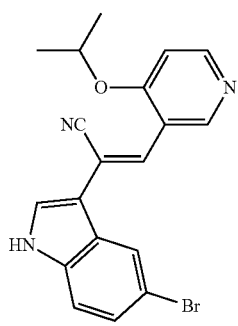 [SMILES: CC(C)Oc1ccncc1/C=C(\C#N)c1c[nH]c2ccc(Br)cc12]

Method B (Z)-2-(5-Bromo-1H-indol-3-yl)-3-(4-chloro-3-yl)acrylonitrile (70 mg), KOH (55 mg), isopropanol (2 mL). Purification by flash chromatography (CH$_2$Cl$_2$/MeOH 100/0 to 95/5). Aspect of the pure product: yellow solid. (Yield: 20%).

ESI-MS: (M+H)$^+$=382

$^1$H NMR (MeOD, 300 MHz) δ ppm: 9.02 (s, 1H), 8.42 (d, J=5.8 Hz, 1H), 8.09 (d, J=1.5 Hz, 1H), 7.75 (s, 1H), 7.69 (s, 1H), 7.42 (d, J=8.7 Hz, 1H), 7.36 (dd, J=8.7 Hz, J=1.5 Hz, 1H), 7.19 (d, J=5.8 Hz, 1H), 4.93 (sept, J=6.0 Hz, 1H), 1.50 (d, J=6.0 Hz, 6H).

Example 15

(Z)-2-(5-bromo-1H-indol-3-yl)-3-(4-(methylthio)pyridin-3-yl)acrylonitrile

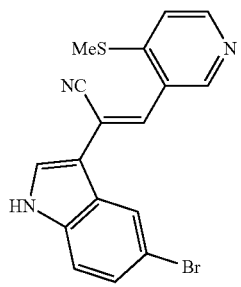 [SMILES: CSc1ccncc1/C=C(\C#N)c1c[nH]c2ccc(Br)cc12]

Method C (Z)-2-(5-Bromo-1H-indol-3-yl)-3-(4-chloro-3-yl)acrylonitrile (80 mg), NaSMe (31 mg), DMF (1 mL). Aspect of the pure product: yellow solid. (Yield: 61%).

ESI-MS: (M+H)$^+$=370

$^1$H NMR (acetone-d$_6$, 300 MHz) δ ppm: 11.12 (s, 1H), 8.83 (s, 1H), 8.48 (d, J=5.3 Hz, 1H), 8.24 (d, J=1.9 Hz, 1H), 7.91 (s, 1H), 7.67 (s, 1H), 7.57 (d, J=8.7 Hz, 1H), 7.41 (dd, J=8.7 Hz, J=1.9 Hz, 1H), 7.39 (d, J=5.3 Hz, 1H), 2.66 (s, 3H).

Example 16

(Z)-2-(5-bromo-1H-indol-3-yl)-3-(4-(ethylthio)pyridin-3-yl)acrylonitrile

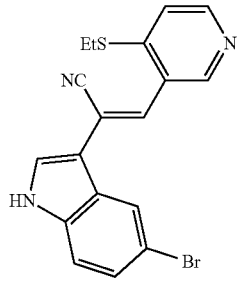

Method C (Z)-2-(5-Bromo-1H-indol-3-yl)-3-(4-chloro-3-yl)acrylonitrile (80 mg), NaSEt (37 mg), DMF (1 mL). Aspect of the pure product: yellow solid. (Yield: 70%).

ESI-MS: (M+H)$^+$=384

$^1$H NMR (acetone-d$_6$, 300 MHz) δ ppm: 11.13 (s, 1H), 8.86 (s, 1H), 8.47 (d, J=5.5 Hz, 1H), 8.26 (d, J=1.7 Hz, 1H), 7.91 (s, 1H), 7.68 (s, 1H), 7.56 (d, J=8.7 Hz, 1H), 7.45-7.39 (m, 2H), 3.21 (q, J=7.5 Hz, 2H), 1.42 (t, J=7.5 Hz, 3H).

Example 17

(Z)-2-(5-bromo-1H-indol-3-yl)-3-(4-(3-bromophenyl)pyridin-3-yl)acrylonitrile

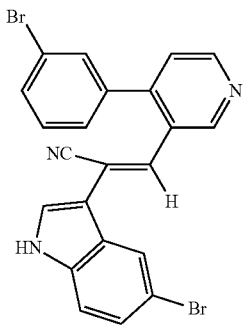 [SMILES: N#C/C(=C\c1cnccc1-c1cccc(Br)c1)c1c[nH]c2ccc(Br)cc12]

Method A tert-butyl 5-bromo-3-(cyanomethyl)-1H-indole-1-carboxylate (300 mg). THF 6.6 mL. Sodium hydride (54 mg), 4-(3-bromophenyl)-3-pyridinecarboxaldehyde (328 mg). Reaction time 24 hours. Trituration of the crude product with MeOH. Aspect of the pure product: yellow solid. (Yield: 65%).

ESI-MS: (M+H)$^+$=478

$^1$H NMR (DMSO-d$_6$, 300 MHz) δ ppm: 11.96 (s, 1H), 9.04 (s, 1H), 8.72 (d, 1H), 7.84 (s, 1H), 7.79-7.68 (m, 3H), 7.65-7.43 (m, 5H), 7.32 (dd, 1H).

Example 18

(Z)-3-(4-(3-bromophenyl)pyridin-3-yl)-2-(5-chloro-1H-indol-3-yl)acrylonitrile Method A tert-butyl 5-chloro-3-(cyanomethyl)-1H-indole-1-carboxylate (266 mg). THF 6.8 mL. Sodium hydride (55 mg), 4-(3-bromophenyl)-3-pyridinecarboxaldehyde (336 mg). Reaction time 24 hours. Trituration of the crude product with MeOH. Aspect of the pure product: yellow solid. (Yield: 52%).

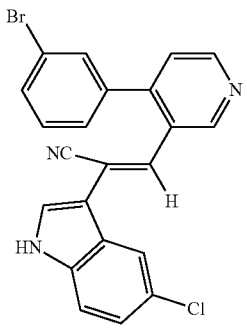 [SMILES: N#C/C(=C\c1cnccc1-c1cccc(Br)c1)c1c[nH]c2ccc(Cl)cc12]

ESI-MS: (M+H)$^+$=434

$^1$H NMR (DMSO-d$_6$, 300 MHz) δ ppm: 11.96 (s, 1H), 9.04 (s, 1H), 8.72 (d, 1H), 7.86 (s, 1H), 7.81-7.68 (m, 3H), 7.66-7.46 (m, 5H), 7.22 (dd, 1H).

Example 19

(Z)-2-(5-bromo-1H-indol-3-yl)-3-(4-(phenylthio)pyridin-3-yl)acrylonitrile

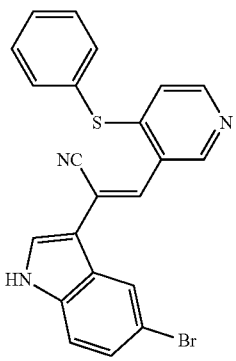 [SMILES: N#C/C(=C\c1cnccc1Sc1ccccc1)c1c[nH]c2ccc(Br)cc12]

Method D (Z)-2-(5-Bromo-1H-indol-3-yl)-3-(4-chloro-3-yl)acrylonitrile (80 mg), thiophenol (25 μl), sodium carbonate (47 mg), DMF (1 mL). Aspect of the pure product: yellow solid. (Yield: 53%).

ESI-MS: (M+H)$^+$=432

$^1$H NMR (DMSO-d$_6$, 300 MHz) δ ppm: 12.05 (s, 1H), 8.81 (s, 1H), 8.40 (d, J=5.3 Hz, 1H), 8.15 (d, J=1.7 Hz, 1H), 7.96 (s, 1H), 7.73 (s, 1H), 7.62 (m, 2H), 7.55 (m, 3H), 7.50 (d, J=8.7 Hz, 1H), 7.38 (dd, J=8.7 Hz, J=1.7 Hz, 1H), 6.81 (d, J=5.3 Hz, 1H).

Example 20

(Z)-3-(4-(benzylthio)pyridin-3-yl)-2-(5-bromo-1H-indol-3-yl)acrylonitrile

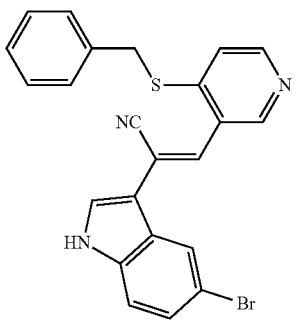 [SMILES: N#C/C(=C\c1cnccc1SCc1ccccc1)c1c[nH]c2ccc(Br)cc12]

Method D (Z)-2-(5-Bromo-1H-indol-3-yl)-3-(4-chloro-3-yl)acrylonitrile (50 mg), benzyl mercaptan (18 μL), sodium carbonate (30 mg), DMF (1 mL). Aspect of the pure product: yellow solid. (Yield: 47%).

ESI-MS: (M+H)$^+$=446

$^1$H NMR (DMSO-d$_6$, 300 MHz) δ ppm: 12.01 (s, 1H), 8.73 (s, 1H), 8.58 (d, J=5.2 Hz, 1H), 8.12 (d, J=1.2 Hz, 1H), 7.92 (s, 1H), 7.60 (s, 1H), 7.56 (d, J=5.2 Hz, 1H), 7.49-7.47 (m, 3H), 7.37-7.33 (m, 3H), 7.28 (m, 1H), 4.47 (s, 2H).

Example 21

(Z)-2-(5-bromo-1H-indol-3-yl)-3-(4-((3,4-dimethoxyphenyl)thio)pyridin-3-yl)acrylonitrile

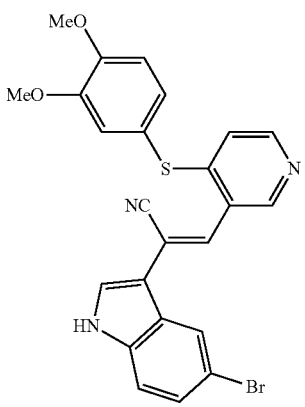 [SMILES: COc1ccc(Sc2ccncc2/C=C(\C#N)c2c[nH]c3ccc(Br)cc23)cc1OC]

Method D (Z)-2-(5-Bromo-1H-indol-3-yl)-3-(4-chloro-3-yl)acrylonitrile (61 mg), 3,4-dimethoxythiophenol (37 µL), sodium carbonate (36 mg), DMF (1 mL). Aspect of the pure product: yellow solid. (Yield: 50%).

ESI-MS: (M+H)$^+$=492

$^1$H NMR (DMSO-d$_6$, 300 MHz) δ ppm: 12.05 (s, 1H), 8.76 (s, 1H), 8.36 (d, J=5.2 Hz, 1H), 8.17 (s, 1H), 7.96 (s, 1H), 7.70 (s, 1H), 7.51 (d, J=8.5 Hz, 1H), 7.39 (d, J=8.5 Hz, 1H), 7.22 (d, J=8.2 Hz, 1H), 7.19 (s, 1H), 7.13 (d, J=8.5 Hz, 1H), 6.74 (d, J=5.2 Hz, 1H), 3.82 (s, 3H), 3.76 (s, 3H).

Example 22

(Z)-2-(5-bromo-1H-indol-3-yl)-3-(4-(4-fluorophenoxy)pyridin-3-yl)acrylonitrile

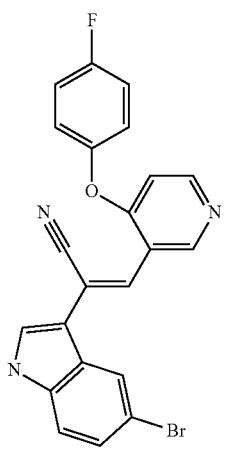 [SMILES: N#C/C(=C\c1cnccc1Oc1ccc(F)cc1)c1c[nH]c2ccc(Br)cc12]

Method A tert-butyl 5-bromo-3-(cyanomethyl)-1H-indole-1-carboxylate (200 mg), THF 2 mL. Sodium hydride (31.7 mg), 4-(4-fluorophenyl)-3-pyridinecarboxaldehyde (148 mg). Reaction time 1 h 30. Trituration of the crude product with DCM. Aspect of the product: yellow solid. (Yield: 10%).

LC-MS: (M+H)$^+$=434

$^1$H NMR (300 MHz, DMSO-d$_6$) δ ppm: 12.01 (s, 1H), 8.98 (s, 1H), 8.46 (d, J=5.7 Hz, 1H), 8.11 (d, J=1.7 Hz, 1H), 7.94 (s, 1H), 7.83 (s, 1H), 7.48 (d, J=8.7 Hz, 1H), 7.38-7.31 (m, 5H), 6.73 (d, J=5.7 Hz, 1H).

Example 23

(Z)-2-(5-chloro-1H-indol-3-yl)-3-(4-(4-fluorophenoxy)pyridin-3-yl)acrylonitrile

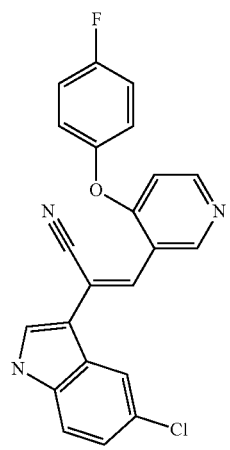 [SMILES: N#C/C(=C\c1cnccc1Oc1ccc(F)cc1)c1c[nH]c2ccc(Cl)cc12]

Method A tert-butyl 5-chloro-3-(cyanomethyl)-1H-indole-1-carboxylate (200 mg). THF 2 mL. Sodium hydride (35.1 mg), 4-(4-fluorophenyl)-3-pyridinecarboxaldehyde (163 mg). Reaction time 1 hour 30 minutes. Trituration of the crude product with DCM. Aspect of the product: yellow solid. (Yield: 82%).

APCI-MS: (M+H)$^+$=390

$^1$H NMR (300 MHz, DMSO-d$_6$) δ ppm: 8.98 (s, 1H), 8.46 (d, J=5.7 Hz, 1H), 7.99-7.92 (m, 2H), 7.83 (s, 1H), 7.52 (d, J=8.7 Hz, 1H), 7.34 (d, J=5.9 Hz, 4H), 7.24 (dd, J=8.7, 1.8 Hz, 1H), 6.73 (d, J=5.7 Hz, 1H).

Example 24

(Z)-2-(5-bromo-1H-indol-3-yl)-3-(4-(diethylamino)pyridin-3-yl)acrylonitrile

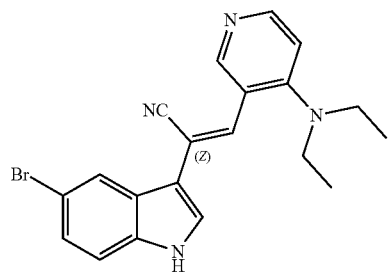 [SMILES: CCN(CC)c1ccncc1/C=C(\C#N)c1c[nH]c2ccc(Br)cc12]

Method A

Aspect of the product: yellow solid (Yield: 60%)
APCI-MS: (M+H)⁺=395
¹H NMR (300 MHz, DMSO-d$_6$) δ ppm: 11.93 (s, 0.83H), 11.88-11.76 (m, 0.12H), 8.52 (s, 1H), 8.27 (d, J=5.8 Hz, 1H), 8.12 (d, J=1.7 Hz, 1H), 7.88 (s, 1H), 7.59 (s, 1H), 7.51-7.21 (m, 2H), 6.93 (d, J=5.9 Hz, 1H), 3.32-3.24 (m, 4H), 1.07 (t, J=7.0 Hz, 6H).

Example 25

(Z)-2-(5-bromo-1H-indol-3-yl)-3-(4-(4-(trifluoromethyl)phenyl)pyridin-3-yl)acrylonitrile

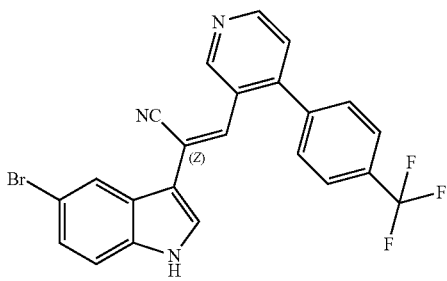

Method A tert-butyl 5-bromo-3-(cyanomethyl)-1H-indole-1-carboxylate (120 mg). THF 3 mL. Sodium hydride (20.05 mg), 4-(4-trifluoromethylphenyl)-3-pyridinecarboxaldehyde (108 mg). Reaction time 16 hours. Purification by chromatography on 24 g Redisep column 20-40 µm, eluted with a gradient of CH$_2$Cl$_2$/MeOH from 100/00 to 95/05. Dissolution of the solid in EtOH (3 mL) and water (0.3 mL) and concentration in a Genevac evaporator to remove the traces of solvent. Aspect of the product: yellow solid. (Yield: 57%).
APCI-MS: (M+H)⁺=468
¹H NMR (300 MHz, DMSO-d$_6$) δ ppm: 12.19-11.57 (s, 1H), 9.11 (s, 1H), 8.80-8.61 (d, 1H), 7.66 (m, 11H).

Example 26

(Z)-2-(5-chloro-1H-indol-3-yl)-3-(4-(4-(trifluoromethyl)phenyl)pyridin-3-yl)acrylonitrile

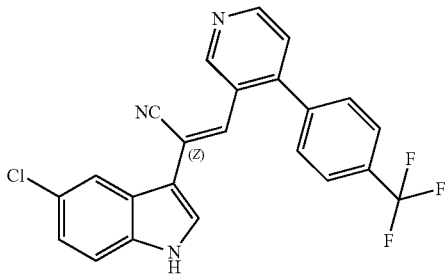 [SMILES: N#C/C(=C\c1cnccc1-c1ccc(C(F)(F)F)cc1)c1c[nH]c2ccc(Cl)cc12]

Method A tert-butyl 5-chloro-3-(cyanomethyl)-1H-indole-1-carboxylate (120 mg). THF 3 mL. Sodium hydride (23.11 mg), 4-(4-trifluoromethylphenyl)-3-pyridinecarboxaldehyde (124 mg). Reaction time 16 hours. Purification by chromatography on 24 g Redisep column 20-40 µm, eluted with a gradient of CH$_2$Cl$_2$/MeOH from 100/00 to 95/05. Dissolution of the solid in EtOH (3 mL) and water (0.3 mL) and concentration in a Genevac evaporator to remove the traces of solvent. Aspect of the product: yellow solid. (Yield: 68%).
APCI-MS: (M+H)⁺=424
¹H NMR (300 MHz, DMSO-d$_6$) δ ppm: 12.40-11.44 (m, 1H), 9.10 (s, 1H), 8.73 (d, J=5.1 Hz, 1H), 7.91-7.16 (m, 11H).

Example 27

(Z)-2-(5-chloro-1H-indol-3-yl)-3-(4-((4-fluorophenyl)thio)pyridin-3-yl)acrylonitrile

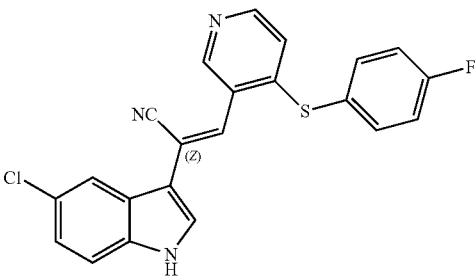

Method A tert-butyl 5-chloro-3-(cyanomethyl)-1H-indole-1-carboxylate (150 mg). THF 2 mL. Sodium hydride (28.9 mg), 4-(4-fluorophenylthio)-3-pyridinecarboxaldehyde (144 mg). Reaction time 16 hours. Trituration of the crude product with heptane and diisopropylether. Aspect of the product: yellow solid. (Yield: 42%).
APCI-MS: (M+H)⁺=406
¹H NMR (300 MHz, DMSO-d$_6$) δ ppm: 8.79 (s, 1H), 8.38 (d, J=5.4 Hz, 1H), 7.97 (s, 2H), 7.68 (s, 4H), 7.56 (d, J=8.6 Hz, 1H), 7.42 (d, J=8.6 Hz, 3H), 7.26 (s, 1H), 6.76 (d, J=5.4 Hz, 1H).

Example 28

(Z)-2-(5-bromo-1H-indol-3-yl)-3-(4-((4-fluorophenyl)thio)pyridin-3-yl)acrylonitrile

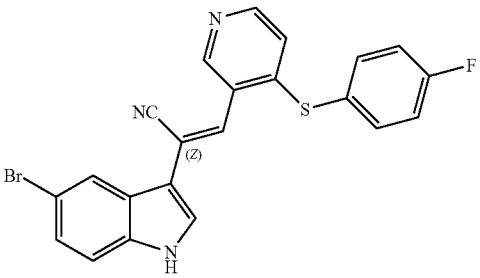 [SMILES: N#C/C(=C\c1cnccc1Sc1ccc(F)cc1)c1c[nH]c2ccc(Cl)cc12]

Method A tert-butyl 5-bromo-3-(cyanomethyl)-1H-indole-1-carboxylate (150 mg). THF 2 mL. Sodium hydride (25.06 mg), 4-(4-fluorophenylthio)-3-pyridinecarboxaldehyde (125 mg). Reaction time 16 hours. Trituration of the crude product with heptane and ether.

Aspect of the product: yellow solid. (Yield: 32%).
APCI-MS: (M+H)$^+$=450
$^1$H NMR (300 MHz, DMSO-d$_6$) δ ppm: 11.98 (sl, 1H), 8.82-8.74 (m, 1H), 8.43-8.35 (m, 1H), 8.18-8.13 (m, 1H), 7.99-7.93 (m, 1H), 7.70 (dd, J=8.6, 2.7 Hz, 3H), 7.44 (qd, J=8.6, 7.1 Hz, 4H), 6.80-6.73 (m, 1H).

Example 29

(Z)-2-(5-chloro-1H-indol-3-yl)-3-(4-(furan-3-yl)pyridin-3-yl)acrylonitrile

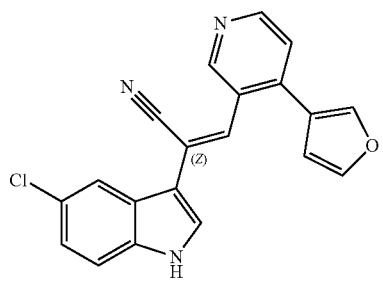 [SMILES: N#C/C(=C\c1cnccc1-c1ccoc1)c1c[nH]c2ccc(Cl)cc12]

Method A tert-butyl 5-chloro-3-(cyanomethyl)-1H-indole-1-carboxylate (150 mg). THF 3 mL. Sodium hydride (17.33 mg), 4-(furan-3-yl)nicotinaldehyde 107 mg). Reaction time 16 hours. Trituration of the crude product with heptane and diisopropylether. Aspect of the product: yellow solid. (Yield: 21%).

APCI-MS: (M+H)$^+$=346
$^1$H NMR (300 MHz, DMSO-d$_6$) δ ppm: 11.99 (s, 1H), 8.93 (s, 1H), 8.64 (d, J=5.2 Hz, 1H), 8.10 (s, 1H), 8.01-7.92 (m, 2H), 7.87 (s, 1H), 7.77 (s, 1H), 7.64 (d, J=5.1 Hz, 1H), 7.53 (d, J=8.7 Hz, 1H), 7.25 (dd, J=8.7, 1.9 Hz, 1H), 6.97 (s, 1H).

Example 30

(Z)-2-(5-chloro-1H-indol-3-yl)-3-(4-(pyridin-2-ylthio)pyridin-3-yl)acrylonitrile

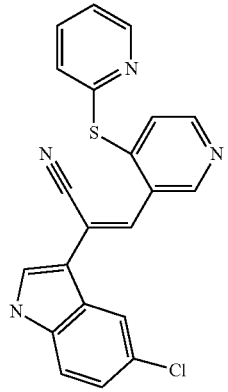 [SMILES: N#C/C(=C\c1cnccc1Sc1ccccn1)c1c[nH]c2ccc(Cl)cc12]

Method A tert-butyl 5-chloro-3-(cyanomethyl)-1H-indole-1-carboxylate (150 mg). THF 2 mL. Sodium hydride (28.9 mg), 4-(piridin-2-yl)thio-nicotinaldehyde (134 mg). Reaction time 16 hours. Trituration of the crude product with heptane and diisopropylether.

Aspect of the product: yellow solid. (Yield: 55%).
APCI-MS: (M+H)$^+$=389
$^1$H NMR (300 MHz, DMSO-d$_6$) δ ppm: 9.00 (s, 1H), 8.60-8.52 (m, 1H), 8.48 (d, J=3.8 Hz, 1H), 7.86 (s, 1H), 7.81-7.73 (m, 1H), 7.68 (s, 1H), 7.59 (s, 1H), 7.52 (d, J=5.3 Hz, 2H), 7.43 (d, J=7.9 Hz, 1H), 7.28 (dd, J=7.0, 5.2 Hz, 1H), 7.20-7.12 (m, 1H).

Example 31

(Z)-2-(5-bromo-1H-indol-3-yl)-3-(4-(pyridin-2-ylthio)pyridin-3-yl)acrylonitrile

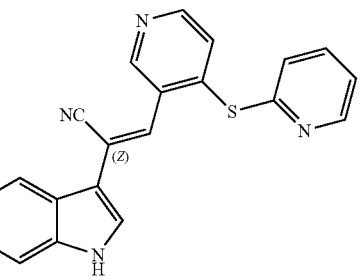

Method A tert-butyl 5-bromo-3-(cyanomethyl)-1H-indole-1-carboxylate (150 mg). THF 2 mL. Sodium hydride (25.06 mg), 4-(piridin-2-yl)thio-nicotinaldehyde (116 mg). Reaction time 16 hours. Trituration of the crude product with heptane and ether. Aspect of the product: yellow solid. (Yield: 65%).

APCI-MS: (M+H)$^+$=433
$^1$H NMR (300 MHz, DMSO-d$_6$) δ ppm: 9.00 (s, 1H), 8.62-8.57 (m, 1H), 8.52-8.46 (m, 1H), 7.91-7.86 (m, 2H), 7.78 (ddd, J=9.5, 7.7, 1.8 Hz, 1H), 7.68 (s, 1H), 7.56-7.52 (m, 1H), 7.49-7.42 (m, 2H), 7.37-7.26 (m, 2H).

Example 32

(Z)-3-(4-(1H-1,2,4-triazol-1-yl)pyridin-3-yl)-2-(5-bromo-1H-indol-3-yl)acrylonitrile

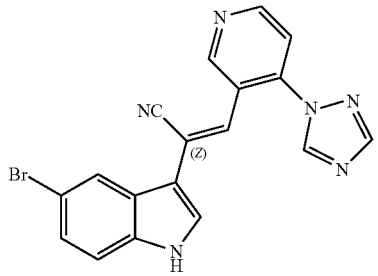 [SMILES: N#C/C(=C\c1cnccc1-n1cncn1)c1c[nH]c2ccc(Cl)cc12]

Method A tert-butyl 5-bromo-3-(cyanomethyl)-1H-indole-1-carboxylate (150 mg). THF 2 mL. Sodium hydride (25.06 mg), 4-(1H-1,2,4-triazol-1-yl)nicotinaldehyde (118 mg). Reaction time 16 hours. Trituration of the crude product with ethanol. Aspect of the product: yellow solid. (Yield: 32%).
APCI-MS: (M+H)$^+$=391
$^1$H NMR (300 MHz, DMSO-d$_6$) δ ppm: 12.00 (s, 1H), 9.28 (s, 1H), 9.14 (s, 1H), 8.81 (d, 1H), 8.37 (s, 1H), 8.10 (s, 1H), 7.87 (s, 3H), 7.52-7.29 (m, 2H).

Example 33

(Z)-3-(4-(1H-1,2,4-triazol-1-yl)pyridin-3-yl)-2-(5-chloro-1H-indol-3-yl)acrylonitrile

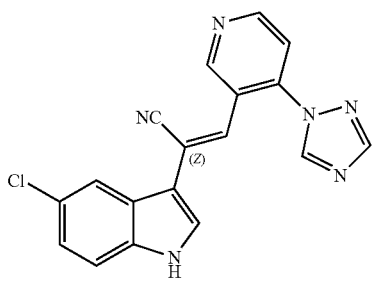

Method A tert-butyl 5-chloro-3-(cyanomethyl)-1H-indole-1-carboxylate (150 mg). THF 5 mL. Sodium hydride (28.9 mg), 4-(1H-1,2,4-triazol-1-yl)nicotinaldehyde (136 mg). Reaction time 16 hours. Purification by flash chromatography on 24 g Redisep column 20-40 m, gradient 100% CH$_2$Cl$_2$ to CH$_2$Cl$_2$/MeOH (90/10). Aspect of the product: yellow solid. (Yield: 33%).
Aspect of the product: yellow solid (Yield: 33%)
APCI-MS: (M+H)$^+$=347
$^1$H NMR (300 MHz, DMSO-d$_6$) δ ppm: 12.32-11.49 (m, 1H), 9.27 (s, 1H), 9.15 (d, J=4.0 Hz, 1H), 8.82 (d, J=5.4 Hz, 1H), 8.66-8.57 (m, 0.1H), 8.46-8.25 (m, 1H), 8.03-7.71 (m, 4H), 7.59-7.35 (m, 1H), 7.25 (dd, J=8.7, 2.0 Hz, 1H).

Example 34

(Z)-2-(5-bromo-1H-indol-3-yl)-3-(4-(furan-3-yl)pyridin-3-yl)acrylonitrile

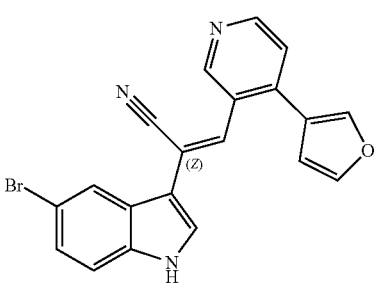

Method A tert-butyl 5-bromo-3-(cyanomethyl)-1H-indole-1-carboxylate (150 mg). THF 3 mL. Sodium hydride (15.03 mg), 4-(furan-3-yl)nicotinaldehyde (93 mg). Reaction time 16 hours. Trituration of the crude product with water and NaOH. Aspect of the product: yellow solid. (Yield: 27%).
APCI-MS: (M+H)$^+$=390
$^1$H NMR (300 MHz, DMSO-d$_6$) δ ppm: 11.98 (s, 1H), 8.92 (s, 1H), 8.64 (d, J=5.2 Hz, 1H), 8.13-8.06 (m, 2H), 7.92 (d, J=2.7 Hz, 1H), 7.87 (t, J=1.7 Hz, 1H), 7.76 (s, 1H), 7.63 (d, J=5.1 Hz, 1H), 7.48 (d, J=8.7 Hz, 1H), 7.35 (dd, J=8.7, 1.8 Hz, 1H), 6.96 (d, J=1.0 Hz, 1H).

Example 34b (E)-2-(5-bromo-1H-indol-3-yl)-3-(4-(furan-3-yl)pyridin-3-yl)acrylonitrile

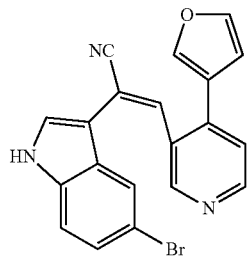 [SMILES: N#C/C(=C/c1cnccc1-c1ccoc1)c1c[nH]c2ccc(Br)cc12]

Method E (Z)-2-(5-bromo-1H-indol-3-yl)-3-(4-(furan-3-yl)pyridin-3-yl)acrylonitrile (20 mg). EtOH (40 mL). Reaction time: 8 h. Aspect of the pure product: yellow solid. (Yield: 60%).
ESI-MS: (M+H)$^+$=390
$^1$H NMR (methanol-d4, 300 MHz) δ ppm: 8.37 (d, 1H), 8.19 (s, 1H), 8.0 (s, 1H), 7.72 (s, 1H), 7.60 (d, 1H), 7.45 (s, 1H), 7.38 (s, 1H), 7.30 (d, 1H), 7.19 (d, 1H), 6.98 (s, 1H), 6.89 (s, 1H).

Example 35

(Z)-2-(5-chloro-1H-indol-3-yl)-3-(4-methoxypyridin-3-yl)acrylonitrile, hydrochloride

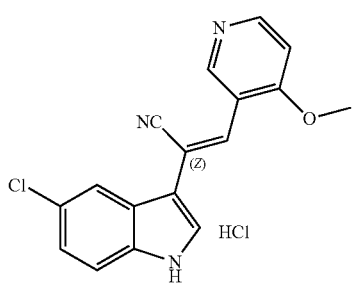 [SMILES: COc1ccncc1/C=C(\C#N)c1c[nH]c2ccc(Cl)cc12 ; Cl]

Method A tert-butyl 5-chloro-3-(cyanomethyl)-1H-indole-1-carboxylate (300 mg). THF 5 mL. Sodium hydride (57.8 mg), 4-methoxynicotinaldehyde (170 mg). Reaction time 16 hours. Trituration of the crude product with DCM and 4N HCl in dioxane. Aspect of the product: yellow solid. (Yield: 81%).

APCI-MS: (M+H)⁺=310

$^1$H NMR (300 MHz, DMSO-d$_6$) δ ppm: 12.18 (s, 1H), 9.12 (s, 1H), 8.86 (d, J=6.8 Hz, 1H), 7.99 (d, J=3.1 Hz, 2H), 7.71 (d, J=6.8 Hz, 1H), 7.64 (s, 1H), 7.55 (d, J=8.7 Hz, 1H), 7.27 (dd, J=8.7, 1.9 Hz, 1H), 4.16 (s, 3H).

Example 36

(Z)-2-(5-bromo-1H-indol-3-yl)-3-(4-((2-dimethylamino)ethyl)thio)pyridin-3-yl)acrylonitrile

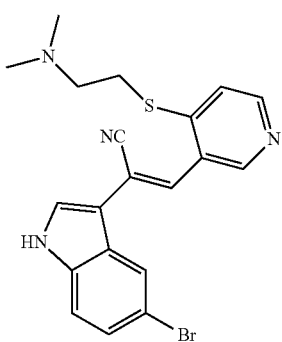 [SMILES: CN(C)CCSc1ccncc1/C=C(\C#N)c1c[nH]c2ccc(Br)cc12]

Method D (Z)-2-(5-bromo-1H-indol-3-yl)-3-(4-chloropyridin-3-yl) acrylonitrile (50 mg). DMF 2.0 mL. Potassium carbonate (64 mg), 2-(dimethyl)aminoethanethiol hydrochloride (25 mg). Reaction time 12 hours at 60° C. Trituration of the crude product with AcOEt. Aspect of the pure product: yellow solid. (Yield: 50%).

ESI-MS: (M+H)⁺=428

$^1$H NMR (acetone-d$_6$, 300 MHz) δ ppm: 11.14 (s, 1H), 8.86 (s, 1H), 8.48 (s, 1H), 8.28 (d, 1H), 7.92 (s, 1H), 7.74 (s, 1H) 7.57 (d, 1H), 7.48 (d, 1H), 7.44 (dd, 1H), 3.33 (t, 2H), 2.70 (t, 2H), 2.28 (s, 6H).

Example 37

(Z)-3-(2-(5-bromo-1H-indol-3-yl)-2-cyanovinyl)-4-(4-fluorophenoxy)benzonitrile

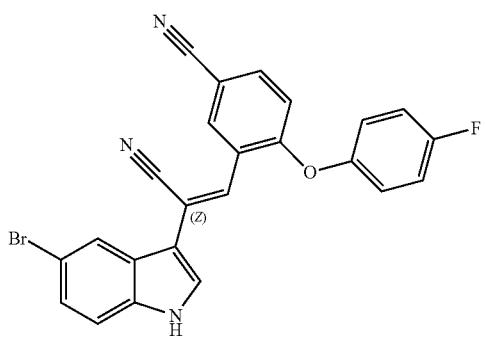 [SMILES: N#C/C(=C\c1cc(C#N)ccc1Oc1ccc(F)cc1)c1c[nH]c2ccc(Br)cc12]

Method A tert-butyl 5-bromo-3-(cyanomethyl)-1H-indole-1-carboxylate (100 mg). THF 2.0 mL. Sodium hydride (16.71 mg), 3-cyano-4-fluorophenoxy-benzaldehyde (102 mg). Reaction time 1 hour 30 minutes. Purification by flash chromatography, eluent petroleum ether/MTBE. Aspect of the pure product: yellow solid. (Yield: 48%).

APCI-MS: (M−H)=456

$^1$H NMR (300 MHz, DMSO-d$_6$) δ ppm: 12.02 (s, 1H), 8.39 (s, 1H), 8.05 (s, 1H), 7.93 (s, 1H), 7.86 (d, J=6.6 Hz, 1H), 7.81 (s, 1H), 7.47 (d, J=8.7 Hz, 1H), 7.32 (dd, J=15.3, 7.0 Hz, 5H), 6.95 (d, J=8.7 Hz, 1H).

Example 38

(Z)-3-(2-(5-bromo-1H-indol-3-yl)-2-cyanovinyl)-4-methoxybenzonitrile

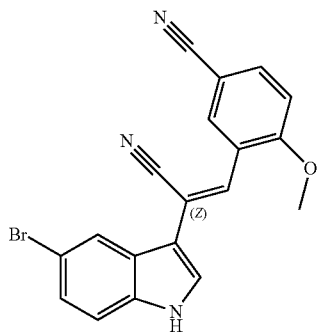 [SMILES: COc1ccc(C#N)cc1/C=C(\C#N)c1c[nH]c2ccc(Br)cc12]

Method A

Tert-butyl 5-bromo-3-(cyanomethyl)-1H-indole-1-carboxylate (150 mg, 0.447 mmol) THF 2 mL, NaH (25.06 mg, 0.626 mmol), 3-formyl-4-methoxybenzonitrile (88 mg, 0.537 mmol). Reaction time 1 hour 30 minutes. The reaction mixture diluted with water (20 mL). The resulting solid was filtered, washed successively with water, CH$_2$Cl$_2$, DIPE and acetonitrile and dried in vacuo to give 55 mg of a yellow solid (Yield: 30%).

APCI-MS: (M−H)=376

$^1$H NMR (300 MHz, DMSO-d$_6$) δ ppm: 11.99 (s, 1H), 8.22 (s, 1H), 8.08 (s, 1H), 7.91 (s, 2H), 7.70 (s, 1H), 7.60-7.15 (m, 3H), 3.97 (s, 3H).

Example 38b (E)-3-(2-(5-bromo-1H-indol-3-yl)-2-cyanovinyl)-4-methoxybenzonitrile

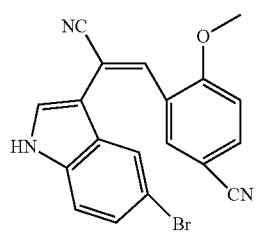 [SMILES: COc1ccc(C#N)cc1/C=C(/C#N)c1c[nH]c2ccc(Br)cc12]

Method E (Z)-3-(2-(5-bromo-1H-indol-3-yl)-2-cyanovinyl)-4-methoxybenzonitrile (20 mg). EtOH (40 mL). Reaction time: 8 h. Aspect of the pure product: yellow solid. (Yield: 60%).

ESI-MS: (M+H)$^+$=379

$^1$H NMR (methanol-d4, 300 MHz) δ ppm: 7.61 (d, 1H), 7.49 (s, 1H), 7.36 (s, 1H), 7.32 (d, 1H), 7.26-7.13 (m, 3H), 6.85 (d, 1H), 3.91 (s, 3H).

Example 39

(Z)-3-(2-(5-bromo-1H-indol-3-yl)-2-cyanovinyl)-4-(dimethylamino)benzonitrile

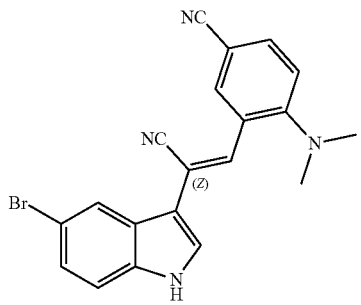 [SMILES: CN(C)c1ccc(C#N)cc1/C=C(\C#N)c1c[nH]c2ccc(Br)cc12]

Method A tert-butyl 5-bromo-3-(cyanomethyl)-1H-indole-1-carboxylate (120 mg). THF 2.5 mL. Sodium hydride (11.55 mg), 3-cyano-4-dimethylamino-benzaldehyde (73.3 mg). Reaction time 16 hours. Silical gel flash-column chromatography (eluent heptane/ethyl acetate. Aspect of the purified product: yellow solid. (Yield: 33%).

APCI-MS: (M+H)$^+$=391

$^1$H NMR (300 MHz, DMSO-d$_6$) δ ppm: 11.98 (s, 1H), 8.10 (d, J=1.6 Hz, 1H), 8.05 (d, J=1.7 Hz, 1H), 7.91 (s, 1H), 7.75 (dd, J=8.6, 2.1 Hz, 1H), 7.56 (s, 1H), 7.48 (d, J=8.7 Hz, 1H), 7.35 (dd, J=8.7, 1.8 Hz, 1H), 7.16 (d, J=8.7 Hz, 1H), 2.89 (s, 6H).

Example 40

(Z)-3-(2-(5-chloro-1H-indol-3-yl)-2-cyanovinyl)-4-methoxybenzonitrile

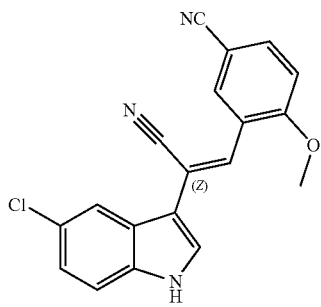 [SMILES: COc1ccc(C#N)cc1/C=C(\C#N)c1c[nH]c2ccc(Cl)cc12]

Method A tert-butyl 5-chloro-3-(cyanomethyl)-1H-indole-1-carboxylate (200 mg). THF 2.0 mL. Sodium hydride (35.1 mg), 3-cyano-4-methoxybenzaldehyde (124 mg). Reaction time 1 hour 30 minutes. Silical gel flash-column chromatography (petroleum ether/DIPE) and trituration of the purified product with acetonitrile. Aspect of the pure product: yellow solid. (Yield: 40%).

APCI-MS: (M−H)=332

$^1$H NMR (300 MHz, DMSO-d$_6$) δ ppm: 8.21 (s, 1H), 7.93 (d, J=6.5 Hz, 3H), 7.70 (s, 1H), 7.52 (d, J=8.7 Hz, 1H), 7.29 (dd, J=22.2, 9.6 Hz, 2H), 3.96 (s, 3H).

Example 41

(Z)-3-(2-(5-chloro-1H-indol-3-yl)-2-cyanovinyl)-4-(dimethylamino)benzonitrile

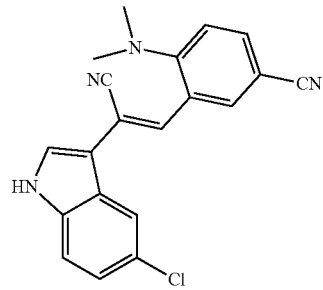 [SMILES: CN(C)c1ccc(C#N)cc1/C=C(\C#N)c1c[nH]c2ccc(Cl)cc12]

Method A tert-butyl 5-chloro-3-(cyanomethyl)-1H-indole-1-carboxylate (200 mg). THF 2.0 mL. Sodium hydride (35.1 mg), 3-cyano-4-dimethylaminobenzaldehyde (134 mg). Reaction time 1 hour 30 minutes. Silical gel flash-column chromatography (petroleum ether/DIPE) and trituration of the purified product with acetonitrile. Aspect of the pure product: yellow solid. (Yield: 33%).

APCI-MS: (M+H)$^+$=347

$^1$H NMR (300 MHz, DMSO-d$_6$) δ ppm: 11.95 (s, 1H), 8.04 (d, J=1.7 Hz, 1H), 8.00-7.89 (m, 2H), 7.75 (dd, J=8.6, 2.0 Hz, 1H), 7.62-7.45 (m, 2H), 7.30-7.09 (m, 2H), 2.89 (s, 6H).

Example 42

(Z)-3-(2-(5-chloro-1H-indol-3-yl)-2-cyanovinyl)-4-(ethylthio)benzonitrile

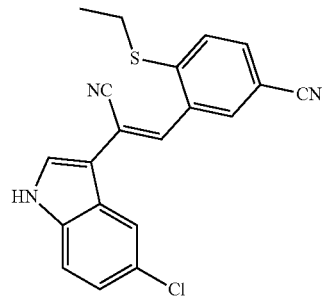 [SMILES: CCSc1ccc(C#N)cc1/C=C(\C#N)c1c[nH]c2ccc(Cl)cc12]

Method A tert-butyl 5-chloro-3-(cyanomethyl)-1H-indole-1-carboxylate (200 mg). THF 2.0 mL. Sodium hydride (35.1 mg), 3-cyano-4-ethylthiobenzaldehyde (145 mg). Reaction time 1 hour 30 minutes. Silical gel flash-column chromatography (petroleum ether/DIPE) and trituration of the purified product with acetonitrile. Aspect of the pure product: yellow solid. (Yield: 36%).

APCI-MS: (M−H)=362

$^1$H NMR (300 MHz, DMSO-d$_6$) δ ppm: 12.04 (s, 1H), 8.12 (s, 1H), 8.04-7.92 (m, 2H), 7.87 (dd, J=8.3, 1.7 Hz, 1H), 7.72-7.58 (m, 2H), 7.54 (d, J=8.7 Hz, 1H), 7.27 (dd, J=8.7, 1.9 Hz, 1H), 3.18 (q, J=7.3 Hz, 2H), 1.31 (t, J=7.3 Hz, 3H).

Example 43

(Z)—N-(3-(2-(5-bromo-1H-indol-3-yl)-2-cyanovinyl)pyridin-4-yl)pivalamide

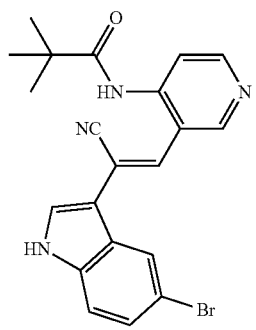 [SMILES: CC(C)(C)C(=O)Nc1ccncc1/C=C(\C#N)c1c[nH]c2ccc(Br)cc12]

Method A tert-butyl 5-bromo-3-(cyanomethyl)-1H-indole-1-carboxylate (300 mg). THE 6 mL. Sodium hydride (54 mg), N-(formyl-pyridin-4-yl)-2,2-dimethyl-propionamide (258 mg). Reaction time 24 hours. Silical gel flash-column chromatography (elution with cycloheptane/AcOEt: 1/1 to 1/9) and trituration with methanol. Aspect of the pure product: yellow solid. (Yield: 13%).

ESI-MS: (M−H)=421

$^1$H NMR (DMSO-d$_6$, 300 MHz) δ ppm: 11.98 (s, 1H), 9.49 (s, 1H), 8.96 (s, 1H), 8.55 (s, 1H), 8.17 (d, 1H), 7.88 (d, 1H), 7.68 (s, 1H), 7.56 (d, 1H), 7.50 (d, 1H), 1.25 (s, 9H).

Example 44

(Z)—N-(3-(2-(5-chloro-1H-indol-3-yl)-2-cyanovinyl)pyridin-4-yl)pivalamide

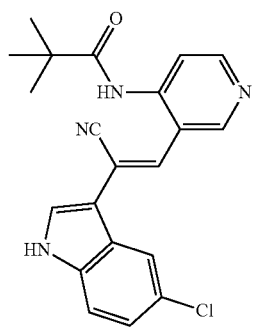 [SMILES: CC(C)(C)C(=O)Nc1ccncc1/C=C(\C#N)c1c[nH]c2ccc(Cl)cc12]

Method A tert-butyl 5-chloro-3-(cyanomethyl)-1H-indole-1-carboxylate (300 mg). THF 6 mL. Sodium hydride (62 mg), N-(formyl-pyridin-4-yl)-2,2-dimethyl-propionamide (298 mg). Reaction time 24 hours. Silical gel flash-column chromatography (elution with cycloheptane/AcOEt: 1/1 to 1/9) of the residue afforded the corresponding acrylonitrile as a yellow solid (Yield: 18%).

ESI-MS: (M+H)$^+$=379

$^1$H NMR (DMSO-d$_6$, 300 MHz) δ ppm: 11.98 (s, 1H), 9.49 (sl, 1H), 8.96 (s, 1H), 8.55 (s, 1H), 8.17 (s, 1H), 7.85 (s, 1H), 7.68 (s, 1H), 7.56 (m, 1H), 7.25 (d, 1H), 1.22 (s, 9H).

Example 45

(Z)-2-(6-bromo-1H-indol-3-yl)-3-(4-methoxypyridin-3-yl)acrylonitrile

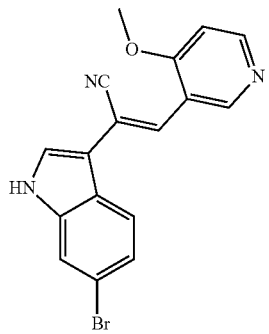 [SMILES: COc1ccncc1/C=C(\C#N)c1c[nH]c2cc(Br)ccc12]

Method F

Tert-butyl 6-bromo-3-(cyanomethyl)-1H-indole-1-carboxylate (84.0 mg), NaH (10.0 mg). THF (2 mL). 10 min at rt. 4-methoxynicotinaldehyde (41.0 mg). 12 h at rt.

Trituration of the crude in AcOEt. Aspect of the pure product: yellow solid. (Yield: 35%).

ESI-MS: (M+H)$^+$=356

$^1$H NMR (methanol-d4, 300 MHz) δ ppm: 8.95 (s, 1H), 8.47 (d, 1H), 7.87 (d, 1H), 7.76 (s, 1H), 7.70-7.65 (m, 2H), 7.33 (d, 1H), 7.21 (d, 1H), 4.06 (s, 3H).

Example 46

(Z)-2-(6-fluoro-1H-indol-3-yl)-3-(4-methoxypyridin-3-yl)acrylonitrile

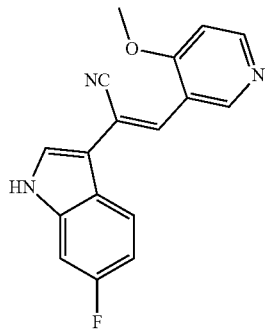 [SMILES: COc1ccncc1/C=C(\C#N)c1c[nH]c2cc(F)ccc12]

Method F

Tert-butyl 6-fluoro-3-(cyanomethyl)-1H-indole-1-carboxylate (98.0 mg), NaH (18.0 mg). THF (3 mL). 10 min at rt. 4-methoxynicotinaldehyde (58.0 mg). 12 h at rt.

Trituration of the crude in AcOEt. Aspect of the pure product: yellow solid. (Yield: 43%).

ESI-MS: (M+H)+=294

$^1$H NMR (methanol-d4, 300 MHz) δ ppm: 8.30 (d, 1H), 8.00 (s, 1H), 7.55 (s, 1H), 7.41 (s, 1H), 7.38 (d, 1H), 7.16 (d, 1H), 7.10 (dd, 1H), 6.82 (d, 1H), 4.00 (s, 3H).

Example 47

(Z)-2-(6-chloro-1H-indol-3-yl)-3-(4-methoxypyridin-3-yl)acrylonitrile

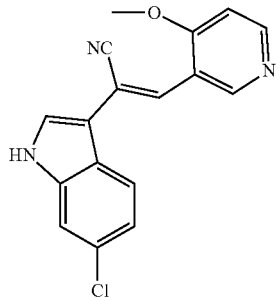 [SMILES: COc1ccncc1/C=C(\C#N)c1c[nH]c2cc(Cl)ccc12]

Method F

Tert-butyl 6-chloro-3-(cyanomethyl)-1H-indole-1-carboxylate (100.0 mg), NaH (18.0 mg). THF (3 mL). 10 min at rt. 4-methoxynicotinaldehyde (56.0 mg). 12 h at rt. NaOH 2.5 M (1.5 mL). 12 h at rt. Trituration of the crude in AcOEt. Aspect of the pure product: yellow solid. (Yield: 42%).

ESI-MS: (M+H)+=310

$^1$H NMR (methanol-d4, 300 MHz) δ ppm: 8.95 (s, 1H), 8.48 (d, 1H), 7.92 (d, 1H), 7.76 (s, 1H), 7.71 (s, 1H), 7.50 (d, 1H), 7.24-7.18 (m, 2H), 4.06 (s, 3H).

Example 48

(Z)-3-(2-(5-bromo-1H-indol-3-yl)-2-cyanovinyl)-4-(furan-3-yl)pyridine-1-oxide

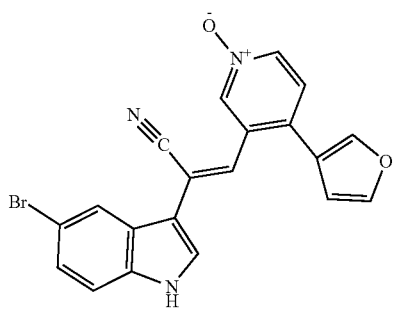 [SMILES: N#C/C(=C\c1c[n+](O)ccc1-c1ccoc1)c1c[nH]c2ccc(Br)cc12]

Method G (Z)-2-(5-bromo-1H-indol-3-yl)-3-(4-(furan-3-yl)pyridin-3-yl)acrylonitrile (30.0 mg), m-CPBA (28.0+15.0 mg). THF (1.0 mL). 16 h at room temperature. Trituration of the crude in AcOEt. Aspect of the pure product: yellow solid. (Yield: 72%).

ESI-MS: (M+H)+=408

$^1$H NMR (methanol-d4, 300 MHz) δ ppm: 8.83 (s, 1H), 8.37 (d, 1H), 8.03 (s, 1H), 8.01-7.92 (m, 2H), 7.82 (s, 1H), 7.79-7.72 (m, 1H), 7.66-7.56 (m, 2H), 7.54-7.33 (m, 1H), 6.86 (s, 1H).

Example 49

(Z)-3-(2-(5-chloro-1H-indol-3-yl)-2-cyanovinyl)-4-methoxypyridine 1-oxide

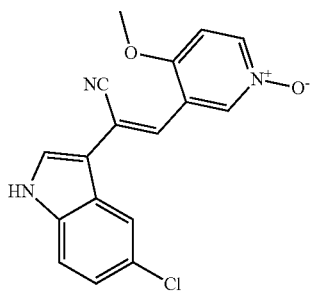 [SMILES: COc1cc[n+]([O-])cc1/C=C(\C#N)c1c[nH]c2ccc(Cl)cc12]

Method G (Z)-2-(5-chloro-1H-indol-3-yl)-3-(4-methoxypyridin-3-yl)acrylonitrile (30.0 mg), m-CPBA (33.0+16.0 mg). THF (1.5 mL). 16 h at room temperature. Trituration of the crude in AcOEt. Aspect of the pure product: yellow solid. (Yield: 80%).

ESI-MS: (M+H)+=326

$^1$H NMR (methanol-d4, 300 MHz) δ ppm: 8.84 (s, 1H), 8.33 (d, 1H), 7.94 (s, 1H), 7.81 (s, 1H), 7.59 (s, 1H), 7.50 (d, 1H), 7.35 (d, 1H), 7.26 (d, 1H), 4.11 (s, 3H).

Example 50

(Z)-2-(5-chloro-1H-indol-3-yl)-3-(4-hydroxypyridin-3-yl)acrylonitrile

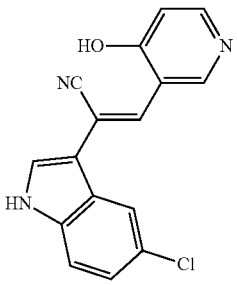

To a solution of (Z)-2-(5-chloro-1H-indol-3-yl)-3-(4-methoxypyridin-3-yl)acrylonitrile (30.0 mg, 1 eq) in NMP (0.2 mL) were added LiCl (41.0 mg, 10 eq) and p-Toluenesulfonic acid (166.0 mg, 10 eq). The resulting mixture was stirred 1 h 30 at 180° C. then cooled to room temperature and extracted with AcOEt. The combined organic layers were washed with water and dried over Na$_2$SO$_4$, filtrated and concentrated. The residue was taken off with a minimal amount of AcOEt and filtrated to give 18.0 mg of the title compound (Yield: 95%).

ESI-MS: (M+H)⁺=297
¹H NMR (methanol-d4, 300 MHz) δ ppm: 9.02 (s, 1H), 8.58 (d, 1H), 8.35 (s, 1H), 8.19 (s, 1H), 8.08 (d, 1H), 7.50-7.38 (m, 2H), 7.23 (d, 1H).

Example 51

(Z)-3-(2-(5-bromo-1H-indol-3-yl)-2-cyanovinyl)-4-hydroxybenzonitrile

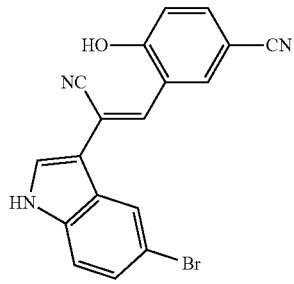 [SMILES: N#C/C(=C\c1cc(C#N)ccc1O)c1c[nH]c2ccc(Br)cc12]

To a solution of (Z)-3-(2-(5-bromo-1H-indol-3-yl)-2-cyanovinyl)-4-methoxybenzonitrile (30.0 mg, 1 eq) in NMP (0.2 mL) were added LiCl (33.0 mg, 10 eq) and p-Toluenesulfonic acid (136.0 mg, 10 eq). The resulting mixture was stirred 1 h 30 at 180° C. then cooled to room temperature and extracted with AcOEt. The combined organic layers were washed with water and dried over Na₂SO₄, filtrated and concentrated. The residue was purified by silicagel chromatography (CH₂Cl₂/MeOH, 100:0 to 90:10) to give 15.0 mg of the title compound (Yield: 52%).
ESI-MS: (M+H)⁺=366
¹H NMR (methanol-d4, 300 MHz) δ ppm: 8.27 (s, 1H), 8.18 (s, 1H), 7.90-7.53 (m, 2H), 7.53 (d, 1H), 7.45-7.13 (m, 3H).

Example 52

(Z)-3-(2-(5-chloro-1H-indol-3-yl)-2-cyanovinyl)-4-(trifluoromethoxy)benzonitrile

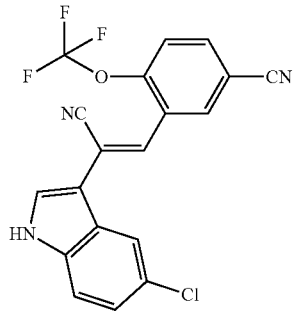

Method H tert-butyl-5-chloro-3-(cyanomethyl)-1H-indole-1-carboxylate (1 eq), NaH (3 eq), 3-formyl-4-(trifluoromethoxy)benzonitrile (1 eq). Room temperature hidden from light.
Aspect of the pure product: yellow solid. (Yield: 20%).
ESI-MS: (M+H)⁺=387

¹H NMR (methanol-d4, 300 MHz) δ ppm: 8.49 (d, 1H), 7.92 (d, 1H), 7.83 (s, 1H), 7.68 (s, 1H), 7.82 (s, 1H), 7.58-7.42 (m, 2H), 7.28 (d, 1H).

Example 53

(Z)-3-(2-(5-bromo-1H-indol-3-yl)-2-cyanovinyl)-4-(trifluoromethoxy)benzonitrile

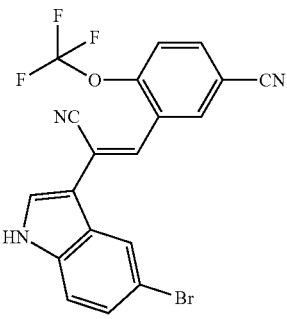 [SMILES: N#C/C(=C\c1cc(C#N)ccc1OC(F)(F)F)c1c[nH]c2ccc(Cl)cc12]

Method H tert-butyl-5-bromo-3-(cyanomethyl)-1H-indole-1-carboxylate (1 eq), NaH (3 eq), 3-formyl-4-(trifluoromethoxy)benzonitrile (1 eq). Room temperature hidden from light.
Aspect of the pure product: yellow solid. (Yield: 39%).
ESI-MS: (M+H)⁺=433
¹H NMR (methanol-d4, 300 MHz) δ ppm: 8.48 (s, 1H), 8.07 (s, 1H), 7.91 (d, 1H), 7.80 (s, 1H), 7.66 (s, 1H), 7.49-7.35 (m, 3H).

Example 54

(Z)-3-(2-cyano-2-(6-methoxy-1H-indol-3-yl)vinyl)-4-methoxybenzonitrile

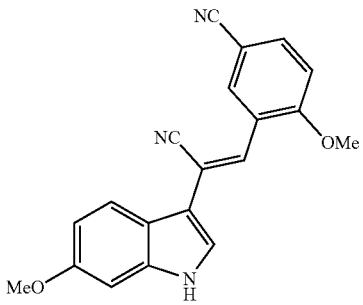 [SMILES: COc1ccc2c(/C(C#N)=C/c3cc(C#N)ccc3OC)c[nH]c2c1]

Method A tert-butyl 3-(cyanomethyl)-6-methoxy-1H-indole-1-carboxylate (175 mg), 3-formyl-4-methoxybenzonitrile (103 mg), NaH (34 mg), THF (2 ml). Reaction time 2 hours at RT. Poured in water, extracted with Ethyl acetate and trituration with diethyl ether. Aspect of the pure product: yellow solid. (Yield: 18%).
APCI-MS: (M+H)⁺=330
¹H NMR (300 MHz, CDCl₃) δ ppm 11.61 (s, 1H), 8.23 (d, J=1.7 Hz, 1H), 7.93 (dd, J=8.7, 2.0 Hz, 1H), 7.79 (d, J=8.8

Hz, 1H), 7.69 (s, 2H), 7.32 (d, J=8.7 Hz, 1H), 6.98 (d, J=2.2 Hz, 1H), 6.84 (dd, J=8.8, 2.2 Hz, 1H), 3.97 (s, 3H), 3.80 (s, 3H).

Some compounds of the previous examples have been the subject of tests which have demonstrated their specific relevance as inhibitors of MKlp2, and their cytotoxic effects on human cancer cells.

Preparation of Examples 55 to 79

Example 55

(Z)-2-(1-acetyl-5-bromo-1H-indol-3-yl)-3-(4-methoxypyridin-3-yl)acrylonitrile

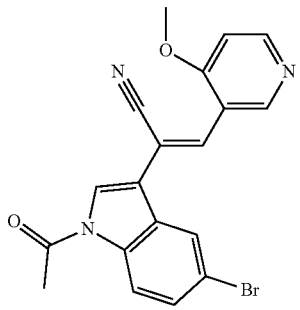 [SMILES: COc1ccncc1/C=C(\C#N)c1cn(C(C)=O)c2ccc(Br)cc12]

To a solution of (Z)-2-(5-chloro-1H-indol-3-yl)-3-(4-methoxypyridin-3-yl)acrylonitrile (50.0 mg, 1 eq) in THF (4 mL) were added pyridine (1 mL), NEt$_3$ (0.085 mL, 4.5 eq), DMAP (8.8 mg, 0.5 eq) and acetyl chloride (0.044 mL, 3.6 eq). The resulting mixture was stirred 48 h at RT, then neutralized with saturated NH$_4$Cl and extracted with AcOEt. The combined organic layers were washed with water and dried over Na$_2$SO$_4$, filtrated and concentrated. The residue was taken off with a minimal amount of MeOH and filtrated to give the title compound as an orange solid (36.0 mg, 65%).

ESI-MS: (M+H)$^+$=396
$^1$H NMR (300 MHz, CDCl$_3$) δ ppm 9.12 (s, 1H), 8.62 (d, J=5.3 Hz, 1H), 8.47 (d, J=8.9 Hz, 1H), 8.05 (d, J=1.9 Hz, 1H), 7.84 (s, 1H), 7.81 (s, 1H), 7.58 (dd, J=8.9 Hz, 1.9 Hz, 1H), 6.98 (s, 1H), 4.04 (s, 3H), 2.73 (s, 3H).

The following example was prepared as the previous method.

Example 56

(Z)-3-(2-(1-acetyl-5-bromo-1H-indol-3-yl)-2-cyanovinyl)-4-methoxybenzonitrile

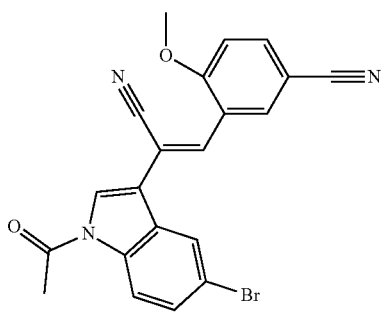 [SMILES: COc1ccc(C#N)cc1/C=C(\C#N)c1cn(C(C)=O)c2ccc(Br)cc12]

(Z)-3-(2-(5-bromo-1H-indol-3-yl)-2-cyanovinyl)-4-methoxybenzonitrile (30 mg), THF (2.4 ml), pyridine (0.6 mL), NEt$_3$ (0.051 mL, 4.5 eq), DMAP (5.3 mg, 0.5 eq) and acetyl chloride (0.027 mL, 3.6 eq). Reaction time 48 hours. Extracted with AcOEt, precipitated with MeOH. Aspect of the pure product: yellow solid. (Yield: 40%).

ESI-MS: (2M)$^+$=839
$^1$H NMR (300 MHz, CDCl$_3$) δ ppm 8.30 (d, J=1.7 Hz, 1H), 8.08 (d, J=1.7 Hz, 1H), 7.83-7.79 (m, 1H), 7.78 (s, 1H), 7.73 (s, 1H), 7.45-7.35 (m, 2H), 7.30 (s, 1H), 7.27 (s, 1H), 4.06 (s, 3H), 2.76 (s, 3H).

Example 57

(Z)-2-(5-bromo-1-pivaloyl-1H-indol-3-yl)-3-(4-methoxypyridin-3-yl)acrylonitrile

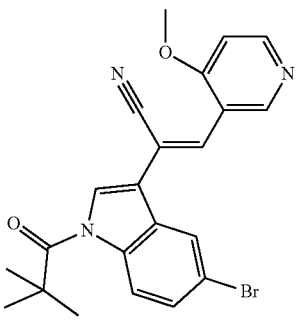 [SMILES: COc1ccncc1/C=C(\C#N)c1cn(C(=O)C(C)(C)C)c2ccc(Br)cc12]

To a solution of (Z)-2-(5-chloro-1H-indol-3-yl)-3-(4-methoxypyridin-3-yl)acrylonitrile (30.0 mg, 1 eq) in THF (1 mL) was added NaH (6.7 mg, 2 eq), The mixture was stirred 10 min at room temperature and pivaloyl chloride (0.011 mL, 1.1 eq) was added. The resulting solution was stirred 3 h at room temperature, poured in saturated NH$_4$Cl and extracted with CH$_2$Cl$_2$. The combined organic layers were dried over Na$_2$SO$_4$, filtrated and concentrated to give the title compound as a white solid (37.0 mg, 100%).

ESI-MS: (M+H)$^+$=438
$^1$H NMR (300 MHz, CD$_3$OD) δ ppm 9.20 (s, 1H), 8.82 (d, J=6.8 Hz, 1H), 8.45 (d, J=9.0 Hz, 1H), 8.35 (s, 1H), 8.13 (d, J=1.9 Hz, 1H), 7.88 (s, 1H), 7.68 (d, J=6.8 Hz, 1H), 7.60 (dd, J=9.0 Hz, 1.9 Hz, 1H), 4.30 (s, 3H), 1.57 (s, 9H).

The following examples were prepared as the previous method.

Example 58

(Z)-3-(2-(5-bromo-1-pivaloyl-1H-indol-3-yl)-2-cyanovinyl)-4-methoxybenzonitrile

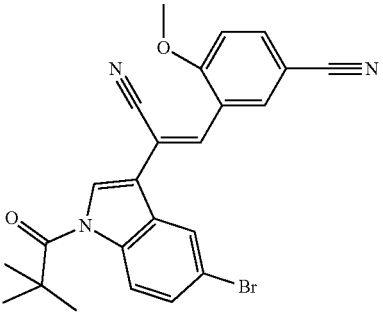 [SMILES: COc1ccc(C#N)cc1/C=C(\C#N)c1cn(C(=O)C(C)(C)C)c2ccc(Br)cc12]

(Z)-3-(2-(5-bromo-1H-indol-3-yl)-2-cyanovinyl)-4-methoxybenzonitrile (500 mg), THF (16 ml), NaH 60% in oil (0.105 g, 2 eq), pivaloyl chloride (0.216 mg, 1.35 eq). Reaction time 12 hours. Poured into AcOEt. Aspect of the pure product: white solid. (Yield: 100%).

ESI-MS: (M+H)$^+$=462

$^1$H NMR (300 MHz, DMSO-d$_6$) δ ppm 8.39 (s, 1H), 8.36 (s, 1H), 8.27 (s, 1H), 8.12 (s, 1H), 8.01 (dd, J=8.9 Hz, 1.5 Hz, 1H), 7.97 (s, 1H), 7.61 (dd, J=8.9 Hz, 1.5 Hz, 1H), 7.38 (d, J=8.9 Hz, 1H), 3.98 (s, 3H), 1.50 (s, 9H).

Example 59

(Z)-methyl-3-(5-bromo-3-(1-cyano-2-(4-methoxy-pyridin-3-yl)vinyl)-1H-indol-1-yl)-3-oxopropanoate

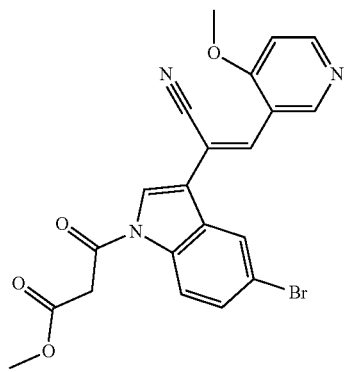 [SMILES: COC(=O)CC(=O)n1cc(/C(C#N)=C/c2cnccc2OC)c2cc(Br)ccc21]

(Z)-2-(5-chloro-1H-indol-3-yl)-3-(4-methoxypyridin-3-yl)acrylonitrile (100.0 mg), THF (4 mL), NaH 60% in oil (0.01 g, 1 eq), methylmalonyl chloride (0.042 g, 1.1 eq).

Reaction time: 12 hours. Purification by silicagel chromatography CH$_2$Cl$_2$/MeOH (100:0 to 90:10). Aspect of the pure product: yellow solid. (Yield: 72%).

ESI-MS: (M+H)$^+$=454

$^1$H NMR (300 MHz, CD$_3$OD) δ ppm 8.95 (s, 1H), 8.49 (s, 1H), 8.07 (s, 1H), 7.76-7.60 (m, 2H), 7.48-7.29 (m, 2H), 7.22 (s, 1H), 4.07 (s, 3H), 3.96 (s, 3H), 3.85 (s, 2H).

Example 60

(Z)-5-bromo-3-(1-cyano-2-(4-methoxypyridin-3-yl)vinyl)-N',N'-dimethyl-1H-indole-1-carbohydrazide

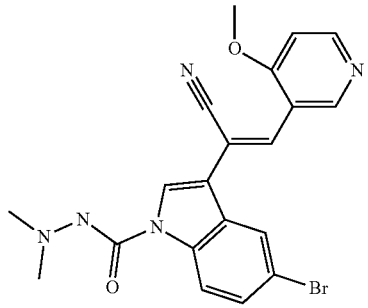 [SMILES: COc1ccncc1/C=C(\C#N)c1cn(C(=O)NN(C)C)c2ccc(Br)cc12]

To a mixture of (Z)-2-(5-chloro-1H-indol-3-yl)-3-(4-methoxypyridin-3-yl)acrylonitrile (50.0 mg, 1 eq) in CH$_2$Cl$_2$ was added DIPEA (0.024 mL, 1 eq) and triphosgene (64.0 mg, 0.37 eq). The mixture was stirred 20 min at room temperature and a solution of dimethylhydrazine (0.011 mL, 1 eq), DIPEA (0.024 mL, 1 eq) in CH$_2$Cl$_2$ was added. The mixture was stirred 2 h at room temperature and concentrated. The residue was purified by silicagel chromatography (CH$_2$Cl$_2$/MeOH (100:0 to 90:10) to give the title compound as a yellow solid (61%).

ESI-MS: (M+H)$^+$=440

$^1$H NMR (300 MHz, CD$_3$OD) δ ppm 9.00 (s, 1H), 8.53 (d, J=5.8 Hz, 1H), 8.34-8.27 (m, 1H), 8.14-8.10 (m, 2H), 7.88 (s, 1H), 7.52 (d, J=8.5 Hz, 1H), 7.25 (d, J=6.0 Hz, 1H), 4.08 (s, 3H), 2.56 (s, 6H).

Example 61

(Z)-2-(5-bromo-1-(2-(dimethylamino)acetyl)-1H-indol-3-yl)-3-(4-methoxypyridin-3-yl)acrylonitrile

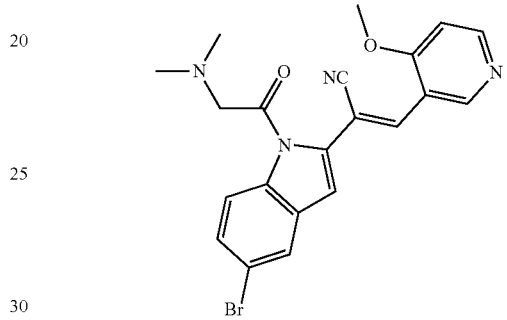

To a mixture of (Z)-3-(2-(5-bromo-1H-indol-3-yl)-2-cyanovinyl)-4-methoxypyridine (60 mg) in DMF (2 ml) was added 2-(dimethylamino)acetic acid (28 mg), PyBOP (132 mg), TEA (48 μl). The mixture was stirred at RT for 2 hours, poured in water and filtered. Aspect of the pure product: yellow solid. (Yield: 87%).

APCI-MS: (M+H)$^+$=438

$^1$H NMR (300 MHz, DMSO-d$_6$) δ ppm 8.89 (s, 1H), 8.58 (d, J=5.8 Hz, 1H), 8.38 (d, J=8.9 Hz, 1H), 8.33 (s, 1H), 8.19 (s, 1H), 7.94 (s, 1H), 7.66 (d, J=7.3 Hz, 1H), 7.25 (d, J=5.8 Hz, 1H), 4.26 (s, 2H), 3.97 (s, 3H), 2.54 (s, 6H).

Example 62

(Z)-2-(4-methylpiperazin-1-yl)ethyl 5-bromo-3-(1-cyano-2-(4-methoxypyridin-3-yl)vinyl)-1H-indole-1-carboxylate

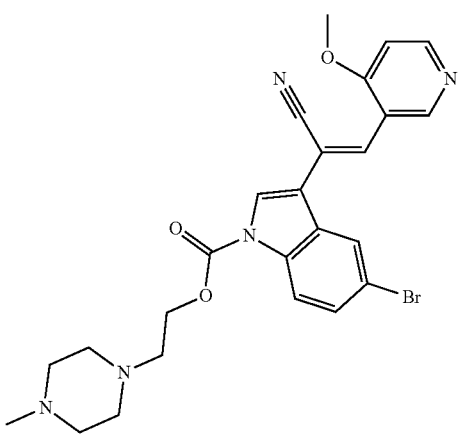 [SMILES: COc1ccncc1/C=C(\C#N)c1cn(C(=O)OCCN2CCN(C)CC2)c2ccc(Br)cc12]

To a mixture of (Z)-2-(5-chloro-1H-indol-3-yl)-3-(4-methoxypyridin-3-yl)acrylonitrile (30.0 mg, 1 eq) in CH$_2$Cl$_2$ (1 mL) was added NaH (7.0 mg, 1.2 eq). The mixture was stirred 10 min at room temperature and triphosgene (15.6 mg, 0.37 eq) was added. The mixture was stirred 3 h at room temperature and a solution of 2-(4-methylpiperazin-1-yl)ethanol (11.0 mg, 1 eq), DIPEA (0.024 mL, 1 eq) in CH$_2$Cl$_2$ was added. The mixture was stirred 2 h at room temperature and concentrated. The residue was purified by silicagel chromatography (CH$_2$Cl$_2$/MeOH (100:0 to 90:10) to give the title compound as a yellow solid (41%).

ESI-MS: (M+H)$^+$=524
$^1$H NMR (300 MHz, CD$_3$OD) δ ppm 8.95 (s, 1H), 8.48 (d, J=6.0 Hz, 1H), 8.07 (s, 1H), 7.73 (s, 1H), 7.69 (s, 1H), 7.48-7.29 (m, 2H), 7.21 (d, J=6.0 Hz, 1H), 4.07 (s, 3H), 3.69 (t, J=6.0 Hz, 2H), 2.74-2.40 (m, 6H), 2.29 (s, 4H).

Example 63

((Z)-3-(2-(5-bromo-1-(2-(dimethylamino)acetyl)-1H-indol-3-yl)-2-cyanovinyl)-4-methoxybenzonitrile

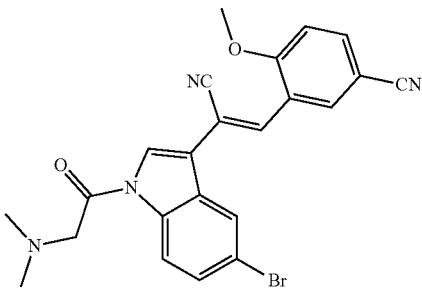 [SMILES: COc1ccc(C#N)cc1/C=C(\C#N)c1cn(C(=O)CN(C)C)c2ccc(Br)cc12]

(Z)-3-(2-(5-bromo-1H-indol-3-yl)-2-cyanovinyl)-4-methoxybenzonitrile (100 mg), DMF (2 ml), 2-(dimethylamino)acetic acid (34 mg), PyBOP (206 mg), TEA (74 µl). Reaction time 2 hours. Poured in water and diisopropylether. Aspect of the pure product: yellow solid. (Yield: 82%).

APCI-MS: (M+H)$^+$=462
$^1$H NMR (300 MHz, DMSO-d$_6$) δ ppm 8.38 (d, J=10.8 Hz, 2H), 8.29 (s, 1H), 8.16 (s, 1H), 8.00 (d, J=10.7 Hz, 1H), 7.94 (s, 1H), 7.64 (d, J=10.6 Hz, 1H), 7.37 (d, J=8.8 Hz, 1H), 3.96 (d, J=10.2 Hz, 5H), 2.38 (s, 6H).

Example 64

(Z)-tert-butyl 5-bromo-3-(1-cyano-2-(5-cyano-2-methoxyphenyl)vinyl)-1H-indole-1-carboxylate

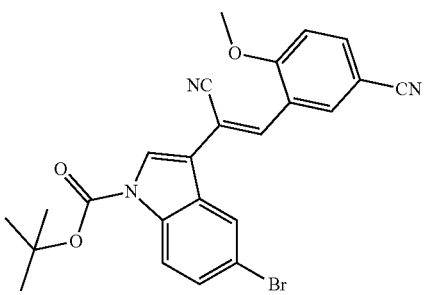 [SMILES: COc1ccc(C#N)cc1/C=C(\C#N)c1cn(C(=O)OC(C)(C)C)c2ccc(Br)cc12]

A mixture of (Z)-3-(2-(5-bromo-1H-indol-3-yl)-2-cyanovinyl)-4-methoxybenzonitrile (150 mg), Di-tert-butyldicarbonate (104 mg), DMAP (5 mg) in acetonitrile (3 ml) was stirred at RT for 0.25 h. The mixture was poured in water and filtered. Aspect of the pure product: yellow solid. (Yield: 88%).

APCI-MS: (M−H-Boc)=376
$^1$H NMR (300 MHz, DMSO-d$_6$) δ ppm 8.26 (d, J=1.8 Hz, 1H), 8.16 (d, J=1.8 Hz, 1H), 8.11 (d, J=8.9 Hz, 1H), 8.06 (s, 1H), 8.00 (dd, J=8.7, 2.1 Hz, 1H), 7.92 (s, 1H), 7.63 (dd, J=8.9, 1.9 Hz, 1H), 7.36 (d, J=8.8 Hz, 1H), 3.97 (s, 3H), 1.65 (s, 9H).

The following examples were prepared as the previous method.

Example 65

(R,Z)-benzyl-4-(5-bromo-3-(1-cyano-2-(5-cyano-2-methoxyphenyl)vinyl)-1H-indol-1-yl)-2-(tert-butoxycarbonylamino)-4-oxobutanoate

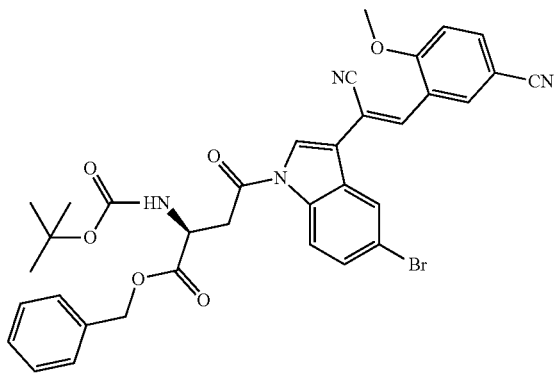 [SMILES: COc1ccc(C#N)cc1/C=C(\C#N)c1cn(C(=O)C[C@H](NC(=O)OC(C)(C)C)C(=O)OCc2ccccc2)c2ccc(Br)cc12]

((Z)-3-(2-(5-bromo-1H-indol-3-yl)-2-cyanovinyl)-4-methoxybenzonitrile (150 mg), DMF (4.5 ml), (S)-4-(benzyloxy)-3-(tert-butoxycarbonylamino)-4-oxobutanoic acid (160 mg), PyBOP (310 mg), TEA (1111). Reaction time 3 hours. Poured in water and diisopylether. Aspect of pure product: yellow solid. (Yield: 61%).

APCI-MS: (M−H-Boc)=583
$^1$H NMR (300 MHz, DMSO-d$_6$) δ ppm 8.37 (d, J=7.6 Hz, 2H), 8.30 (s, 1H), 8.17 (s, 1H), 8.08-7.90 (m, 2H), 7.64 (d, J=8.8 Hz, 1H), 7.46 (d, J=7.5 Hz, 1H), 7.43-7.25 (m, 6H), 5.15 (s, 2H), 4.64 (d, J=5.5 Hz, 1H), 3.98 (s, 3H), 3.60 (s, 2H), 1.36 (s, 9H).

Example 66

(R,Z)-tert-butyl-5-(5-bromo-3-(1-cyano-2-(5-cyano-2-methoxyphenyl)vinyl)-1H-indol-1-yl)-2-(tert-butoxycarbonylamino)-5-oxopentanoate

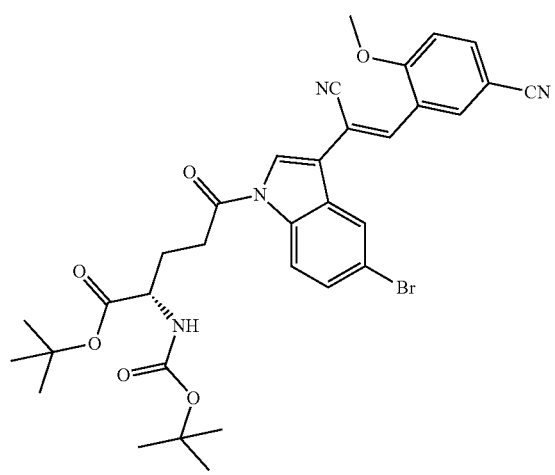 [SMILES: COc1ccc(C#N)cc1/C=C(\C#N)c1cn(C(=O)CC[C@H](NC(=O)OC(C)(C)C)C(=O)OC(C)(C)C)c2ccc(Br)cc12]

(Z)-3-(2-(5-bromo-1H-indol-3-yl)-2-cyanovinyl)-4-methoxybenzonitrile (200 mg), DMF (5 ml), (S)-5-tert-butoxy-4-(tert-butoxycarbonylamino)-5-oxopentanoic acid (201 mg), PyBOP (413 mg), TEA (147 µl). Reaction time 2 hours. Poured in water, extracted with AcOEt and trituration of the purified product with diisopropylether. Aspect of the pure product: yellow solid. (Yield: 53%).

APCI-MS: (M+H)$^+$=507

$^1$H NMR (300 MHz, DMSO-d$_6$) δ ppm 8.46-8.33 (m, 2H), 8.29 (d, J=1.8 Hz, 1H), 8.17 (d, J=1.7 Hz, 1H), 8.01 (dd, J=8.7, 2.0 Hz, 1H), 7.96 (s, 1H), 7.64 (dd, J=8.9, 1.7 Hz, 1H), 7.38 (d, J=8.8 Hz, 1H), 7.22 (d, J=7.9 Hz, 1H), 3.99 (s, 4H), 3.22 (d, J=6.1 Hz, 2H), 2.13 (m, 1H), 1.99 (m, 1H), 1.39 (d, J=9.2 Hz, 18H).

Example 67

(R,Z)-benzyl-2-amino-4-(5-bromo-3-(1-cyano-2-(5-cyano-2-methoxyphenyl)vinyl)-1H-indol-1-yl)-4-oxobutanoate

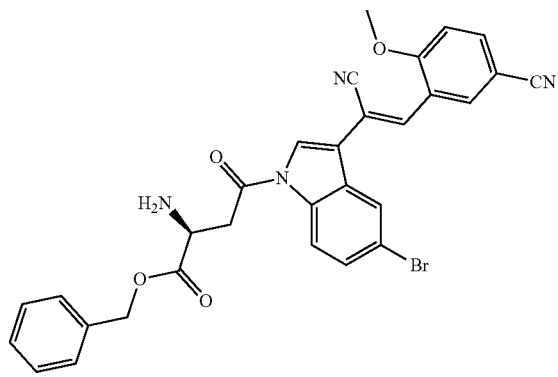 [SMILES: COc1ccc(C#N)cc1/C=C(\C#N)c1cn(C(=O)C[C@H](N)C(=O)OCc2ccccc2)c2ccc(Br)cc12]

A mixture of (R,Z)-benzyl 4-(5-bromo-3-(1-cyano-2-(5-cyano-2-methoxyphenyl)vinyl)-1H-indol-1-yl)-2-(tert-butoxycarbonylamino)-4-oxobutanoate (116 mg), HCl-Dioxanne 4M (1.5 ml) in EtOH (2 ml) was stirred at RT for 24 hours. After concentration to dryness, the residue was triturated with water and filtered. Aspect of the pure product: yellow solid. (Yield: 62%).

APCI-MS: (M+H)$^+$=583

$^1$H NMR (300 MHz, DMSO-d$_6$) δ ppm 8.39 (s, 1H), 8.35-8.30 (m, 2H), 8.20 (d, J=1.8 Hz, 1H), 8.03 (dd, J=8.7, 2.1 Hz, 1H), 7.98 (s, 1H), 7.68 (dd, J=8.9, 1.9 Hz, 1H), 7.37 (dd, J=10.4, 6.3 Hz, 3H), 7.33-7.25 (m, 3H), 5.25 (s, 2H), 4.62 (t, J=4.9 Hz, 1H), 3.99 (s, 3H), 3.86 (d, J=3.9 Hz, 2H).

Example 68

(Z)-3-(2-(5-bromo-1-(2-(4-methylpiperazin-1-yl)acetyl)-1H-indol-3-yl)-2-cyanovinyl)-4-methoxybenzonitrile

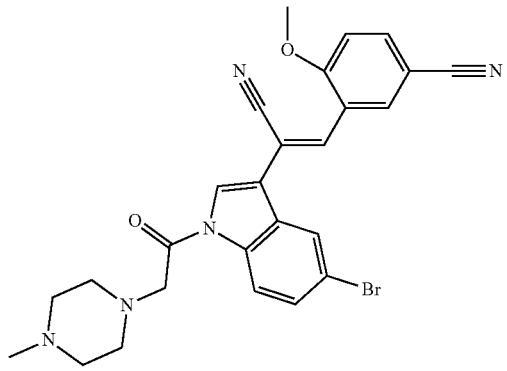 [SMILES: COc1ccc(C#N)cc1/C=C(\C#N)c1cn(C(=O)CN2CCN(C)CC2)c2ccc(Br)cc12]

(Z)-3-(2-(5-bromo-1H-indol-3-yl)-2-cyanovinyl)-4-methoxybenzonitrile (150 mg), 2-(4-methylpiperazin-1-yl) acetic acid (78 mg), PyBOP (310 mg), Triethylamine (0.11 ml), DMF (2 ml). Reaction time 5 h at RT. Poured in water and tritured with methylene chloride. Aspect of the product: yellow solid. (Yield: 92%).

APCI-MS: (M+H)$^+$=518

$^1$H NMR (300 MHz, DMSO-d$_6$) δ ppm 8.43-8.32 (m, 2H), 8.30 (d, J=1.8 Hz, 1H), 8.19 (d, J=1.7 Hz, 1H), 8.02 (dd, J=8.8, 2.0 Hz, 1H), 7.95 (s, 1H), 7.65 (dd, J=8.9, 1.8 Hz, 1H), 7.38 (d, J=8.8 Hz, 1H), 4.13 (s, 2H), 3.98 (s, 3H), 2.97 (m, 8H), 2.68 (s, 3H).

Example 69

(Z)-3-(2-(5-bromo-1-(2-(4-methylpiperazin-1-yl)acetyl)-1H-indol-3-yl)-2-cyanovinyl)-4-methoxybenzonitrile hydrochloride

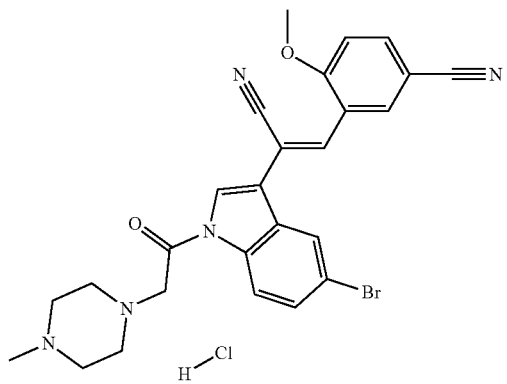 [SMILES: COc1ccc(C#N)cc1/C=C(\C#N)c1cn(C(=O)CN2CCN(C)CC2)c2ccc(Br)cc12 ; Cl]

A suspension of (Z)-3-(2-(5-bromo-1-(2-(4-methylpiperazin-1-yl)acetyl)-1H-indol-3-yl)-2-cyanovinyl)-4-methoxybenzonitrile (114 mg), HCl-Dioxane 4M (0.3 ml) in dioxane (1 ml) was stirred few minutes and concentrated under vacuum. Aspect of the product: yellow solid. (Yield: 95%).

APCI-MS: (M+H)$^+$=518

¹H NMR (300 MHz, DMSO-d₆) δ ppm 10.47 (s, 1H), 8.43-8.33 (m, 2H), 8.30 (d, J=1.8 Hz, 1H), 8.19 (d, J=1.8 Hz, 1H), 8.02 (dd, J=8.7, 2.1 Hz, 1H), 7.96 (s, 1H), 7.66 (dd, J=8.9, 1.9 Hz, 1H), 7.39 (d, J=8.8 Hz, 1H), 4.33 (s, 2H), 3.98 (s, 3H), 3.44 (d, J=11.5 Hz, 2H), 3.19 (s, 4H), 2.91 (s, 2H), 2.78 (s, 3H).

The following examples were prepared as the previous method.

Example 70

(S,Z)-3-(2-(1-(3-aminobutanoyl)-5-bromo-1H-indol-3-yl)-2-cyanovinyl)-4-methoxybenzonitrile hydrochloride

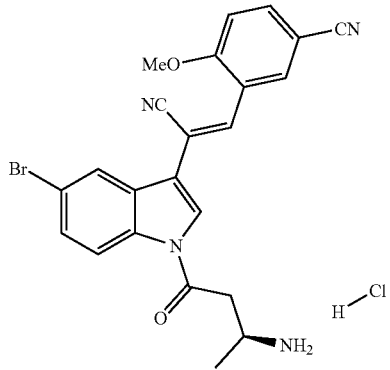 [SMILES: COc1ccc(C#N)cc1/C=C(\C#N)c1cn(C(=O)C[C@H](C)N)c2ccc(Br)cc12 ; Cl]

(S,Z)-tert-butyl 4-(5-bromo-3-(1-cyano-2-(5-cyano-2-methoxyphenyl)vinyl)-1H-indol-1-yl)-4-oxobutan-2-ylcarbamate (125 mg), HCl 37% (0.092 ml), EtOH (2 ml). Reaction time 1 h at reflux. Aspect of the pure product: yellow solid. (Yield: 65%).
APCI-MS: (M+H)⁺=463
¹H NMR (300 MHz, DMSO-d₆) δ ppm 8.44-8.34 (m, 2H), 8.29 (d, J=1.9 Hz, 1H), 8.19 (d, J=1.8 Hz, 1H), 8.13-7.82 (m, 5H), 7.66 (dd, J=8.9, 1.9 Hz, 1H), 7.37 (d, J=8.8 Hz, 1H), 3.97 (s, 3H), 3.76 (dd, J=13.0, 6.4 Hz, 1H), 3.53-3.42 (m, 2H), 1.34 (d, J=6.6 Hz, 3H).

Example 71

(Z)-3-(2-(1-(2-aminoacetyl)-5-bromo-1H-indol-3-yl)-2-cyanovinyl)-4-methoxybenzonitrile hydrochloride NC

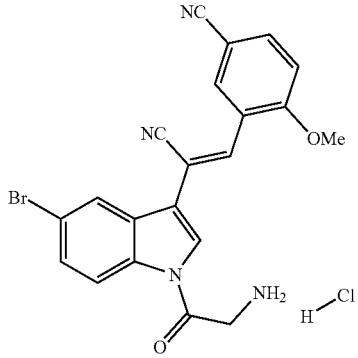

(Z)-3-(2-(5-bromo-1H-indol-3-yl)-2-cyanovinyl)-4-methoxybenzonitrile (150 mg), 2-(tert-butoxycarbonylamino)acetic acid (87 mg), PyBOP (310 mg), Triethylamine (0.11 ml), Reaction time 3 hours at RT. Then HCl 37% (0165 ml), DMF (2 ml) 2 hours at reflux. Aspect of the product: yellow solid. (Yield: 50%).
APCI-MS: (M+H)⁺=435
¹H NMR (300 MHz, DMSO-d₆) δ ppm 8.60 (s, 2H), 8.38 (d, J=8.4 Hz, 2H), 8.31 (d, J=1.9 Hz, 1H), 8.22 (d, J=1.8 Hz, 1H), 8.06-7.97 (m, 2H), 7.70 (dd, J=8.9, 1.9 Hz, 1H), 7.39 (d, J=8.8 Hz, 1H), 4.68 (s, 2H), 3.98 (s, 3H).

Example 72

(Z)-3-(2-(5-bromo-1-(2-(piperazin-1-yl)acetyl)-1H-indol-3-yl)-2-cyanovinyl)-4-methoxybenzonitrile hydrochloride NC

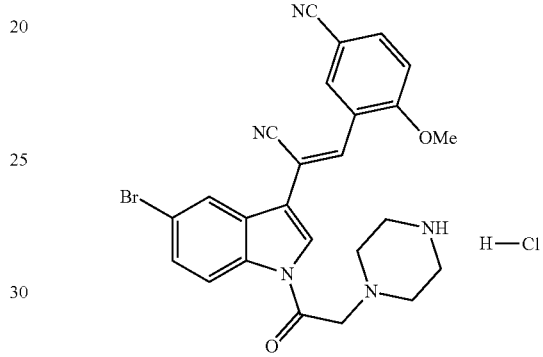

(Z)-3-(2-(5-bromo-1H-indol-3-yl)-2-cyanovinyl)-4-methoxybenzonitrile (150 mg), 2-(4-(tert-butoxycarbonyl)piperazin-1-yl)acetic acid (121 mg), PyBOP (310 mg), Triethylamine (011 ml), reaction time 3 hours at RT. Then HCl 37% (0.165 ml), DMF (2 ml) 2 hours at reflux. Aspect of the product: yellow solid. (Yield: 46%).
APCI-MS: (M+H)⁺=504
¹H NMR (300 MHz, DMSO-d₆) δ ppm 9.36 (s, 1H), 8.44-8.33 (m, 2H), 8.31 (d, J=1.8 Hz, 1H), 8.21 (d, J=1.8 Hz, 1H), 8.03 (dd, J=8.7, 2.1 Hz, 1H), 7.96 (s, 1H), 7.68 (dd, J=8.9, 1.8 Hz, 1H), 7.39 (d, J=8.8 Hz, 1H), 4.62 (s, 2H), 3.98 (s, 3H), 3.26 (d, J=17.6 Hz, 8H).

Example 73

(Z)-3-(2-(5-bromo-1-(2-(2-(2-methoxyethoxy)ethoxy)acetyl)-1H-indol-3-yl)-2-cyanovinyl)-4-methoxybenzonitrile

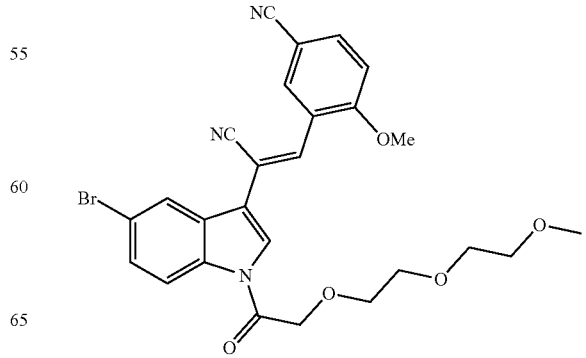

(Z)-3-(2-(5-bromo-1H-indol-3-yl)-2-cyanovinyl)-4-methoxybenzonitrile (150 mg), 2-(2-(2-methoxyethoxy)ethoxy)acetic acid (88 mg), PyBOP (310 mg), Triethylamine (0.11 ml), DMF (2 ml). Reaction time 18 hours at RT. Poured in water and washed with acetonitrile. Aspect of the product: yellow solid. (Yield: 33%).

APCI-MS: (M+H)⁺=538

¹H NMR (300 MHz, DMSO-d₆) δ ppm 8.39 (d, J=8.9 Hz, 1H), 8.33-8.23 (m, 2H), 8.18 (d, J=1.7 Hz, 1H), 8.01 (dd, J=8.7, 2.0 Hz, 1H), 7.94 (s, 1H), 7.65 (dd, J=8.9, 1.8 Hz, 1H), 7.38 (d, J=8.8 Hz, 1H), 4.93 (s, 2H), 3.98 (s, 3H), 3.81-3.68 (m, 2H), 3.60 (d, J=5.0 Hz, 2H), 3.55-3.48 (m, 2H), 3.39 (d, J=5.3 Hz, 2H), 3.19 (s, 3H).

Example 74

(S,Z)-3-(2-(1-(2-amino-3-hydroxypropanoyl)-5-bromo-1H-indol-3-yl)-2-cyanovinyl)-4-methoxybenzonitrile hydrochloride

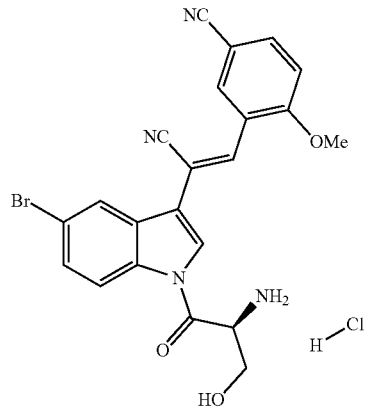 [SMILES: COc1ccc(C#N)cc1/C=C(\C#N)c1cn(C(=O)[C@@H](N)CO)c2ccc(Br)cc12 ; Cl]

(S,Z)-tert-butyl 1-(5-bromo-3-(1-cyano-2-(5-cyano-2-methoxyphenyl)vinyl)-1H-indol-1-yl)-3-hydroxy-1-oxopropan-2-ylcarbamate (220 mg), HCl 37% (110 μl), EtOH (2 ml). Reaction time 1 h at reflux. Aspect of the product: yellow solid. (Yield: 61%).

APCI-MS: (M+H)⁺=465

¹H NMR (300 MHz, DMSO-d₆) δ ppm 8.68 (d, J=19.5 Hz, 3H), 8.38 (d, J=8.9 Hz, 1H), 8.31 (d, J=1.9 Hz, 1H), 8.20 (d, J=1.8 Hz, 1H), 8.01 (dd, J=9.6, 2.9 Hz, 2H), 7.70 (dd, J=8.9, 1.9 Hz, 1H), 7.38 (d, J=8.8 Hz, 1H), 5.69 (s, 1H), 5.24 (s, 1H), 3.96 (d, J=5.0 Hz, 5H).

Example 75

(Z)-3-(2-(5-bromo-1-(5-oxopyrrolidine-2-carbonyl)-1H-indol-3-yl)-2-cyanovinyl)-4-methoxybenzonitrile

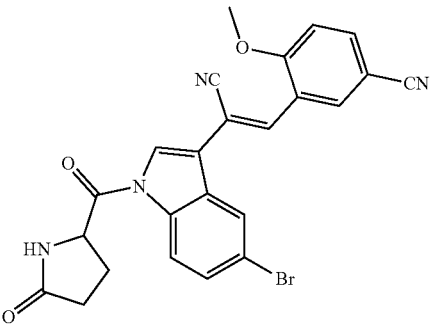 [SMILES: COc1ccc(C#N)cc1/C=C(\C#N)c1cn(C(=O)C2CCC(=O)N2)c2ccc(Br)cc12]

To a mixture of (Z)-3-(2-(5-bromo-1H-indol-3-yl)-2-cyanovinyl)-4-methoxybenzonitrile (100 mg) in DMF (2 ml) was added 5-oxopyrrolidine-2-carboxylic acid (37 mg), BOP (128 mg), TEA (581). The mixture was stirred at RT for 3 hours, poured in water and filtered. Aspect of the pure product: yellow solid. (Yield: 60%).

ESI+MS: (M+H)⁺=490

¹H NMR (300 MHz, MeOD-d₆) δ ppm 8.44 (s, 1H), 8.22 (s, 1H), 8.08 (s, 1H), 7.91 (dd, J=8.8, 2.0 Hz, 1H), 7.95 (s, 1H), 7.65 (dd, J=14.0, 2.1 Hz, 2H), 7.71 (s, 1H), 7.40-7.31 (m, 2H), 4.21 (t, J=6.0 Hz, 1H), 3.98 (s, 3H), 2.73-2.13 (m, 4H).

Example 76

(R,Z)-3-(2-(5-bromo-1-(2,6-diaminohexanoyl)-1H-indol-3-yl)-2-cyanovinyl)-4-methoxybenzonitrile dihydrochloride

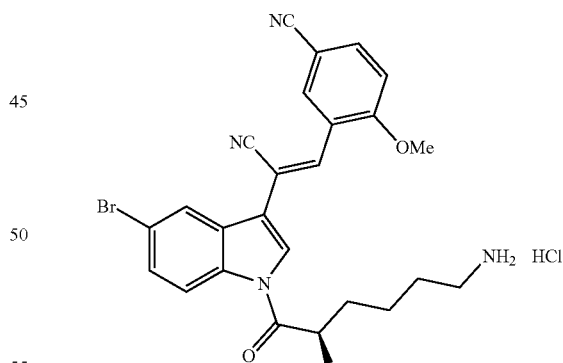

(R,Z)-tert-butyl-6-(5-bromo-3-(1-cyano-2-(5-cyano-2-methoxyphenyl)vinyl)-1H-indol-1-yl)-6-oxohexane-1,5-diyl dicarbamate (320 mg), HCl 37% (164 μl), EtOH (3 ml). Reaction time 1 hour at reflux. Aspect of the pure product: pale yellow solid. (Yield: 67%).

APCI-MS: (M+H)⁺=506

¹H NMR (300 MHz, CD₃OD) δ ppm 8.68 (s, 3H), 8.40 (d, J=8.9 Hz, 1H), 8.32 (d, J=1.7 Hz, 1H), 8.22 (d, J=1.8 Hz, 1H), 8.07-8.00 (m, 2H), 7.91 (s, 2H), 7.71 (dd, J=8.9, 1.8 Hz, 1H), 7.40 (d, J=8.8 Hz, 1H), 5.19 (s, 1H), 3.99 (s, 3H), 2.72 (s, 2H), 1.96 (s, 2H), 1.46 (m, 4H).

Example 77

(Z)-diethyl (2-(5-bromo-3-(1-cyano-2-(5-cyano-2-methoxyphenyl)vinyl)-1H-indol-1-yl)-2-oxoethyl) phosphonate

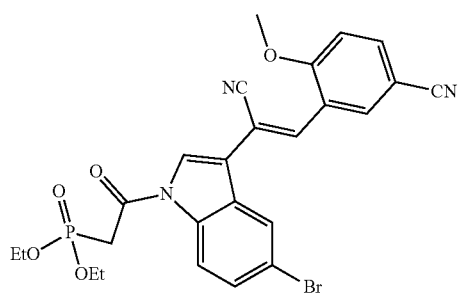 [SMILES: CCOP(=O)(CC(=O)n1cc(/C(C#N)=C/c2cc(C#N)ccc2OC)c2cc(Br)ccc21)OCC]

To a solution of (Z)-2-(5-chloro-1H-indol-3-yl)-3-(4-methoxypyridin-3-yl)acrylonitrile (0.382 g, 1 eq) in THF (6 mL) was added NaH 60% in mineral oil (0.048 g, 1.2 eq). The resulting solution was stirred 30 min at room temperature and a solution of diethyl (2-chloro-2-oxoethyl)phosphonate (0.216 g, 1 eq) in THF (3 mL). The mixture was stirred overnight, quenched with saturated NH$_4$Cl, extracted with AcOEt, dried over Na$_2$SO$_4$, filtrated and concentrated. The residue was purified by silicagel chromatography CH$_2$Cl$_2$/MeOH (100:0 to 90:10) to give the title compound as yellow solid (36%).

ESI-MS: (M+H)$^+$=556

$^1$H NMR (300 MHz, CD$_3$OD) δ ppm 8.28 (s, 1H), 8.07 (s, 1H), 7.81 (dd, J=8.5 Hz, 1.8 Hz, 1H), 7.43 (d, J=8.9 Hz, 1H), 7.36 (d, J=8.9 Hz, 1H), 7.29 (d, J=8.5 Hz, 1H), 4.2 (q, J=7.0 Hz, 4H), 4.06 (s, 3H), 3.10 (d, J=20.0 Hz, 2H), 1.36 (t, J=7.0 Hz, 6H).

Example 78

(Z)-2-(5-bromo-3-(1-cyano-2-(5-cyano-2-methoxyphenyl)vinyl)-1H-indol-1-yl)-2-oxoethyl diphosphate, tetrabutylammonium salt

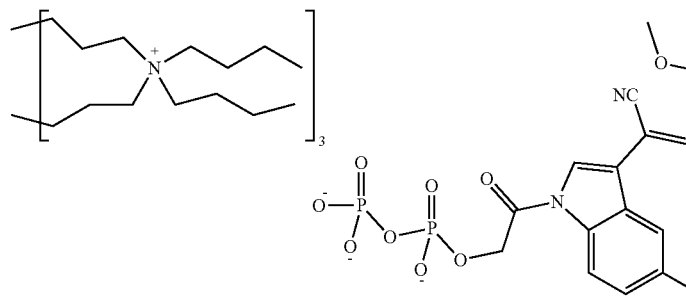

To a solution of (Z)-3-(2-(5-bromo-1-(2-bromoacetyl)-1H-indol-3-yl)-2-cyanovinyl)-4-methoxybenzonitrile (0.036 g, 1 eq) in AcCN (1 mL) was added Tributylammonium pyrophosphate (0.092 g, 1.3 eq). The reaction mixture was stirred 48 h at room temperature and concentrated to give the title compound as yellow solid (60%).

ESI-MS: (M−H)$^+$=590

$^1$H NMR (300 MHz, CD$_3$OD) δ ppm 8.24 (d, J=1.9 Hz, 1H), 8.00 (s, 1H), 7.75 (dd, J=8.7 Hz, 2.1 Hz, 1H), 7.71-7.67 (m, 2H), 7.50 (d, J=8.7 Hz, 1H), 7.35 (s, 1H), 7.31 (dd, J=8.7 Hz, 1.7 Hz, 1H), 7.25 (d, J=8.7 Hz, 1H), 4.97 (d, J=20 Hz, 2H), 4.03 (s, 3H), 4.06 (s, 3H), 3.27-3.22 (m, 24H), 1.72-1.62 (m, 24H), 1.49-1.37 (m, 24H), 1.03 (t, J=7.2 Hz, 36H).

Example 79

(Z)-3-(5-bromo-3-(1-cyano-2-(5-cyano-2-methoxyphenyl)vinyl)-1H-indol-1-yl)-3-oxopropyl dihydrogen phosphate

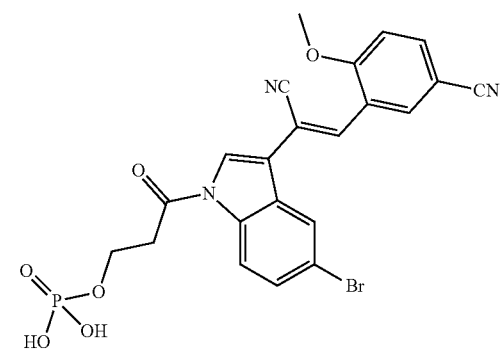 [SMILES: COc1ccc(C#N)cc1/C=C(\C#N)c1cn(C(=O)CCOP(=O)(O)O)c2ccc(Br)cc12]

To a solution of (Z)-3-(2-(5-bromo-1-(3-hydroxypropanoyl)-1H-indol-3-yl)-2-cyanovinyl)-4-methoxybenzonitrile (0.047 g, 1 eq) in THF (3.1 mL) and AcCN (3.6 mL) was added DIPEA (90 υL). The reaction mixture was cooled to 0° C. and POCl$_3$ (0.078 mL, 8 eq) was added dropwise. The resulting solution was stirred 3 h at 0° C. and 1 M KH$_2$PO$_4$ (PH=4) (5 mL) was added dropwise. The mixture was stirred overnight and concentrated. The residue was purified by C18 flash chromatography H$_2$O/MeOH (100:0 to 0:100) to give the title compound as yellow solid (40%).

$^1$H NMR (300 MHz, CD$_3$OD) δ ppm 8.30 (s, 1H), 8.04 (s, 1H), 8.00-7.97 (m, 2H), 7.83-7.80 (m, 2H), 7.40 (dd, J=9.0 Hz, 1.5 Hz, 1H), 7.29 (d, J=8.7 Hz, 1H), 4.06 (s, 3H), 3.73 (m, 2H), 3.23 (m, 2H).

Evaluation of Inhibitory Effects on the Microtubule Stimulated ATPase Activity of the MKlp2 Motor Domain.

Material and Methods

MKlp2 ATPase activity was measured by monitoring real time free phosphate generation using the Kinesin ELIPA Assay Kit. The assay is based upon an absorbance shift (330 nm-360 nm) that occurs when 2-amino-6-mercapto-7-methylpurine ribonucleoside (MESG) is catalytically converted to 2-amino-6-mercapto-7-methylpurine in the presence of inorganic phosphate (Pi). One molecule of Pi will yield one molecule of 2-amino-6-mercapto-7-methylpurine in an essentially irreversible reaction. Hence, the absorbance at 360 nm is directly proportional to the amount of Pi generated in the kinesin ATPase reaction.

Human recombinant MKlp2 motor domain$_{1-519}$, His tagged (Cytoskeleton, Cat. #MP05), plus porcine brain microtubules (Cytoskeleton, cat. #MT002) were used.

All experiments were performed at 22° C.

Condition 1, compound preparation.

The compounds were dissolved in DMSO at 30× the maximum concentration to be tested. Each compound had a seven point dose-response evaluation, with final concentrations 100, 33, 11, 3.7, 1.2, 0.4, 0.13 µM. DMSO solutions were pipetted directly into each well.

Condition 2, reaction's "motor mix".

The following were mixed sequentially in the specified order at RT to obtain the "motor mix".

20 mL: 15 mM Pipes-NaOH pH 7.0, 10 mM MgCl$_2$, 30 µM Tx (Buffer 1).

10 mL: 5×MSEG (ELIPA 1 reagent, Cat. #BK051).

10 mL: 2.5 mg/mL porcine brain microtubules (3×10 mg Cat. #MT002-XL resuspended in 12 mL of Buffer 1).

0.25 mL: 500 µg/mL MKlp2 protein.

0.5 mL: 100×PNP (ELIPA 2 reagent, cat. #BK051).

Condition 3, reaction initiation.

The motor mix was pipetted into each well to obtain 80% of total volume. The reaction was initiated by adding a 20% of total volume of 5 mM ATP into each well.

The reactions were measured in a SpectraMax M2 (Molecular Devices) set in kinetic mode and 360 nm absorbance wavelength. The start protocol was 5 second rapid circular mixing, 21 readings, 30 seconds apart.

IC50 values were determined as the concentration to inhibit 50% of the MKlp2 ATPase activity.

Evaluation of Cytotoxicity Effects on Human Cancer Cells

Material and Methods

The effects of the compounds of the invention on the viability of human cancer cells were studied on various human cancer cell lines of differing tissue origins (A549, NCI-H460: lung cancer; MDA-MB-231: breast cancer; HCT-116, HT-29: colon cancer; MIA-PaCa-2: pancreatic cancer; K562: leukaemia). All cell lines were obtained from ATCC or ECACC.

Cells were cultured in the culture media described below, under a 37° C., 5% CO$_2$ humidified atmosphere, according to a standard operating procedure.

Organ Cell Line Culture Medium

A549: RPMI 1640+10% FBS+2 mM sodium pyruvate

NCI-H460: RPMI 1640+10% FBS+10 mM HEPES+1 mM Sodium pyruvate+2.5 g/l glucose

HCT-116: Mc Coy's 5a+10% FBS+0.5 mM Ultraglutamine

HT-29: Mc Coy's 5a+10% FBS+0.5 mM Ultraglutamine

MDA-MB-231: Ham's F12+10% FBS

K562: RPMI 1640+10% FBS+2 mM ultraglutamine

MIA-PaCa-2: DMEM+10% FBS

On D0, the cells were plated in 90 µl in 96 wells plates at densities ranging from 500 to 5,000 cells per well.

On D1, the cells were treated as described below: the compounds of invention were diluted in DMSO in order to obtain a concentration of 5 mM. This solution was serially diluted in PBS+10% FBS in order to obtain the concentrations of 500.000, 166.667, 55.555, 18.518, 6.173, 2.058, 0.686, 0.229, 0.076 and 0.025 µM. The addition of 10 µl in each well allowed the testing concentrations of 50.000, 16.6667, 5.5555, 1.8518, 0.6173, 0.2058, 0.0686, 0.0229, 0.0076 and 0.0025 µM.

Following addition of the test substance the cells were protected from light. The solvents (DMSO and specific control solvent were added at the maximal concentration: 10 µl/well (3 wells/condition)).

On D4, the Cell Proliferation Reagent WST-1 was added to each well (10 µl/well), according to a standard operating procedure. The cells were then incubated for 30 min to 4 h at 37° C.-5% CO$_2$. After these incubations, the 96-well plates were shaken thoroughly for 1 min with Multiskan® EX apparatus (Thermo Labsystems, France). The absorbence was measured at 450 nm, the reference wavelength being 620 nm. The analysis of the results was performed with the Ascent software 2.6 (Thermo Labsystems, France), Microsoft Excel 2003 and GraphPad Prism 4.03 softwares to give the concentration of the compounds that induces the death of 50% of the cells (IC50).

The results for some compounds considered in above-cited examples in term of inhibition of microtubule stimulated ATPase activity of MKlp2 are illustrated in Tables 3 and 6 hereafter.

The results for some compounds considered in above-cited examples in term of cytotoxicity on K562 cells are illustrated in Table 4 and 6 hereafter.

The results for some compounds considered in above-cited examples in term of cytotoxicity on other human cancer cells are illustrated in Table 5 hereafter.

TABLE 3

|  | X | R1 | R1' | R2 | R3 | MKlp2 IC50 (µM) |
|---|---|---|---|---|---|---|
| WO2010/150211-Example 1 | N | H | H | H | H | 3.8 |
| WO2010/150211-Example 4 | N | —O—CH$_3$ | H | H | H | 4.2 |
| WO2010/150211-Example 22 | N | —O—CH$_2$—CH$_3$ | H | H | H | 5.2 |
| WO2010/150211-Example 23 | N | —O—CH—(CH$_3$)$_2$ | H | H | H | 5.2 |
| WO2010/150211-Example 24 | N | —Cl | H | H | H | 1.1 |
| WO2010/150211-Example 28 | N | —O—CH$_3$ | H | H | —F | 2.4 |
| WO2010/150211-Example 31 | N | —O—CH$_3$ | H | —CH$_3$ | H | 2.3 |
| WO2010/150211-Example 47 | N | —O—CH$_3$ | H | —Cl | H | 1.6 |
| WO2010/150211-Example 37 | N | —Br | H | H | H | 1.5 |
| WO2010/150211-Example 26 | N | H | —O—CH$_3$ | H | H | 26.5 |
| WO2010/150211-Example 52 | N | —O—CH$_3$ | H | H | —O—CH$_3$ | 12.6 |
| WO2010/150211-Example 30 | C—CN | —O—CH$_3$ | H | H | H | 4.4 |
| Example 2 | N | —O—CH$_3$ | H | —O—CH$_2$—OH$_3$ | H | 0.3 |
| Example 3 | N | —Cl | H | —Cl | H | 0.8 |
| Example 4 | N | —Br | H | —Cl | H | 0.7 |
| Example 5 | N | —Br | H | —O—CH$_3$ | H | 0.05 |
| Example 5b | N | —Br | H | —O—CH$_3$ | H | 0.61 |
| Example 6 | N | —Cl | H | —N—(CH$_3$)$_2$ | H | 0.5 |
| Example 7 | N | —Cl | H | —N—(CH$_3$)$_2$ | H | 0.8 |

TABLE 3-continued

|  | X | R1 | R1' | R2 | R3 | MKlp2 IC50 (μM) |
|---|---|---|---|---|---|---|
| Example 8 | N | —Br | H | —N—(CH3)$_2$ | H | 0.9 |
| Example 9 | N | —Cl | H | —O—CH$_3$ | H | 0.1 |
| Example 10 | N | —Cl | H | —O—C$_6$H$_5$ | H | 0.3 |
| Example 11 | N | —Br | H | —O—C$_6$H$_5$ | H | 0.5 |
| Example 12 | N | —O—CH$_3$ | H | —O—CH$_3$ | H | 0.3 |
| Example 13 | N | —Br | H | —O—CH$_2$—CH$_3$ | H | 0.1 |
| Example 14 | N | —Br | H | —O—CH—(CH$_3$)$_2$ | H | 0.2 |
| Example 15 | N | —Br | H | —S—CH$_3$ | H | 0.2 |
| Example 16 | N | —Br | H | —S—CH$_2$—CH$_3$ | H | 0.3 |
| Example 17 | N | —Br | H | —(C$_6$H$_4$)—3-Br | H | 0.3 |
| Example 18 | N | —Cl | H | —(C$_6$H$_4$)—3-Br | H | 0.3 |
| Example 19 | N | —Br | H | —S—C$_6$H$_5$ | H | 0.3 |
| Example 20 | N | —Br | H | —S—CH$_2$—C$_6$H$_5$ | H | 0.2 |
| Example 21 | N | —Br | H | —S—C$_6$H$_5$-3,4-(—OCH$_3$)$_2$ | H | 0.4 |
| Example 22 | N | —Br | H | —O—C$_6$H$_5$—4-F | H | 0.09 |
| Example 23 | N | —Cl | H | —O—C$_6$H$_5$—4-F | H | 0.09 |
| Example 24 | N | —Br | H | —N—(CH$_2$CH$_3$)$_2$ | H | 1.1 |
| Example 25 | N | —Br | H | —C$_6$H$_5$—4-CF$_3$ | H | 0.4 |
| Example 26 | N | —Cl | H | —C$_6$H$_5$—4-CF$_3$ | H | 0.5 |
| Example 27 | N | —Cl | H | —S—C$_6$H$_5$—4-F | H | 0.3 |
| Example 28 | N | —Br | H | —S—C$_6$H$_5$—4-F | H | 0.09 |
| Example 29 | N | —Cl | H | —C$_4$H$_3$O | H | 0.03 |
| Example 30 | N | —Cl | H | —S—C$_5$H$_4$N | H | 0.3 |
| Example 31 | N | —Br | H | —S—C$_5$H$_4$N | H | 0.4 |
| Example 32 | N | —Br | H | —C$_2$H$_2$N$_3$ | H | 0.06 |
| Example 33 | N | —Cl | H | —C$_2$H$_2$N$_3$ | H | 0.1 |
| Example 34 | N | —Br | H | —C$_4$H$_3$O | H | 0.07 |
| Example 34b | N | —Br | H | —C$_4$H$_3$O | H | 0.96 |
| Example 35 | N | —Cl | H | —O—CH$_3$ | H | <0.07 |
| Example 36 | N | —Br | H | —S—(CH$_2$)$_2$—N—(CH$_3$)$_2$ | H | 0.3 |
| Example 37 | C—CN | —Br | H | —O—C$_6$H$_5$—4-F | H | 0.9 |
| Example 38 | C—CN | —Br | H | —O—CH$_3$ | H | 0.2 |
| Example 39 | C—CN | —Br | H | —N—(CH$_3$)$_2$ | H | 0.2 |
| Example 40 | C—CN | —Cl | H | —O—CH$_3$ | H | 0.2 |
| Example 41 | C—CN | —Cl | H | —N—(CH$_3$)$_2$ | H | 0.4 |
| Example 42 | C—CN | —Cl | H | —S—CH$_2$CH$_3$ | H | 0.6 |
| Example 45 | N | H | —Br | —O—CH$_3$ | H | 0.2 |
| Example 46 | N | H | —F | —O—CH$_3$ | H | 0.12 |
| Example 47 | N | H | —Cl | —O—CH$_3$ | H | 0.2 |
| Example 48 | N$^+$—O$^-$ | —Br | H | —C$_4$H$_3$O | H | 0.73 |
| Example 49 | N$^+$—O$^-$ | —Cl | H | —O—CH$_3$ | H | 0.56 |
| Example 54 | C—CN | H | O—CH$_3$ | —O—CH$_3$ | H | 1.4 |
| Example 59: Prodrug with Ra = COCH$_2$CO$_2$CH$_3$ | N | Br | H | —O—CH$_3$ | H | 0.57 |
| Example 62: Prodrug with Ra = CO$_2$(CH$_2$)$_2$-piperazinyl-CH$_3$ | N | Br | H | —O—CH$_3$ | H | 0.35 |

TABLE 4

|  | X | R1 | R1' | R2 | R3 | K562 IC50 (μM) |
|---|---|---|---|---|---|---|
| WO2010/150211-Example 1 | N | H | H | H | H | 21.4 |
| Example 3 | N | —Cl | H | —Cl | H | 3.6 |
| Example 4 | N | —Br | H | —Cl | H | 1.4 |
| Example 5 | N | —Br | H | —O—CH$_3$ | H | 0.8 |
| Example 5b | N | —Br | H | —O—CH$_3$ | H | 3.92 |
| Example 34b | N | —Br | H | —C$_4$H$_3$O | H | 14.26 |
| Example 8 | N | —Br | H | —N—(CH$_3$)$_2$ | H | 7.5 |
| Example 9 | N | —Cl | H | —O—CH$_3$ | H | 1.4 |
| Example 12 | N | —O—CH$_3$ | H | —O—CH$_3$ | H | 0.9 |
| Example 15 | N | —Br | H | —S—CH$_3$ | H | 2.9 |
| Example 24 | N | —Br | H | —N—(CH$_2$CH$_3$)$_2$ | H | 3.1 |
| Example 29 | N | —Cl | H | —C$_4$H$_3$O | H | 4.7 |
| Example 34 | N | —Br | H | —C$_4$H$_3$O | H | 2.2 |
| Example 38 | C—CN | —Br | H | —O—CH$_3$ | H | 0.03 |
| Example 39 | C—CN | —Br | H | —N—(CH$_3$)$_2$ | H | 0.6 |
| Example 48 | N$^+$—O$^-$ | —Br | H | —C$_4$H$_3$O | H | 6.71 |
| Example 49 | N$^+$—O$^-$ | —Cl | H | —O—CH$_3$ | H | 9.23 |
| Example 50 | N | Cl | H | —OH | H | 14.72 |
| Example 51 | C—CN | Br | H | —OH | H | 0.5 |
| Example 52 | C—CN | Cl | H | —OCF$_3$ | H | 0.85 |
| Example 53 | C—CN | Br | H | —OCF$_3$ | H | 0.38 |
| Example 54 | C—CN | H | —O—CH$_3$ | —O—CH$_3$ | H | 0.02 |

TABLE 5

|  | X | R1 | R1' | R2 | R3 | IC50 (μM) |
|---|---|---|---|---|---|---|
| Example 5 | N | —Br | H | —O—CH$_3$ | H | HCT-116: 0.7<br>MDA-MB-231: 1.7<br>MIA-PaCa-2: 0.7<br>NCIH460: 0.9 |
| Example 38 | C—CN | —Br | H | —O—CH$_3$ | H | HCT-116: 0.06<br>MDA-MB-231: 0.07<br>MIA-PaCa-2: 0.04<br>NCIH460: 0.04 |
| Example 39 | C—CN | —Br | H | —N—(CH$_3$)$_2$ | H | A549: 0.5<br>HT-29: 0.3<br>MDA-MB-231: 0.3<br>MIA-PaCa-2: 0.2 |

TABLE 6

|  | X | R1 | R1' | R2 | R3 | Z/E | Ra | MKlp2 IC50 (μM) | K562 IC50 (μM) |
|---|---|---|---|---|---|---|---|---|---|
| Example 55 | N | Br | H | OCH$_3$ | H | Z | COCH$_3$ | 13.7 | 0.55 |
| Example 56 | C—CN | Br | H | OCH$_3$ | H | Z | COCH$_3$ | 16.7 | 0.25 |
| Example 57 | N | Br | H | OCH$_3$ | H | Z | COC(CH$_3$)$_3$ | 20 | 0.2 |
| Example 58 | C—CN | Br | H | OCH$_3$ | H | Z | COC(CH$_3$)$_3$ | 7.5 | 0.06 |
| Example 61 | N | Br | H | OCH$_3$ | H | Z | COCH$_2$N(CH$_3$)$_2$ | 0.4 | 0.33 |
| Example 63 | C—CN | Br | H | OCH$_3$ | H | Z | COCH$_2$N(CH$_3$)$_2$ | 10.6 | 0.04 |
| Example 64 | C—CN | Br | H | OCH$_3$ | H | Z | CO$_2$C(CH$_3$)$_3$ | 19.6 | 0.24 |
| Example 65 | C—CN | Br | H | OCH$_3$ | H | Z | COCH$_2$—CH(NHBoc)Cbz | 10.1 | 0.04 |
| Example 66 | C—CN | Br | H | OCH$_3$ | H | Z | CO(CH$_2$)$_2$—CH(Boc)-NHBoc | 5.4 | 0.03 |
| Example 67 | C—CN | Br | H | OCH$_3$ | H | Z | COCH$_2$—CH(NH$_2$)—Cbz | 3.1 | 0.04 |
| Example 68 | C—CN | Br | H | OCH$_3$ | H | Z | CO—CH$_2$-piperazinyl-CH$_3$ | >50 | 0.03 |
| Example 69 | C—CN | Br | H | OCH$_3$ | H | Z | CO—CH$_2$-piperazinyl-CH$_3$•HCl | >50 | 0.03 |
| Example 70 | C—CN | Br | H | OCH$_3$ | H | Z | COCH$_2$—CH(CH$_3$)NH$_2$ | >50 | 0.01 |
| Example 71 | C—CN | Br | H | OCH$_3$ | H | Z | COCH$_2$NH$_2$•HCl | 1.9 | 0.01 |
| Example 72 | C—CN | Br | H | OCH$_3$ | H | Z | CO—CH$_2$-piperazinyl•HCl | >50 | 0.01 |
| Example 73 | C—CN | Br | H | OCH$_3$ | H | Z | COCH$_2$O(CH$_2$)$_2$O(CH$_2$)$_2$OCH$_3$ | >50 | 0.03 |
| Example 74 | C—CN | Br | H | OCH$_3$ | H | Z | COCH(NH$_2$)CH$_2$OH | 2.1 | 0.01 |
| Example 75 | C—CN | Br | H | OCH$_3$ | H | Z | CO-oxopyrrolidine | 4.6 | 0.02 |
| Exemple 76 | C—CN | Br | H | OCH$_3$ | H | Z | COCH(NH$_2$)—(CH$_2$)4NH$_2$ | 1.3 | 0.04 |
| Exemple 79 | C—CN | Br | H | OCH$_3$ | H | Z | CO(CH$_2$)$_2$PO$_4$H$_2$ | >50 | 0.4 |

Stability Studies in Mouse or Human Plasma

The study was to evaluate the stability of the disclosed compounds after incubation in mouse or human plasma and to measure the metabolites formed. For the disclosed compound, a stock solution was prepared at 200 μM in DMSO. This solution was then 100-fold diluted in 1 ml of mouse or human plasma in order to obtain the required concentration of 2 μM. One aliquot of 100 μl was taken (T0) and the remaining solution was incubated at 37° C. in water bath for 60 min, 120 min and 240 min.

At the end of each incubation time 100 μl of plasma was taken, 100 μl of acetonitrile containing 0.1% of formic acid were added to each aliquot in order to stop the enzymatic reaction and to precipitate the proteins. Samples was vortexed/mixed and centrifuged 5 min at 16434.6 g (=14000 rpm) (4° C.). After centrifugation, the clear supernatant (at least 150 μl) was transferred into 1.2 ml HPLC glass vials and sealed. Samples were placed into the refrigerated autosampler and 20 μl were injected into a HPLC-MS/MS.

The results are expressed with the percentage of test substance remaining by comparing area under specific chromatographic peak of test samples after incubation with area under specific chromatographic peak at T0 (Tables 7 and 8 and FIGS. 1 and 2).

TABLE 7

| Incubation time (min) | Remaining compound 63 (%) (mean ± SEM, n = 2) | |
|---|---|---|
|  | Mouse plasma | Human plasma |
| 0 | 100.0 ± 0.0 | 100.0 ± 0.0 |
| 60 | 9.0 ± 0.8 | 49.2 ± 5.1 |
| 120 | 10.7 ± 8.7 | 27.2 ± 5.4 |
| 240 | 4.9 ± 0.5 | 21.2 ± 11.2 |
| Half-life time: | ~33 min | ~60 min |

TABLE 8

| Incubation time (min) | Compound 38 formed from compound 63 (arbitrary units) (mean ± SEM, n = 2) | |
|---|---|---|
|  | Mouse plasma | Human plasma |
| 0 | 0.6 ± 0.1 | 0.5 ± 0.0 |
| 60 | 3.2 ± 0.1 | 2.5 ± 0.4 |
| 120 | 3.7 ± 0.4 | 2.6 ± 0.1 |
| 240 | 2.9 ± 0.2 | 3.4 ± 0.8 |

In-Vivo Evaluation of Anti-Tumor Activity of Compound 38 in Nude Mice Bearing Subcutaneous Human Colon Carcinoma HCT-116 Xenografts Protocol:

The effects of one compound of the invention were studied on the tumor growth of human cancer cells in nude mice. The human colon carcinoma HCT-116 cell line was obtained from ATCC. The induction in nude mice was realized by subcutaneous injection in the right flank of each mouse of 10×10$^6$ HCT-116 cells in 200 μl serum-free medium. When the tumor volume reached 130 mm$^3$, mice were randomized in to 3 groups (10 mice/group).

Mice of group 1 were treated by intraperitoneal injection of vehicle (solutol HS15 at 38% in NaCl 0.9%) according to the treatment schedule 1Q2Dx3 for 1 week (from D0 to D7) and then 1Q1Dx21 (from D8 to D27).

Mice of group 2 were treated by intraperitoneal injection of cisplatin (diluted in NaCl 0.9%) at 4 mg/kg according to the treatment schedule 1Q3Dx3.

Mice of group 3 were treated by intraperitoneal injection of compound 38 (diluted in solutol HS15 at 38% in NaCl 0.9%) at 37.5 mg/kg according to the treatment schedule 1Q2Dx3 for 1 week (from D0 to D7) and then 1Q1Dx21 (from D8 to D27).

The body weight and tumor volume of mice were recorded twice a week until the end of the experiment. The results are illustrated in Table 9 and FIG. 3.

TABLE 9

Mean body weight change (MBWC) of mice of each group.
At the beginning of the treatment, the mean body weight (MBW) was 21 g.

| Treatment | MBWC D0-D4 | MBWC D0-D7 | MBWC D0-D10 | MBWC D0-D14 | MBWC D0-D17 | MBWC D0-D21 | MBWC D0-D24 | MBWC D0-D28 |
|---|---|---|---|---|---|---|---|---|
| vehicle | −0.48 g | +0.21 g | −0.07 g | −0.18 g | +0.68 g | +0.62 g | +1.04 g | +1.48 g |
| Cisplatin 4 mg/kg | −1.1 g | −2.54 g | −3.33 g | −2.22 g | −1.26 g | −0.38 g | −0.02 g | −0.1 g |
| Cpd 38 37.5 mg/kg | −1.04 g | −0.76 g | −1.08 g | −1.57 g | −1.58 g | −1.43 g | −1.83 g | −2.54 g |

Results:

Antitumor activity was observed in HCT-116 xenograft bearing nude mice, treated with cisplatin at 4 mg/kg, validating the sensitivity of the tumor model to antitumora antitumor agents (FIG. 3).

Antitumor activity was observed in HCT-116 xenograft bearing nude mice and treated with compound 38 at 37.5 mg/kg (FIG. 3).

Compound 38 treatment was well tolerated in nude mice bearing HCT-116 xenograft (table 9).

A moderate loss of body weight was observed during treatment (Table 9 ranging from 4% to 12%).

In-Vivo Evaluation of Anti-Tumor Activity of Compound 38 in Nude Mice Bearing Subcutaneous Human Large Cell Lung Carcinoma NCI-H460 Xenografts Protocol:

The effects of one compound of the invention were studied on the tumor growth of human cancer cells in nude mice. The human large lung carcinoma NCI-H460 cell line was obtained from ATCC. The induction in nude mice was realized by subcutaneous injection in the right flank of each mouse with $5\times10^6$ NCI-H460 cells in 200 µl serum-free medium. When the tumor volume reached 80 mm$^3$, mice were randomized in 2 groups (10 mice/group).

Mice of group 1 were treated by intraperitoneal injection of vehicle (solutol HS15 at 38% in NaCl 0.9%) according to the treatment schedule 1Q1Dx17.

Mice of group 2 were treated by intraperitoneal injection of compound 38 (diluted in solutol HS15 at 38% in NaCl 0.9%) at 37.5 mg/kg according to the treatment schedule 1Q1Dx17.

The tumor volume was recorded twice a week until the end of the experiment.

TABLE 10

Mean body weight change (MBWC) of mice of each group.
At the beginning of the treatment,
the mean body weight (MBW) was 21 g.

| Treatment | MBWC D0-D3 | MBWC D0-D4 | MBWC D0-D7 | MBWC D0-D10 | MBWC D0-D14 | MBWC D0-D17 |
|---|---|---|---|---|---|---|
| vehicle | +0.33 g | +0.16 g | +1.3 g | +1.54 g | +2.48 g | +3.44 g |
| Cpd 38 37.5 mg/kg | −0.96 g | −1.76 g | −1.82 g | −2.12 g | −1.83 g | −1.55 g |

Results:

Antitumor activity was observed on NCI-H460 xenograft bearing nude mice, treated with compound 38 at 37.5 mg/kg (FIG. 4).

Compound 38 treatment was well tolerated in nude mice bearing NCI-H460 xenograft (table 10).

A moderate loss of body weight was observed during treatment (Table 9 ranging from 5% to 10%).

We claim:

1. A method for reducing tumor volume or ameliorating cancer in a subject comprising administering to said subject having a cancer selected from leukemia, acute myelogenous leukemia, lymphoma, breast cancer, pancreatic cancer, lung cancer and colon cancer an effective amount of a pharmaceutical composition comprising (E)-3-(2-(5-bromo-1H-indol-3-yl)-2-cyanovinyl)-4-methoxybenzonitrile, (Z)-3-(2-(5-bromo-1H-indol-3-yl)-2-cyanovinyl)-4-methoxybenzonitrile, or pharmaceutically acceptable salts thereof.

2. The method according to claim 1, wherein said compound is (E)-3-(2-(5-bromo-1H-indol-3-yl)-2-cyanovinyl)-4-methoxybenzonitrile or a pharmaceutically acceptable salt thereof.

3. The method according to claim 1, wherein said compound is (Z)-3-(2-(5-bromo-1H-indol-3-yl)-2-cyanovinyl)-4-methoxybenzonitrile or a pharmaceutically acceptable salt thereof.

4. The method according to claim 1, wherein said pharmaceutical composition further comprises an additional antitumoral drug.

5. The method according to claim 4, wherein said additional antitumoral drug is selected from the group consisting of an anti-mitotic agent, an inhibitor of topoisomerases I or II, a DNA alkylating agent, an anti-metabolic agent, a kinase inhibitor and/or a therapeutic antibody designed to mediate cytotoxicity against cells of said cancer or to modulate a key biological function of said cells.

6. The method according to claim 1, wherein said compound is administered in combination with radiotherapy, hyperthermia and/or other antitumoral therapies, or before, simultaneously and/or after surgery.

7. The method according to claim 1, wherein the cancer is lung cancer.

8. The method according to claim 1, wherein the cancer is pancreatic cancer.

9. The method according to claim 1, wherein the cancer is leukemia.

10. The method according to claim 1, wherein the cancer is acute myelogenous leukemia.

11. The method according to claim 1, wherein the cancer is lymphoma.

12. The method according to claim 1, wherein the cancer is breast cancer.

13. The method according to claim 1, wherein the cancer is colon cancer.

14. The method according to claim 1, said method reducing tumor volume in said subject.

15. The method according to claim 1, said method ameliorating cancer in said subject.

* * * * *

UNITED STATES PATENT AND TRADEMARK OFFICE
CERTIFICATE OF CORRECTION

PATENT NO. : 10,851,054 B2
APPLICATION NO. : 16/257096
DATED : December 1, 2020
INVENTOR(S) : Cecile Bougeret et al.

It is certified that error appears in the above-identified patent and that said Letters Patent is hereby corrected as shown below:

In the Specification

Column 13,
Line 37, "$R_9$ and $R_1$" should read --$R_9$ and $R_{10}$--.

Column 14,
Line 33, "O-carbolinyl" should read --β-carbolinyl--.

Column 41,
Line 34, "$(M+H)+=175$" should read --$(M+H)^+=175$--.

Column 82,
Line 33, "TEA (1111)" should read --TEA (111μl)--.

Column 86,
Line 16, "hydrochloride NC" should read --hydrochloride--.

Column 88,
Line 24, "(581)" should read --(58μl)--.

Signed and Sealed this
Ninth Day of November, 2021

Drew Hirshfeld
*Performing the Functions and Duties of the
Under Secretary of Commerce for Intellectual Property and
Director of the United States Patent and Trademark Office*